US009046519B2

(12) United States Patent
Smith et al.

(10) Patent No.: US 9,046,519 B2

(45) Date of Patent: Jun. 2, 2015

(54) MUTATED THYROTROPIN RECEPTOR

(75) Inventors: Bernard Rees Smith, Cardiff (GB); Jadwiga Furmaniak, Cardiff (GB); Jane Sanders, Cardiff (GB)

(73) Assignee: RSR Limited, Cardiff (GB)

( * ) Notice: Subject to any disclaimer, the term of this patent is extended or adjusted under 35 U.S.C. 154(b) by 1925 days.

(21) Appl. No.: 11/573,676

(22) PCT Filed: Aug. 3, 2005

(86) PCT No.: PCT/GB2005/003040

§ 371 (c)(1),
(2), (4) Date: Jan. 23, 2008

(87) PCT Pub. No.: WO2006/016121

PCT Pub. Date: Feb. 16, 2006

(65) Prior Publication Data

US 2008/0293627 A1 Nov. 27, 2008

(30) Foreign Application Priority Data

Aug. 13, 2004 (GB) .................................. 0418181.4

(51) Int. Cl.

| | |
|---|---|
| ***A61K 38/00*** | (2006.01) |
| ***C07K 14/705*** | (2006.01) |
| ***G01N 33/564*** | (2006.01) |
| ***C07K 14/72*** | (2006.01) |

(52) U.S. Cl.

CPC ............ *G01N 33/564* (2013.01); *C07K 14/723* (2013.01); *G01N 2333/726* (2013.01)

(58) Field of Classification Search

None

See application file for complete search history.

(56) References Cited

FOREIGN PATENT DOCUMENTS

| | | |
|---|---|---|
| WO | 0005345 | 2/2000 |
| WO | 0127634 | 4/2001 |
| WO | 0163296 | 8/2001 |
| WO | 03018632 | 3/2003 |
| WO | 2004050708 | 6/2004 |

OTHER PUBLICATIONS

Smits Guillaume et al, Glycoprotein hormone receptors: determinants in leucine-rich repeats responsible for ligand specificity, The EMBO Journal, Jun. 2, 2003, vol2. 22, No. 11.

Sanders, J., et al, Understanding the thyrotropin receptor function-structure relations, Bailliere's Clinical Endocrinology and Metabolism, T F Davies 1997 11(3): 451-479, Pub. Bailliere Tindall, London.

Sanders, J., et al, The interaction of TSHR autoantibodies with 125I-labelled TSHR, Journal of Clinical Endocrinology and Metabolism, 1999, 84(10), 3797-3802.

Minich, et al, Journal of Endocrinology & Metabolism, 89(1), 352-356, 2004.

*Primary Examiner* — Michael Pak

(74) *Attorney, Agent, or Firm* — Stites & Harbison PLLC; Terry L. Wright

(57) ABSTRACT

A mutated TSHR preparation which includes at least one point mutation characterized in that at least amino acid Arg at a position corresponding to amino acid 255 of a full length human TSHR has been mutated to a different amino acid residue in said mutated TSHR preparation, whereby said mutated TSHR preparation differentially interacts with patient serum stimulating TSHR autoantibodies, patient serum blocking TSHR autoantibodies and TSH, in that (i) the stimulatory effect of patient serum stimulating TSHR autoantibodies interacting with the mutated TSHR preparation is substantially reduced or essentially abolished, when compared to the stimulatory effect of the patient serum stimulating TSHR autoantibodies interacting with a reference TSHR preparation which has an amino acid sequence corresponding to that of said mutated TSHR preparation with the exception that said mutation of Arg at a position corresponding to amino acid 255 of a full length human TSHR is not present in said reference TSHR preparation, (ii) the stimulatory effect of TSH when interacting with the mutated TSHR preparation is essentially unaffected, when compared to the stimulatory effect of TSH interacting with said reference TSHR preparation, and (iii) the blocking effect of patient serum blocking TSHR autoantibodies interacting with the mutated TSHR preparation is essentially unaffected or increased, when compared to the blocking effect of the patient serum blocking TSHR autoantibodies interacting with said reference TSHR preparation, whereby said mutated TSHR preparation is effective in the differential screening and identification of patient serum stimulating TSHR autoantibodies, patient serum blocking TSHR autoantibodies and TSH in a sample of body fluid being screened.

9 Claims, No Drawings

SEQUENCE LISTING

```
<160> NUMBER OF SEQ ID NOS: 26

<210> SEQ ID NO 1
<211> LENGTH: 33
<212> TYPE: DNA
<213> ORGANISM: Artificial
<220> FEATURE:
<223> OTHER INFORMATION: synthesized primer

<400> SEQUENCE: 1

accaagcttg ctggccgtgt ctcaaaccag tgt                                33


<210> SEQ ID NO 2
<211> LENGTH: 33
<212> TYPE: DNA
<213> ORGANISM: Artificial
<220> FEATURE:
<223> OTHER INFORMATION: synthesized primer

<400> SEQUENCE: 2

acactggttt gagacacggc cagcaagctt ggt                                33


<210> SEQ ID NO 3
<211> LENGTH: 33
<212> TYPE: DNA
<213> ORGANISM: Artificial
<220> FEATURE:
<223> OTHER INFORMATION: synthesized primer

<400> SEQUENCE: 3

aggaactgat agcagcaaac acctggactc tta                                33


<210> SEQ ID NO 4
<211> LENGTH: 33
<212> TYPE: DNA
<213> ORGANISM: Artificial
```

<220> FEATURE:
<223> OTHER INFORMATION: synthesized primer

<400> SEQUENCE: 4
taagagtcca ggtgtttgct gctatcagtt cct 33

<210> SEQ ID NO 5
<211> LENGTH: 33
<212> TYPE: DNA
<213> ORGANISM: Artificial
<220> FEATURE:
<223> OTHER INFORMATION: synthesized primer

<400> SEQUENCE: 5
atgggacaaa gctggctgct gtttacctaa aca 33

<210> SEQ ID NO 6
<211> LENGTH: 33
<212> TYPE: DNA
<213> ORGANISM: Artificial
<220> FEATURE:
<223> OTHER INFORMATION: primer

<400> SEQUENCE: 6
tgtttaggta aacagcagcc agctttgtcc cat 33

<210> SEQ ID NO 7
<211> LENGTH: 33
<212> TYPE: DNA
<213> ORGANISM: Artificial
<220> FEATURE:
<223> OTHER INFORMATION: primer

<400> SEQUENCE: 7
agggactatg caatgcaacc ttgacactga agc 33

<210> SEQ ID NO 8
<211> LENGTH: 33
<212> TYPE: DNA
<213> ORGANISM: Artificial
<220> FEATURE:
<223> OTHER INFORMATION: primer

<400> SEQUENCE: 8
gcttcagtgt caaggttgca ttgcatagtc cct 33

<210> SEQ ID NO 9
<211> LENGTH: 33
<212> TYPE: DNA
<213> ORGANISM: Artificial
<220> FEATURE:
<223> OTHER INFORMATION: primer

<400> SEQUENCE: 9
attctttata cttgcaatta cagacaaccc tta 33

<210> SEQ ID NO 10
<211> LENGTH: 33
<212> TYPE: DNA
<213> ORGANISM: Artificial
<220> FEATURE:
<223> OTHER INFORMATION: primer

<400> SEQUENCE: 10
taagggttgt ctgtaattgc aagtataaag aat 33

<210> SEQ ID NO 11
<211> LENGTH: 33
<212> TYPE: DNA
<213> ORGANISM: Artificial
<220> FEATURE:
<223> OTHER INFORMATION: primer

<400> SEQUENCE: 11
agtcacctgc aaggctattc aacgcatccc cag 33

<210> SEQ ID NO 12
<211> LENGTH: 33
<212> TYPE: DNA
<213> ORGANISM: Artificial
<220> FEATURE:
<223> OTHER INFORMATION: primer

<400> SEQUENCE: 12
ctggggatgc gttgaatagc cttgcaggtg act 33

<210> SEQ ID NO 13
<211> LENGTH: 33
<212> TYPE: DNA
<213> ORGANISM: Artificial
<220> FEATURE:
<223> OTHER INFORMATION: primer

<400> SEQUENCE: 13
tctgaagctt attgcgactc acctgagaac tat 33

<210> SEQ ID NO 14
<211> LENGTH: 33
<212> TYPE: DNA
<213> ORGANISM: Artificial
<220> FEATURE:
<223> OTHER INFORMATION: primer

<400> SEQUENCE: 14
atagttctca ggtgagtcgc aataagcttc aga 33

<210> SEQ ID NO 15
<211> LENGTH: 33
<212> TYPE: DNA
<213> ORGANISM: Artificial
<220> FEATURE:
<223> OTHER INFORMATION: primer

<400> SEQUENCE: 15
acctttctta cccagcccac tgctgtgcct tta 33

<210> SEQ ID NO 16
<211> LENGTH: 33
<212> TYPE: DNA
<213> ORGANISM: Artificial
<220> FEATURE:
<223> OTHER INFORMATION: primer

<400> SEQUENCE: 16
taaaggcaca gcagtgggct gggtaagaaa ggt 33

<210> SEQ ID NO 17
<211> LENGTH: 33
<212> TYPE: DNA
<213> ORGANISM: Artificial
<220> FEATURE:
<223> OTHER INFORMATION: primer

<400> SEQUENCE: 17
ctcacacggg ctgccctttc ttacccaagc cac 33

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18
gtggcttggg taagaaaggg cagcccgtgt gag 33

<210> SEQ ID NO 19
<211> LENGTH: 36
<212> TYPE: DNA
<213> ORGANISM: Artificial
<220> FEATURE:
<223> OTHER INFORMATION: primer

<400> SEQUENCE: 19
agcaagaaac accgcgactc ttaagaaact tccact 36

<210> SEQ ID NO 20
<211> LENGTH: 36
<212> TYPE: DNA
<213> ORGANISM: Artificial
<220> FEATURE:
<223> OTHER INFORMATION: primer

<400> SEQUENCE: 20
agtggaagtt tcttaagagt cgcggtgttt cttgct 36

<210> SEQ ID NO 21
<211> LENGTH: 18
<212> TYPE: DNA
<213> ORGANISM: Artificial
<220> FEATURE:
<223> OTHER INFORMATION: primer

<400> SEQUENCE: 21
tagaaggcac agtcgagg 18

<210> SEQ ID NO 22
<211> LENGTH: 20
<212> TYPE: DNA
<213> ORGANISM: Artificial
<220> FEATURE:
<223> OTHER INFORMATION: promotor sequence

<400> SEQUENCE: 22
taatacgact cactataggg 20

<210> SEQ ID NO 23
<211> LENGTH: 33
<212> TYPE: DNA
<213> ORGANISM: Artificial
<220> FEATURE:
<223> OTHER INFORMATION: primer

<400> SEQUENCE: 23
aggaactgat agcagacaac acctggactc tta 33

-continued

```
<210> SEQ ID NO 24
<211> LENGTH: 33
<212> TYPE: DNA
<213> ORGANISM: Artificial
<220> FEATURE:
<223> OTHER INFORMATION: primer

<400> SEQUENCE: 24

taagagtcca ggtgttgtct gctatcagtt cct                              33


<210> SEQ ID NO 25
<211> LENGTH: 40
<212> TYPE: DNA
<213> ORGANISM: Artificial
<220> FEATURE:
<223> OTHER INFORMATION: primer

<400> SEQUENCE: 25

aggaactgat agcagcaaac accgcgactc ttaagaaact                       40


<210> SEQ ID NO 26
<211> LENGTH: 40
<212> TYPE: DNA
<213> ORGANISM: Artificial
<220> FEATURE:
<223> OTHER INFORMATION: primer

<400> SEQUENCE: 26

agtttcttaa gagtcgcggt gtttgctgct atcagttcct                       40
```

MUTATED THYROTROPIN RECEPTOR

The present invention is concerned with thyrotropin receptor (TSHR) preparations, in particular mutated TSHR preparations, antibody and hormone interactions therewith, uses thereof, methods of providing the same, epitope regions and binding sites thus identified for TSHR antibodies, and complexes thereof.

Thyrotropin or thyroid stimulating hormone (TSH) is a pituitary hormone which plays a key role in regulating the function of the thyroid. Its release is stimulated by the hormone TRH formed in the hypothalamus and controls the formation and release of the important thyroid hormones thyroxine (T4) and tri-iodothyronine (T3). On the basis of a feedback mechanism, the thyroid hormone content of the serum controls the release of TSH. The formation of T3 and T4 by the thyroid cells is stimulated by TSH by a procedure in which the TSH released by the pituitary binds to the TSHR of the thyroid cell membrane.

We have recently described in PCT Patent Application WO 2004/050708A2 a human monoclonal antibody to the TSHR, which acts as a powerful thyroid stimulator of the TSHR. The binding site on the TSHR for this monoclonal antibody (hMAb TSHR1) is not disclosed in WO 2004/050708A2, but it has been thought likely that the binding site or pocket is conformational and involves discontinuous regions of the receptor folding together. Identification of the binding site, or epitope region, of the TSHR, or essential binding amino acid residues or sequences thereof, for a human monoclonal or recombinant antibody to the TSHR, such as hMAb TSHR1, would be of crucial importance in the understanding of the TSHR structure and the interaction of human antibodies therewith, and as such should enable improved assessment of autoantibody populations and subsequent management of thyroid disease associated with an autoimmune response to the TSHR.

It is well documented in the art that various types of autoantibodies against the TSHR can be formed in the course of disease associated with autoimmunity to the TSHR. Depending on the type of these autoantibodies, either inhibition of the formation and release of T3 and T4 may occur owing to shielding of the TSHR from TSH molecules, or, on the other hand, these thyroid hormones may be released in an uncontrolled manner because the anti-TSHR autoantibodies mimic the actions of TSH and stimulate the synthesis and release of thyroid hormones.

Autoimmune thyroid disease (AITD) is the most common autoimmune disease affecting different populations worldwide. A proportion of patients with AITD, principally those with Graves' disease, have autoantibodies to the TSHR substantially as hereinbefore described. The autoantibodies bind to the TSHR and usually mimic the actions of TSH, stimulating the thyroid gland to produce high levels of thyroid hormones. These autoantibodies are described as having stimulating activity. Stimulating autoantibodies also interact with TSHRs in eye tissues and cause at least some of the eye signs of Graves' disease. In some patients, autoantibodies bind to the TSHR but do not stimulate thyroid hormone production and are described as having blocking activity [J Sanders, Y Oda, S-A Roberts, M Maruyama, J Furmaniak, B Rees Smith "Understanding the thyrotropin receptor function-structure relationship." Baillière's Clinical Endocrinology and Metabolism. Ed. T F Davies 1997 11(3): 451-479. Pub. Baillière Tindall, London].

Measurements of TSHR autoantibodies are important in the diagnosis and management of AITD, particularly Graves' disease. Currently three types of assays are used to measure TSHR autoantibodies:

(a) competitive binding assays which measure the ability of TSHR autoantibodies to inhibit the binding of TSH to preparations of TSHR;

(b) bioassays which measure the ability of TSHR autoantibodies to stimulate cells expressing the TSHR in culture; and (c) immunoprecipitation of TSHR preparations with TSHR autoantibodies.

Measurement of TSHR autoantibodies using such assays are described in references J Sanders, Y Oda, S-A Roberts, M Maruyama, J Furmaniak, B Rees Smith "Understanding the thyrotropin receptor function-structure relationship"; Baillière's Clinical Endocrinology and Metabolism. Ed; T F Davies 1997 11(3): 451-479. Pub. Baillière Tindall, London; and J Sanders, Y Oda, S Roberts, A Kiddie, T Richards, J Bolton, V McGrath, S Walters, D Jaskólski, J Furmaniak, B Rees Smith "The interaction of TSHR autoantibodies with $^{125}$I-labelled TSHR", Journal of Clinical Endocrinology and Metabolism 1999 84(10):3797-3802.

There are, however, a number of limitations associated with the use of the above described currently available assays for measuring TSHR autoantibodies. The competitive assays of type (a) which are available in different formats are generally sensitive, relatively easy to perform and adaptable for routine use. However, competitive radioreceptor assays known to date for detecting TSHR autoantibodies have fundamental disadvantages of a practical nature (which can be ascribed to the fact that the binding ability of TSHR preparations generally react very sensitively to changes in the receptor or in a biomolecule bound by it) and additionally do not allow differential diagnosis of autoantibody populations to be carried out (for example differentiation of stimulating or blocking autoantibodies as discussed above).

As far as bioassays of the type mentioned in (b) are concerned, these tend to be expensive, time-consuming and require highly skilled staff.

With respect to the direct immunoprecipitation assays of type (c), in practice there are often sensitivity issues associated therewith and again differential diagnosis of autoantibody populations has not been possible to date.

As can be appreciated from the foregoing discussion, there is a need in the art to provide improved assays for TSHR autoantibody detection, and for example it would be advantageous to be able to distinguish between the stimulating and blocking autoantibodies associated with autoimmunity to the TSHR. To this end, WO 01/27634 describes an assay method for carrying out the differential diagnostic determination of TSHR autoantibodies, whereby stimulating TSHR autoantibodies, blocking TSHR autoantibodies and non-pathogenic TSHR autoantibodies (neither stimulating nor blocking) can in theory be selectively determined in a sample. A TSHR-chimera is employed wherein sequences of the TSHR required for binding of stimulating and/or blocking TSHR autoantibodies are replaced by sequences of a different receptor of the G-protein coupled class of receptors. There is also disclosed the use of a solubilised wild type recombinant TSHR in the reaction mixture, when this is required. It can be seen that chimera A represents the TSHR-chimera wherein amino acids 8-165 of the TSHR are replaced by amino acids 10-166 of the lutropin/choriogonadotropin receptor; chimera B represents the TSHR-chimera wherein amino acids 261-370 of the TSHR are replaced by amino acids 261-329 of the lutropin/choriogonadotropin receptor; and chimera C represents the TSHR-chimera wherein amino acids 8-165 and 261-370 of the TSHR are replaced by amino acids 10-166 and 261-370 respectively of the lutropin/choriogonadotropin receptor.

WO 01/63296 similarly describes an assay method for carrying out the differential diagnostic determination of TSHR autoantibodies, whereby stimulating TSHR autoantibodies, blocking TSHR autoantibodies and non-pathogenic TSHR autoantibodies can again in theory be selectively determined in a sample. An optional binding agent (such as wild type recombinant TSHR) which at least binds the autoantibodies being screened is reacted with a sample in the presence of excess selected TSHR-chimera, wherein TSHR binding sequences essential for blocking or stimulating autoantibodies are replaced by sequences which do not bind the respective type of autoantibody being screened. The TSHR-chimeras disclosed in WO 01/63296 correspond to those in WO 01/27634 discussed above.

The above techniques described in WO 01/27634 and WO 01/63296 are further described by Minich et al in Journal of Endocrinology & Metabolism, 89 (1): 352-356.

The rationale for these studies described by Minich and colleagues was reports that TSHR autoantibodies with thyroid stimulating (ie TSH agonist) activity interact with epitopes in the N terminus of the TSHR (between aa 25 and 165), whereas TSHR autoantibodies with TSH antagonist activity interact with epitopes which are more C terminal (aa 261-370). Studies with Chimera A in particular indicated that it bound $^{125}$I-labelled TSH well and cells transfected with this chimera responded well to TSH.

Binding of labelled TSH to both Chimera A and wild type TSHR was inhibited by sera containing TSHR autoantibodies. However the inhibiting effects of the sera were stronger using wild type receptor and this was the case for autoantibodies with TSH agonist and/or TSH antagonist activities. The assay based on inhibition of TSH binding to the chimera appeared to show improved differentiation (compared to wild type TSHR) between TSHR autoantibodies with TSH agonist and TSH antagonist activities, but there was considerable overlap. This overlap limits clinical application. Furthermore, in much earlier studies, assays for TSHR autoantibodies based on inhibition of labelled TSH binding to native (ie wild type) TSHR have been modified to select for TSHR autoantibodies with TSH antagonist activity by reducing assay sensitivity (ie using diluted test samples). This is effective because TSH antagonist autoantibodies are generally present in serum in much higher concentrations than TSH agonist autoantibodies.

In order to provide improved assays for detection and analysis of TSHR autoantibodies produced in response to the TSHR, and to alleviate problems experienced using prior art techniques, the present invention now provides a different approach from the prior art of Minich and colleagues. In particular, we have mutated single aa in the TSHR and investigated the effects of the mutations on TSHR binding and stimulation by various new ligands. These new ligands include a human monoclonal thyroid stimulating autoantibody (hMAb TSHR1), a mouse monoclonal antibody (9D33) which is a powerful hMAb TSHR1 (and TSH) antagonist and mouse monoclonal antibodies which are strong TSH agonists.

In contrast to the prior art, our studies have lead surprisingly to a system which provides much clearer distinction between various TSHR ligands. In particular, we have identified a specific point mutation of the TSHR which essentially abolishes the action of TSHR antibodies (autoantibodies and monoclonal antibodies) with TSH agonist activities whereas the effects of TSH receptor antibodies (autoantibodies and monoclonal antibodies) with TSH antagonist activity are unaffected or increased by the same mutation.

The present invention thus provides a new and improved means of distinguishing between stimulating and blocking TSHR autoantibody populations and there is now provided by the present invention a mutated TSHR preparation which includes at least one point mutation characterised in that at least amino acid Arg at a position corresponding to amino acid 255 of a full length human TSHR has been mutated to a different amino acid residue in said mutated TSHR preparation, whereby said mutated TSHR preparation differentially interacts with patient serum stimulating TSHR autoantibodies, patient serum blocking TSHR autoantibodies and TSH, in that (i) the stimulatory effect of patient serum stimulating TSHR autoantibodies interacting with the mutated TSHR preparation is substantially reduced or essentially abolished, when compared to the stimulatory effect of the patient serum stimulating TSHR autoantibodies interacting with a reference TSHR preparation which has an amino acid sequence corresponding to that of said mutated TSHR preparation with the exception that said mutation of Arg at a position corresponding to amino acid 255 of a full length human TSHR is not present in said reference TSHR preparation, (ii) the stimulatory effect of TSH when interacting with the mutated TSHR preparation is essentially unaffected, when compared to the stimulatory effect of TSH interacting with said reference TSHR preparation, and (iii) the blocking effect of patient serum blocking TSHR autoantibodies interacting with the mutated TSHR preparation is essentially unaffected or increased, when compared to the blocking effect of the patient serum blocking TSHR autoantibodies interacting with said reference TSHR preparation, whereby said mutated TSHR preparation is effective in the differential screening and identification of patient serum stimulating TSHR autoantibodies, patient serum blocking TSHR autoantibodies and TSH in a sample of body fluid being screened.

In a preferred embodiment of the present invention at least amino acid Arg at a position corresponding to amino acid 255 of a full length human TSHR is point mutated to a negatively charged amino acid residue, preferably Asp. Preferably, therefore, there is provided a mutated TSHR preparation which includes at least one point mutation characterised in that at least amino acid Arg at a position corresponding to amino acid 255 of a full length human TSHR has been mutated to Asp in said mutated TSHR preparation, whereby said mutated TSHR preparation differentially interacts with patient serum stimulating TSHR autoantibodies, patient serum blocking TSHR autoantibodies and TSH, in that (i) the stimulatory effect of patient serum stimulating TSHR autoantibodies interacting with the mutated TSHR preparation is substantially reduced or essentially abolished, when compared to the stimulatory effect of the patient serum stimulating TSHR autoantibodies interacting with a reference TSHR preparation which has an amino acid sequence corresponding to that of said mutated TSHR preparation with the exception that said mutation of Arg at a position corresponding to amino acid 255 of a full length human TSHR is not present in said reference TSHR preparation, (ii) the stimulatory effect of TSH when interacting with the mutated TSHR preparation is essentially unaffected, when compared to the stimulatory effect of TSH interacting with said reference TSHR preparation, and (iii) the blocking effect of patient serum blocking TSHR autoantibodies interacting with the mutated TSHR preparation is essentially unaffected or increased, when compared to the blocking effect of the patient serum blocking TSHR autoantibodies interacting with said reference TSHR preparation, whereby said mutated TSHR preparation is effective in the differential screening and identification of patient serum stimulating TSHR autoantibodies, patient serum blocking TSHR autoantibodies and TSH in a sample of body fluid being screened.

Suitably a mutated TSHR preparation as provided by the present invention can include a full length wild type human TSHR, which has been mutated as described above. Alternatively, the mutated TSHR preparation can include fragments of a full length wild type human TSHR mutated as described above and which fragments differentially interact with patient serum stimulating TSHR autoantibodies, patient serum blocking TSHR autoantibodies and TSH again as described above. Further amino acid mutations may be present in a mutated TSHR preparation as described herein, and such further mutations may be point mutations to further enhance the differential interaction of the mutated TSHR preparation with patient serum stimulating TSHR autoantibodies, patient serum blocking TSHR autoantibodies and TSH, or may represent silent substitutions, additions or deletions which do not alter or substantially alter the biological activity or function of the mutated TSHR preparation as provided by the present invention.

In the case where further mutations represent conservative amino acid substitutions, such substitutions are those that substitute a given amino acid in the mutated TSHR preparation by another amino acid of like characteristics. Typically seen as conservative substitutions are the replacements, one for another, among the aliphatic amino acids; among the hydroxyl residues; among the acidic residues; among the amide residues; among the basic residues; and among the aromatic residues.

The term "fragment" as used herein denotes in relation to a mutated TSHR preparation according to the present invention an amino acid sequence that corresponds to part but not all of the amino acid sequence of the wild type human TSHR and which includes mutation of at least amino acid Arg at a position corresponding to amino acid 255 of a full length human TSHR to a different amino acid residue as described herein and which fragment differentially interacts with patient serum stimulating TSHR autoantibodies, patient serum blocking TSHR autoantibodies and TSH, and thus enables differential screening and identification of patient serum stimulating TSHR autoantibodies, patient serum blocking TSHR autoantibodies and TSH in a sample of body fluid being screened. A "fragment" as provided in the context of a mutated TSHR preparation according to the present invention may be "free standing", i.e. not part of or fused to other amino acids or polypeptides, or they may be comprised within a larger polypeptide of which they form a part or region. Such fragments may thus be incorporated in a "scaffold" type polypeptide, wherein additional amino acids are provided to "hold" amino acids of the mutated TSHR fragment preparation in a conformation, arrangement or sequence that resembles or substantially resembles a conformation, arrangement or sequence of amino acids as present in an active site of a wild type TSHR preparation.

Full sequence information for amino acid sequences of wild type human TSHR can be readily obtained by reference to publications in the art, and/or amino acid databases for receptor sequences, and as such full sequences of suitable mutated preparations and mutated fragments based thereon according to the present invention can be readily determined on the basis of the known wild type sequence in conjunction with the disclosure of the present specification.

A mutated TSHR preparation as provided by the present invention has diagnostic utility in the differential screening and identification of patient serum stimulating TSHR autoantibodies, patient serum blocking TSHR autoantibodies and TSH and thus provides a significant step forward in providing reliable diagnosis of autoimmune disease associated with an autoimmune response to the TSHR, alleviating many of the problems associated with diagnostic methods and kits hitherto known in the art as discussed above, and in particular provides advantages over and above the teaching provided by WO 01/63296 and WO 01/27634.

According to the present invention, therefore, there is provided use of a mutated TSHR preparation substantially as hereinbefore described in the differential screening and identification of patient serum stimulating TSHR autoantibodies, patient serum blocking TSHR autoantibodies and TSH, in a sample of body fluid obtained from a subject (in particular a human) suspected of suffering from, susceptible to, having or recovering from autoimmune disease associated with an immune reaction to the TSHR.

There is also provided by the present invention use of a mutated TSHR preparation substantially as hereinbefore described in the diagnosis of autoimmune disease associated with an immune reaction to the TSHR in a subject (in particular a human) suspected of suffering from, susceptible to, having or recovering from autoimmune disease associated with an immune reaction to the TSHR.

The present invention, therefore, further provides a kit comprising a mutated TSHR preparation substantially as hereinbefore described, together with detection means which enable monitoring of the differential interaction of the mutated TSHR preparation with patient serum stimulating TSHR autoantibodies, patient serum blocking TSHR autoantibodies and TSH present in a sample of body fluid being screened.

There is further provided by the present invention a method of differentially screening for patient serum stimulating TSHR autoantibodies, patient serum blocking TSHR autoantibodies and TSH in a sample of body fluid obtained from a subject suspected of suffering from, susceptible to, having or recovering from, autoimmune disease associated with an immune reaction to the TSHR, which method employs a mutated TSHR preparation to differentially interact with and detect patient serum stimulating TSHR autoantibodies, patient serum blocking TSHR autoantibodies and TSH in said sample of body fluid from the subject.

There is further provided by the present invention a method of diagnosing the likely onset or presence of autoimmune disease associated with an immune reaction to the TSHR in a subject (in particular a human) suspected of suffering from, susceptible to, having or recovering from, autoimmune disease associated with an immune reaction to the TSHR, which method employs a mutated TSHR preparation substantially as hereinbefore described to differentially interact with and detect patient serum stimulating TSHR autoantibodies, patient serum blocking TSHR autoantibodies and TSH in a sample of body fluid from the subject, so as to provide a diagnosis of the likely onset or presence of autoimmune disease associated with an immune reaction to the TSHR in the subject.

There is still further provided by the present invention a method of delaying or preventing the onset of autoimmune disease associated with an immune reaction to the TSHR in an animal subject (in particular a human subject) suspected of suffering from, susceptible to or recovering from autoimmune disease associated with an immune reaction to the TSHR, which method employs a mutated TSHR preparation substantially as hereinbefore described to initially differentially interact with and detect stimulating and/or blocking TSHR autoantibodies indicative of the onset or presence of autoimmune disease associated with an immune reaction to the TSHR in a sample of body fluid obtained from the subject, thereby providing a diagnosis of the likely onset of autoimmune disease associated with an immune reaction to the TSHR in the subject, and thereafter therapeutically treating the subject so as to delay the onset and/or prevent autoimmune disease associated with an immune reaction to the TSHR.

There is still further provided by the present invention a method of treating autoimmune disease associated with an immune reaction to the TSHR in a subject, which method employs a mutated TSHR preparation substantially as hereinbefore described to initially differentially interact with and detect stimulating and/or blocking TSHR autoantibodies produced in response to the TSHR in a sample of body fluid obtained from the subject, thereby providing a diagnosis of autoimmune disease in the subject, and administering to the subject a therapeutically effective amount of at least one therapeutic agent effective in the treatment of such autoimmune disease.

The amount of therapeutic agent administered will depend on the specific autoimmune disease state being treated, possibly the age of the patient and will ultimately be at the discretion of an attendant physician.

There is still further provided by the present invention, in combination, a kit substantially as hereinbefore described, together with a therapeutically effective amount of at least one therapeutic agent effective in the treatment of autoimmune disease associated with an immune reaction to the TSHR again substantially as hereinbefore described.

The sample of body fluid being screened by the present invention will typically comprise blood samples or other fluid blood fractions, such as in particular serum samples or plasma samples, but the sample may in principle be another biological fluid, such as saliva or urine or solubilised tissue extracts, or may be obtained by needle biopsy.

A mutated TSHR preparation according to the present invention substantially as hereinbefore described is also suitable for use as a therapeutic agent in the treatment of autoimmune disease associated with an immune reaction to the TSHR, or can be used in the identification of a suitable therapeutic agent for the treatment of autoimmune disease. For example, a mutated TSHR preparation can be used therapeutically to interact with and essentially remove circulating stimulating and/or blocking TSHR autoantibodies in a subject (in particular a human subject) suspected of suffering from, susceptible to, having or recovering from autoimmune disease associated with an immune reaction to the TSHR.

There is, therefore, further provided by the present invention a pharmaceutical composition comprising a mutated TSHR preparation according to the present invention substantially as hereinbefore described, together with a pharmaceutically acceptable carrier, diluent or excipient therefor, wherein the mutated TSHR preparation can differentially interact with stimulating and/or blocking autoantibodies produced in response to the TSHR.

The present invention further provides a mutated TSHR preparation according to the present invention substantially as hereinbefore described for use in the manufacture of a medicament for the treatment of Graves' disease. In particular, a mutated TSHR preparation as provided by the present invention is suitable for use in the manufacture of a medicament for the treatment of at least some of the eye signs of Graves' disease.

Compositions or medicaments according to the present invention should contain a therapeutic or prophylactic amount of a mutated TSHR preparation according to the present invention in a pharmaceutically-acceptable carrier. The pharmaceutical carrier can be any compatible, non-toxic substance suitable for delivery of a mutated TSHR preparation to the patient. Sterile water, alcohol, fats, waxes, and inert solids may be used as the carrier. Pharmaceutically-acceptable adjuvants, buffering agents, dispersing agents and the like, may also be incorporated into the pharmaceutical compositions. Such compositions can contain a single mutated TSHR preparation or may contain two or more mutated TSHR preparations according to the present invention.

Pharmaceutical compositions according to the present invention are useful for parenteral administration. Preferably, the compositions will be administered parenterally, i.e. subcutaneously, intramuscularly, or intravenously. Thus, the invention provides compositions for parenteral administration to a patient, where the compositions comprise a solution or dispersion of a mutated TSHR preparation in an acceptable carrier, as described above. The concentration of a mutated TSHR preparation in the pharmaceutical composition can vary widely, i.e. from less than about 0.1% by weight, usually being at least about 1% by weight to as much as 20% by weight or more. Typical pharmaceutical compositions for intramuscular injection would be made up to contain, for example, 1 ml of sterile buffered water and 1 to 100 μg of a purified mutated TSHR preparation of the present invention. A typical composition for intravenous infusion could be made up to contain 100 to 500 ml of sterile Ringer's solution and 100 to 500 mg of a purified mutated TSHR preparation of the present invention. Actual methods for preparing parenterally administrable compositions are well known in the art and described in more detail in various sources, including, for example, *Remington's Pharmaceutical Science,* $15^{th}$ Edition, Mack Publishing Company, Easton, Pa. (1980).

In accordance with a further aspect of the present invention, there is provided a polynucleotide comprising:

(i) a nucleotide sequence encoding a mutated TSHR preparation substantially as hereinbefore described;
(ii) a nucleotide sequence comprising an allelic variation of the sequence of (i);
(iii) a nucleotide sequence comprising a fragment of the sequence of (i); or
(iv) a nucleotide sequence which hybridizes under stringent conditions to of the sequence of (i).

The present invention further provides primer nucleotide sequences Arg 255 Asp F; Arg 255 Asp R; as identified in Table 1 and/or a nucleotide sequence differing therefrom in codon sequence due to the degeneracy of the genetic code. It will be appreciated that although nucleotide sequences are provided only for the primers given in Table 1, the remaining nucleotides coding TSHR preparations according to the present invention can be readily obtained by reference to publications in the art, and/or nucleotide databases for receptor sequences, given that the full length sequence of wild type human TSHR is known in the art.

More specifically, it can be seen by reference to the specific techniques described in the Examples that mutation present in a polynucleotide sequence as provided by the present invention, and required to effect the point mutation present in a mutated human TSHR preparation according to the present invention, is achieved by the use of the following pair of primer sequences identified in Table 1 Arg 255 Asp F:Arg 255 Asp R—to effect the 255 (Arg) mutation to 255 (Asp). It is further preferred that the primers identified in Table 1 are used in PCR amplification to obtain the required mutated nucleotide sequence and the corresponding mutated human TSHR preparation according to the present invention is suitably obtained by, or is obtainable by, expression of a polynucleotide according to the present invention. A mutated TSHR preparation according to the present invention substantially as herein described can be expressed in various systems generating recombinant proteins. For example, expression in mammalian cells, such as Chinese Hamster Ovary (CHO) cells, can be preferred and the specific use of CHO cells is described in the Examples in conjunction with the pcDNA5.1/FRT vector. Alternatively, a mutated TSHR preparation of the invention can be synthetically produced by conventional peptide synthesizers employing techniques which are well known in the art.

The present invention further provides a process of preparing a mutated TSHR preparation substantially as hereinbefore described, which process comprises:

(i) providing a host cell substantially as described herein;

(ii) growing the host cell; and (iii) recovering a mutated TSHR preparation according to the present invention therefrom.

Recovery of a mutated TSHR preparation according to the present invention can typically employ conventional isolation and purification techniques, such as chromatographic separations or immunological separations, known to one of ordinary skill in the art.

Polynucleotides of the present invention may be in the form of DNA, including, for instance, cDNA, synthetic DNA and genomic DNA appropriately obtained by cloning or produced by chemical synthetic techniques or by a combination thereof. A preferred embodiment of the present invention preferably comprises cDNA or synthetic DNA.

The present invention further relates to variants of the herein above described polynucleotides which encode a mutated TSHR preparation as provided by the present invention. A variant of the polynucleotide may be a naturally occurring variant such as a naturally occurring allelic variant, or it may be a variant that is not known to occur naturally. Such non-naturally occurring variants of the polynucleotide may be made by mutagenesis techniques.

Among the variants in this regard are variants that differ from the aforementioned polynucleotides by nucleotide substitutions, deletions or additions. The substitutions, deletions or additions may involve one or more nucleotides. Alterations in the coding regions may produce conservative or non-conservative amino acid substitutions, deletions or additions.

Variant polynucleotides according to the present invention are suitably at least 70% identical over their entire length to a polynucleotide encoding a mutated TSHR preparation as described herein, and polynucleotides which are complementary to, or hybridise to, such polynucleotides. Alternatively, most highly preferred are polynucleotides that comprise a region that is at least 80% identical over its entire length to a polynucleotide encoding a mutated TSHR preparation as described herein and polynucleotides which are complementary to, or hybridise to, such polynucleotides. In this regard, polynucleotides at least 90% identical over their entire length to the same are particularly preferred, and among these particularly preferred polynucleotides, those with at least 95% identity are especially preferred. Furthermore, those with at least 97% identity are highly preferred among those with at least 95% identity, and among these those with at least 98% identity and at least 99% identity are particularly highly preferred, with at least 99% identity being the more preferred.

Substantially as hereinbefore described the present invention further relates to polynucleotides that hybridise to the herein above-described sequences. In this regard, the present invention especially relates to polynucleotides which hybridise under stringent conditions to the herein above-described polynucleotides. As herein used, the term "stringent conditions" means hybridisation will occur only if there is at least 95% and preferably at least 97% complementary identity between the sequences.

The present invention also relates to vectors, which comprise a polynucleotide or polynucleotides of the present invention, host cells which are genetically engineered with vectors of the invention and the production of a mutated TSHR preparation as described herein of the invention by recombinant techniques.

The present invention, therefore, further provides a biologically functional vector system which carries a polynucleotide substantially as hereinbefore described and which is capable of introducing the polynucleotide into the genome of a host organism.

Host cells can be genetically engineered to incorporate polynucleotides and express a mutated TSHR preparation of the present invention and the present invention further provides a host cell which is transformed or transfected with a polynucleotide, or one or more polynucleotides, or a vector system, each substantially as herein described. The appropriate DNA sequence may be inserted into the vector by any of a variety of well-known and routine techniques.

The present invention further provides a process of identifying a mutated TSHR preparation that can be used for differential screening and identification of patient serum stimulating TSHR autoantibodies, patient serum blocking TSHR autoantibodies and TSH in a sample of body fluid, which process comprises identifying potential interacting regions of the TSHR and amino acid residues present therein which are further identified by virtue of their ability (including different ability relative to wild type TSHR) to interact with a binding partner for the TSHR (such as hMAb TSHR1, 9D33 or TSH), as being candidate amino acids required for interaction of the TSHR with one or more of patient serum stimulating TSHR autoantibodies, patient serum blocking TSHR autoantibodies and TSH; carrying out point mutations of said candidate amino acids and monitoring the interaction of the resulting mutated TSHR preparation with the binding partner, so as to identify point mutations which result in inhibition of the interaction of the resulting mutated TSHR with at least one of patient serum stimulating TSHR autoantibodies, patient serum blocking TSHR autoantibodies and TSH.

The present invention can also be used to identify amino acid residues which are key to epitope regions of the TSHR, whereby there is provided a process which comprises identifying potential interacting regions of the TSHR and amino acid residues present therein which are further identified by virtue of their ability (including different ability relative to wild type TSHR) to interact with a binding partner for the TSHR (such as hMAb TSHR1, 9D33 or TSH), as being candidate amino acids required for interaction of the TSHR with one or more of patient serum stimulating TSHR autoantibodies, patient serum blocking TSHR autoantibodies and TSH; and carrying out point mutations of said candidate amino acids and monitoring the interaction of the resulting mutated TSHR preparation with the binding partner, so as to identify key amino acids required for the respective interaction of the TSHR with one or more of patient serum stimulating TSHR autoantibodies, patient serum blocking TSHR autoantibodies and TSH.

The present invention can further be employed to identify amino acid residues required for conformation of said TSHR so as to enable interaction thereof with one or more of patient serum stimulating TSHR autoantibodies, patient serum blocking TSHR autoantibodies and TSH, whereby there is provided a process which comprises identifying potential interacting regions of the TSHR and amino acid residues present therein which are further identified by virtue of their ability (including different ability relative to wild type TSHR) to interact with a binding partner for the TSHR (such as hMAb TSHR1, 9D33 or TSH), as being candidate amino acids required for conformation of said TSHR so as to enable interaction thereof with said one or more of patient serum stimulating TSHR autoantibodies, patient serum blocking TSHR autoantibodies and TSH; carrying out point mutations of said candidate amino acids and monitoring the interaction of the resulting mutated TSHR preparation with the binding partner, so as to identify key amino acids required for conformation of said TSHR so as to enable the respective interaction of the TSHR with one or more of patient serum stimulating TSHR autoantibodies, patient serum blocking TSHR autoantibodies and TSH to be identified.

In each of the above processes the interaction of the mutated TSHR preparation which is monitored is preferably stimulation of the mutated TSHR, or blocking of such stimulation, by monitoring the production of cyclic AMP as a result of interaction of the binding partner with the mutated TSHR preparation.

As described herein, amino acid Arg present at a position corresponding to amino acid number 255 of a full length human TSHR has been identified by the present invention as a key amino acid of the human TSHR required for antibody binding and furthermore that mutation thereof can achieve differential diagnosis of stimulating and blocking antibody populations.

According to the present invention, therefore, there is provided amino acid Arg present in a TSHR preparation at a position corresponding to amino acid number 255 of a full length human TSHR, for use as a binding site for TSHR antibodies. There is further provided by the present invention amino acid Arg present in a TSHR preparation at a position corresponding to amino acid number 255 of a full length human TSHR, for use as a binding site for TSHR receptor autoantibodies, or one or more fragments thereof. There is further provided by the present invention amino acid Arg present in a TSHR preparation at a position corresponding to amino acid number 255 of a full length human TSHR, for use as a binding site for a TSHR binding partner which comprises or is derived from a human monoclonal or recombinant antibody, or one or more fragments thereof. There is further provided by the present invention use of a mutated amino acid residue present in a mutated TSHR preparation at a position corresponding to amino acid number 255 of a full length human TSHR, for the differential screening of one or more of patient serum stimulating TSHR autoantibodies, patient serum blocking TSHR autoantibodies and TSH, in a sample of body fluid being screened, and preferably in identifying stimulating TSHR autoantibodies as being absent from, or present in, the sample of body fluid. There is further provided by the present invention use of a mutated amino acid residue present in a mutated TSHR preparation at a position corresponding to amino acid number 255 of a full length human TSHR, for the diagnosis of autoimmune disease associated with the TSHR. More specifically, there is provided by the present invention use of Asp present in a mutated TSHR preparation at a position corresponding to amino acid number 255 of a full length human TSHR, for the differential screening of one or more of patient serum stimulating TSHR autoantibodies, patient serum blocking TSHR autoantibodies and TSH, in a sample of body fluid being screened, and preferably in identifying stimulating TSHR autoantibodies as being absent from, or present in, the sample of body fluid. There is further provided by the present invention use of Asp present in a mutated TSHR preparation at a position corresponding to amino acid number 255 of a full length human TSHR, for the diagnosis of autoimmune disease associated with the TSHR.

There is also provided by the present invention a binding complex which comprises (a) a binding site as represented by Arg present at a position corresponding to amino acid number 255 of a full length human TSHR, and (b) a binding partner therefor, which binding partner preferably comprises or is derived from a human monoclonal or recombinant antibody, or one or more fragments thereof.

Suitably the binding partner comprises, or is derived from, a human monoclonal antibody, or one or more fragments thereof, reactive with the TSHR. Alternatively, the binding partner comprises, or is derived from, a human recombinant antibody, or one or more fragments thereof, reactive with the TSHR. Preferably the binding partner comprises a human monoclonal or recombinant antibody, or one or more fragments thereof, reactive with the TSHR. Preferably, the binding partner can be further characterised by its ability to inhibit TSH binding to the TSHR, and/or its ability to stimulate the TSHR, both of which have been seen to be comparable to the respective inhibitory and stimulatory properties of TSHR autoantibodies present in sera obtained from patients with Graves' disease.

A particularly preferred binding partner of a complex as provided by the present invention is human TSHR monoclonal antibody hMAb TSHR 1 as described in PCT Patent Application WO 2004/050708A2. As discussed above in the context of the prior art, the binding site of hMAb TSHR1 has not been disclosed and in view of the complex nature of the TSHR and also the heterogeneous nature of the antibody response thereto, it could not have been possible on the basis of the prior art disclosure to determine or predict the epitope region or binding site therefor.

The following illustrative explanations are provided to facilitate understanding of certain terms used herein. The explanations are provided as a convenience and are not limitative of the invention BINDING PARTNER FOR THE TSHR describes a molecule having a binding specificity for the TSHR. A binding partner as described herein may be naturally derived or wholly or partially synthetically produced. Such a binding partner has a domain or region which specifically binds to and is therefore complementary to one or more epitope regions of the TSHR, and can include stimulating and/or blocking antibodies to the TSHR, which may be autoantibodies, monoclonal or recombinant antibodies, or other ligands, such as TSH.

BINDING SITE means a site, such as an atom, functional group, or amino acid residue of the TSHR, which may bind to a TSHR antibody or other ligand or binding partner therefor. Depending on the particular molecule in the cavity, sites may exhibit attractive or repulsive binding interactions, brought about by charge, steric considerations and the like.

BLOCKING OF THE TSHR by a binding partner denotes the ability of the binding partner to bind to the TSHR and to thereby inhibit, for example, production of cyclic AMP formed as a result of TSHR stimulation as described herein.

BLOCKING TSHR ANTIBODIES bind to the TSHR and effect blocking of the TSHR as described herein.

DIFFERENTIALLY INTERACT or DIFFERENTIAL INTERACTION, with respect to a mutated TSHR preparation as provided by the present invention, means that (i) the stimulatory effect of patient serum stimulating TSHR autoantibodies interacting with the mutated TSHR preparation is substantially reduced or essentially abolished, when compared to the stimulatory effect of the patient serum stimulating TSHR autoantibodies interacting with a reference TSHR preparation which has an amino acid sequence corresponding to that of the mutated TSHR preparation with the exception that the mutation of Arg at a position corresponding to amino acid 255 of a full length human TSHR is not present in the reference TSHR preparation, (ii) the stimulatory effect of TSH when interacting with the mutated TSHR preparation is essentially unaffected, when compared to the stimulatory effect of TSH interacting with the reference TSHR preparation, and (iii) the blocking effect of patient serum blocking TSHR autoantibodies interacting with the mutated TSHR preparation is essentially unaffected or increased, when compared to the blocking effect of the patient serum blocking TSHR autoantibodies interacting with the reference TSHR preparation. The interactions discussed above (whether inhibited, unchanged or enhanced) are in the context of either stimulation of the TSHR, or blocking of the TSHR. With respect to binding interaction, or affinity, of a mutated TSHR preparation with patient serum stimulating TSHR autoantibodies, patient serum blocking TSHR autoantibodies and TSH, as described in further detail in the Examples this may not in certain instances seem to correspond to the results observed with respect to stimulation and/or blocking of mutated TSHR preparations as provided by the present invention, but may for example be due to reduced expression levels of the mutated receptor.

"F" in the context of the primer definitions and naming thereof denotes a forward primer.

HOST CELL is a cell which has been transformed or transfected, or is capable of transformation or transfection by an exogenous polynucleotide sequence.

IDENTITY, as known in the art, is the relationship between two or more polypeptide sequences, or two or more polynucleotide sequences, as determined by comparing the sequences.

MUTATED TSHR PREPARATION denotes a TSHR preparation which includes one or more point mutations characterised in that the resulting TSHR preparation enables differential screening and identification of patient serum stimulating TSHR autoantibodies, patient serum blocking TSHR autoantibodies and TSH in a sample of body fluid being screened. Specifically, however, a mutated TSHR preparation as provided by the present invention includes at least one point mutation characterised in that at least amino acid Arg at a position corresponding to amino acid 255 of a full length human TSHR has been mutated to a different amino acid residue in the mutated TSHR preparation.

POINT MUTATION denotes replacement of an amino acid or nucleotide by another amino acid or nucleotide. This encompasses within the scope of the present invention point mutation achieved by the use of PCR primers and subsequent expression of the mutated nucleotide sequences. Also encompassed within the wording point mutation as used herein are mutations that can be achieved by known synthesis techniques, for example employing conventional peptide synthesizers to effect synthesis of a desired polypeptide sequence wherein the synthesised sequence will include replacement of a desired amino acid with another amino acid.

"R" in the context of the primer definitions and naming thereof denotes a reverse primer.

STIMULATION OF THE TSHR by a binding partner as described herein denotes the ability of the binding partner to bind to the TSHR and to thereby effect, for example, production of cyclic AMP as a result of such binding to the TSHR. Such stimulation is analogous to the responses seen on binding of TSH, or TSHR autoantibodies, to the TSHR and in this way a binding partner as described herein mimics the effect of TSH, or TSHR autoantibody, binding to the TSHR.

STIMULATING TSHR ANTIBODIES bind to the TSHR and effect stimulation of the TSHR as described herein.

TSH denotes thyrotropin or thyroid stimulating hormone.

TSHR denotes thyrotropin or thyroid stimulating hormone receptor, also referred to in the art as TSH receptor.

TSHR AUTOANTIBODIES denote antibodies produced against the TSHR in the course of autoimmune disease associated with the TSHR. Depending on the type of antibodies produced, either inhibition of the formation and release of T3 and T4 may occur owing to shielding of the TSHR from TSH molecules, or, on the other hand T3 and T4 may be released in an uncontrolled manner because the produced antibodies mimic the actions of the TSH and stimulate the synthesis and release of thyroid hormones.

TSHR PREPARATION denotes a polypeptide sequence which can correspond to full length wild type TSHR, or can include one or more variants, analogues, derivatives or fragments thereof as described herein.

The present invention will now be illustrated by the following Figures and Examples, which do not limit the scope of the invention in any way.

EXAMPLES

Various amino acids in the extracellular domain of the TSHR were selected and mutated to alanine. These aa included:—

Asp43 because it is a charged residue (charge-charge interactions are known to be important in the interaction of the TSHR with TSHR autoantibodies and with TSH (Rees Smith B, McLachlan S M, Furmaniak J 1988 Autoantibodies to the thyrotropin receptor. Endocr Rev 9: 106-121). In addition Asp43 is located in the first (ie most N terminal) repeat of the leucine rich domain (LRD; aa 36-281) of the TSHR. Similarly Glu61 was chosen because of being charged and in the $2^{nd}$ repeat of the TSHR LRD.

Glu157 (in the $6^{th}$ repeat of the TSHR LRD) was selected on the basis of being charged and its proposed involvement in forming a salt bridge with TSHR Lys183 (Duprez L, Parma J, Costagliola S, Hermans J, Van-Sande J, Dumont J E, Vassart G 1997 Constitutive activation of the TSHR by spontaneous mutations affecting the N-terminal extracellular domain. FEBS Letters 409: 469-474). Two additional charged aa, Glu178 and Asp203 were selected on the basis of their position in the $7^{th}$ and $8^{th}$ repeats of the LRD respectively.

Charged aa Asp232 and Arg255 were selected on the basis of their positions in the $9^{th}$ and $10^{th}$ repeats of the TSHR LRD respectively. Also an aromatic aa Trp258 in the $10^{th}$ repeat of the LRD was mutated to alanine. Furthermore, aa Asp276 and Ser281 at the C terminus of the LRD were mutated because of their proposed involvement in TSHR activation (Corvilain B, Van Sande J, Dumont J E and Vassart G 2001 Somatic and germline mutations of the TSH receptor and thyroid disease. Clin Endocrinol 55:143-158; and Russo D, Arturi F, Chieari E, Filetti S 1997 Molecular insights into TSHR abnormality and thyroid disease. J Endocrinol Invest 20: 36-47).

Methods

Introduction of Specific Amino Acid Mutations into the Human TSHR Sequence Using PCR The TSHR full length nucleotide sequence (Swiss prot accession number: P16473; NCB1 Entrez Nucleotide accession number NM_000369 was cloned into pcDNA5.1/FRT vector (Invitrogen) using BamHI and XhoI restriction sites following standard cloning procedures.

Specific "forward" and "reverse" PCR primers were designed for each mutation (Table 1) to change the nucleotide coding sequence to code for the appropriate amino acid mutation. Two separate PCR reactions were set up (PCR 1 and PCR 2).

Reagents added in PCR1 reactions: 32.5 μL $H_2O$, 2.5 μL 20× deoxynucleotide triphosphates (dNTPs) (5 mmol/L), 5 μL 10×Pfu DNA polymerase buffer (10×Pfu buffer; Promega), 2.5 μL of 10 pmol/μL T7 primer (Table 1), 2.5 μL of 10 pmol/μL "reverse" primer for mutation, 4 μL pcDNA5.1/FRT TSHR template DNA (100 ng) and 1 μL Pfu DNA polymerase (3 units, Promega). Reagents added in PCR2 reactions: 34.5 μL $H_2O$), 2.5 μL 20× dNTPs (5 mmol/L conc), 5 μL 10×Pfu buffer, 2.5 μL "forward" primer for mutation (Table 1) 10 pmol/μL, 2.5 μL bovine growth hormone polyadenylation signal reverse primer (BGHR primer) (Table 1) 10 pmol/μL, 2 μL template DNA (100 ng) and 1 μL Pfu DNA polymerase (3 units).

The amount of template DNA used is dependent on the length of the PCR products to be made. In the example shown above, PCR 1 product is 800 base pair long and PCR 2 product is 1600 base pair long. The sizes of PCR1 and PCR 2 products depend on the location of the amino acid to be mutated within the TSHR sequence.

The PCR reactions were carried out using a GeneAmp PCR System 9700 (Applied Biosystems) at 94° C. for 5 min followed by 30 cycles of 94° C. for 1 min, 40° C. for 1 min and 72° C. for 2 min (with 50% ramp rates from 94° C. to 40° C. and 40° C. to 72° C.) followed by 72° C. for 7 min thereafter the reaction was cooled to 4° C.

PCR1 and PCR 2 products were run on 1% agarose gels in TAE buffer (40 mmol/L Tris-HCl pH 8.0, 1 mmol/L EDTA, 0.114% glacial acetic acid) and the bands excised from the gel using a scalpel blade. The bands were cleaned using a Geneclean II kit (Anachem Ltd, Luton, LU2 OEB, UK) following the manufacturer's instructions. The concentration of DNA was determined using standard methods in the art. This DNA was used to set up PCR 3 reaction to construct the whole TSHR sequence containing the mutation. The PCR 3 reactions contained: 2.5 μL 10× Pfu buffer, 1 μL of 20× dNTPs, 200 ng of PCR 1 product and 200 ng of PCR 2 product, 1 μL Pfu DNA polymerase and water to 25 μL final volume. This reaction was placed in the GeneAmp PCR system for 7 cycles of 94° C. 1.5 min, 65° C. 1.5 min and 72° C. for 1.5 min. The temperature was then increased to 94° C. for 2 min and the PCR 4 reaction (2.5 μL 10×Pfu buffer, 1.3 μL 20× dNTPs, 2.5 μL T7 primer 10 pmol/μL, 2.5 μL BGHR primer 10 pmol/L, 1 μL Pfu DNA polymerase and water to 25 μL) was added to PCR 3. This mixture was taken through 30 cycles of 94° C. 1 min, 52° C. 1 min and 72° C. 2 min (with a 50% ramp rate from 94° C. to 52° C. and from 52° C. to 72° C.) followed by 10 min at 72° C. thereafter the reaction was cooled to 4° C.

The PCR product was cleaned using 50 μL of a 1:1 phenol/chloroform mixture precipitated with sodium acetate and ethanol and air dried as described in the art. The DNA was then resuspended in 1× buffer B for restriction digest (Roche Diagnostics, Lewes, BN7 1LG,UK) and cut with BamHI/XhoI restriction enzymes for 4 hours at 37 C. The PCR band was run on a 1% agarose gel and the band excised and cleaned using a Geneclean II kit. The PCR product was then ligated into BamHI/XhoI cut pBluescript (Stratagene) and the mutations were verified using DNA sequencing (Sequenase version 2 DNA sequencing kit from Amersham Biosciences) as described in the art. The mutated TSHR DNA was then removed from pBluescript using BamHI/XhoI restriction enzymes and cloned into the pcDNA 5.1/FRT vector (Invitrogen) and the sequence was again verified as above.

Transfection of Mutated TSHR Constructs into CHO Cells Using the Flp-In System

A confluent flask of Flp-In-CHO cells (Invitrogen) was used to seed 24 well plate wells at $1\times10^5$-$1.5\times10^5$ cells/well in DMEM (Invitrogen), 10% foetal calf serum (FCS) (Invitrogen), 1×L-Glutamine (Invitrogen) and 1× non-essential amino acids (NEAA) (Invitrogen) with no antibiotics. The cells were incubated overnight at 37° C., 5% $CO_2$ and >95% humidity.

The pcDNA5.1/FRT TSHR DNA (described above) and POG44 DNA (Invitrogen) were diluted to give 0.01 μg/mL and 0.1 μg/mL solutions, respectively in sterile water. The POG44 DNA and the TSHR DNA were mixed at 3 different concentrations: (1) 9 μL of POG44, 10 μL TSHR DNA and 31 μL Optimem I (Invitrogen); (2) 8 μL POG44, 20 μL TSHR DNA and 22 μL Optimem I; (3) 9.5 μL POG44, 5 μL TSHR DNA and 35.5 μL Optimem I and incubated at room temp for 5 min. 50 μL of 1:25 diluted lipofectamine (Invitrogen) in Optimem I was added to each tube (1-3 above) and incubated for 20 min at room temp. Each incubation mixture was then added to 1 well (in a 24 well plate) of 95% confluent Flp-In-CHO cells and incubated overnight under conditions described above. The culture media was then removed and changed for DMEM, 10% FCS, 1×L-glutamine, 1×NEAA and 1× penicillin (100 u/mL)/streptomycin (100 μg/mL) (Invitrogen) and incubation continued overnight. The cells were then detached from the well using 1× trypsin/EDTA solution (Invitrogen) and split into 4 new wells and grown in the media as above with addition of 600 μg/mL of hygromycin (Invitrogen).

The cells transfected with both, the POG44 plasmid DNA and pcDNA5.1/FRT TSHR are capable of inserting the TSHR into the Flp-In-CHO cell genome and conferring hygromycin resistance on the cell so it will be able to grow in hygromycin selection media. The Flp-In system from Invitrogen is so designed that the TSHR in our constructs will be inserted into the FRT site in the Flp-In-CHO cells by the POG44. The Flp-In-CHO cells contain one Flp-In site per cell therefore the TSHR DNAs will be inserted in the same place in the genome in each experiment and it will be present as one copy per cell. This system has the advantage that screening colonies of cells for those with optimum expression levels (followed by cell cloning to find a stable cell line) is not necessary. Consequently, cells expressing mutated TSHR that grow in the hygromycin selection media can be expanded quickly and used in different assays.

Analysis of Stimulation of Cyclic AMP Production

The ability of hMAb TSHR1 and TSH to stimulate the production of cyclic AMP in Flp-In-CHO cells expressing both wild type and mutated TSHRs was analysed according to WO2004/050708A2. Briefly, CHO cells were seeded into 96 well plates (12,500-20,000 cells per well) and incubated for 48 hours in DMEM (Invitrogen) containing 10% foetal calf serum. The DMEM was then removed and dilutions of porcine TSH (RSR Ltd; 0.01-3 ng/mL) and hMAb TSHR1 Fab (0.1-10 ng/mL) in cyclic AMP assay buffer (NaCl free Hank's Buffered Salts solution containing 1 g/L glucose, 20 mmol/L HEPES, 222 mmol/L sucrose, 15 g/L bovine serum albumin (BSA) and 0.5 mmol/L 3 isobutyl-1-methyl xanthine, pH 7.4) were added and incubated for 1 hour at 37° C. in an atmosphere of 5% $CO_2$ in air. After removal of the test solutions, cells were lysed and assayed for cyclic AMP using a Biotrak enzyme immunoassay system from Amersham Biosciences. Experiments with sera containing TSH receptor antibodies with TSH agonist activity were carried out using the same procedure, except that serum samples were diluted 1:10 in cyclic AMP assay buffer prior to the assay.

Measurement of TSH Antagonist Activity

In some experiments, the ability of patient sera and mouse monoclonal antibodies to the TSHR to inhibit the stimulating activity of porcine TSH was assessed. This was carried out by comparing (a) the stimulatory effect of TSH alone with (b) the stimulatory effect of TSH in the presence of patient sera or mouse monoclonal antibody. Briefly, 50 μL of patient serum diluted in cyclic AMP assay buffer or 50 μL of mouse monoclonal antibody were added to the cell wells followed by 50 μL of buffer or 50 μL of TSH (0.6 ng/mL−final concentration 0.3 ng/mL) and incubated as for the stimulation assay described above. After removal of the test solution, cells were lysed and assayed for cAMP using a Biotrak enzyme immunoassay system.

Preparation of Detergent Solubilised Wild Type and Mutated TSHR Preparations

Flp-In-CHO cells expressing either the wild type (wt) or mutated TSHR were grown to confluence in 175 $cm^2$ flasks, the cells washed with Dulbecco's PBS (without calcium and magnesium ions) (Invitrogen) and scraped into 10 mL ice cold buffer A (50 mmol/L NaCl, 10 mmol/L Tris-HCl pH 7.5), containing protease inhibitors from Roche Diagnostics (1 tablet of product code 1836145 per 50 mL of solution) and 1 mmol/L phenylmethylsulphonylfluoride (PMSF)). The cells were pelleted at 1000×g for 5 min at 4° C., the pellet resuspended in 1 mL buffer A and homogenised in a glass homogeniser on ice. The cell membranes were pelleted at 12,000×g for 30 min at 4° C. and resuspended in 6 mL of buffer A plus 0.5 g/L sodium azide and 2.75 g/L iodoacetamide and pelleted as above. The membrane pellet was then resuspended in 1 mL ice cold buffer A containing 1% Triton X-100 and 0.5 g/L sodium azide and homogenised. The solubilized TSHR preparations were centrifuged at 90,000×g for 2 hours at 4° C. and the supernatants stored at −70° C. in aliquots.

Binding of Labelled TSH and Labelled Monoclonal Antibodies to Wild Type or Mutated TSHRs In these experiments, porcine TSH (70 units per mg from RSR Ltd) and monoclonal antibodies (Fab or IgG) both unlabelled and labelled with $^{125}I$ were prepared as described previously (WO2004/050708A2).

Firstly, dilution profiles of each TSHR preparation were set up. In these experiments, plastic tubes (Maxisorp Star; NUNC) were coated overnight at 4° C. with 200 μL of a mouse monoclonal antibody to the TSHR C-terminus at 10 μg/mL in coating buffer (0.1 mmol/L $Na_2CO_3$ pH 9.2). After washing and post-coating (10 mg/mL of BSA in water) the tubes were washed with assay buffer (10 mmol/L Tris-HCl pH 7.8, 50 mmol/L NaCl and 1 mg/mL BSA) containing 0.1% Triton X-100. In the next step, 200 μL of solubilized wild type or mutated TSHR preparations were added to the tubes and incubated overnight at 4 C. The contents of the tubes were then removed by aspiration, the tubes washed with assay buffer and 50 μL of start buffer (RSR Ltd), 50 μL of assay buffer and 50 μL of either $^{125}I$-TSH or $^{125}I$-labelled monoclonal antibody (10,000-15,000 cpm) were added and incubated at room temp for 2 hours with shaking. After aspiration of the solutions, the tubes were washed and counted in a gamma counter.

Dilutions of the TSHR preparations giving between 15-40% of labelled TSH or monoclonal antibody binding were used to prepare TSHR coated tubes for analysis. In some experiments the 50 μL of assay buffer was substituted for solutions with increasing concentrations of unlabelled TSH (0.4-500 munits/mL) or monoclonal antibody (0.001-1.0 μg/mL). The concentrations of bound and free TSH or monoclonal antibody were calculated and a plot of bound against bound/free (Scatchard analysis) was used to calculate the affinity of binding for the TSHR.

Analysis of the Stimulation of CHO Cells Containing Mutated TSHR

The ability of TSH or hMAb TSHR1 to stimulate cyclic AMP production in CHO cells transfected with TSHR containing various mutations was assessed. The results are shown in detail in Tables 2a-2j, 15a-15x, and 27a-27h and summarised in Tables 3, 16 and 28. Most mutations caused some reduction in responsiveness to both TSH and to hMAb TSHR1. However there were clear differences between the effects of the mutations on responsiveness to the hormone and antibody in the cases of Arg80 to Ala, Arg80 to Asp, Tyr82 to Ala, Glu107 to Ala, Arg109 to Ala, Arg109 to Asp, Lys129 to Ala, Lys129 to Asp, Phe130 to Ala, Lys183 to Ala, Lys183 to Asp, Tyr185 to Ala, Asp232 to Ala, Arg255 to Ala, Trp258 to Ala and double mutations Arg255 to Ala and Trp258 to Ala; Trp258 to Ala and Lys183 to Ala; Trp258 to Ala and Tyr185 to Ala. Mutation of any of these amino acids caused a marked reduction in responsiveness to hMAb TSHR1 whereas responsiveness to TSH was essentially maintained.

The effects of mutating Asp232, Arg255 and Trp258 were investigated in some detail. In the case of Asp232 the nearby glutamine (Glu235) was mutated to Ala. However this mutation had little effect (relative to wild type) on stimulation by TSH or hMAb TSHR1 (Table 4a). Similarly, mutation of threonine 257 adjacent to Trp258 had little effect on hormone or antibody stimulation (Table 4b). However, the double mutations of Arg255 to Ala and Trp258 to Ala; Trp258 to Ala and Lys183 to Ala; Trp258 to Ala and Tyr185 to Ala had little or no effect on stimulation by TSH but stimulation by hMAb TSHR1 was essentially abolished (Tables 4c, 27g and 27h respectively). Furthermore, mutation of Arg255 (positively charged aa) to the negatively charged Aspartic acid (instead of neutral Ala) also essentially abolished responsiveness to hMAb TSHR1 but had little or no effect on TSH stimulation (Table 4d). These results are summarised in Tables 5 and 28.

The effect of mutating Arg255 to Asp on the ability of sera containing TSHR autoantibodies from 14 different patients with Graves' disease was also studied and the results are shown in Table 6. As can be seen in the table, CHO cells expressing this mutant had much reduced responsiveness (relative to wild type) to all 14 sera. In contrast, mutation of Arg80 to Ala, Arg80 to Asp, Glu107 to Ala, Arg109 to Ala, Arg109 to Asp, Lys129 to Ala, Lys183 to Ala, Lys183 to Asp affected some sera but did not reduce responsiveness to all of the stimulating sera tested (Tables 19a-19h and summarised in Table 20). Only Arg 255 to Asp and the double mutation Trp258 to Ala and Arg 255 to Ala were able to reduce responsiveness of all sera tested (Tables 6, 19i and summarised in Table 20).

Table 7 shows stimulation of cyclic AMP production by different doses of hMAb TSHR1 IgG and the donor plasma (obtained from the same blood sample used to isolate lymphocytes for the preparation of the hMAb TSHR1 hybridoma) in CHO cells expressing wild type TSHR and TSHR with Arg255 mutated to Asp. The effect of both IgG and plasma on the mutated TSHR were much reduced relative to wild type and the dose response effects were similar. The effects of various mouse monoclonal antibodies with thyroid stimulating activity (mTSMAbs prepared as in WO 03/018632A2) were also tested in terms of their ability to stimulate cyclic AMP production in CHO cells transfected with wild type TSHR and TSHRs with Arg255 mutated to Asp (Table 8), Arg80 to Asp, Glu107 to Ala, Arg109 to Ala, Arg109 to Asp, Lys129 to Ala, Lys183 to Ala, Lys183 to Asp (Tables 21a-g). As can be seen in Table 8 and Tables 21a-g and summarised in Table 22 the stimulating effect of the mTSMAbs was essentially abolished by the mutations. The ability of 4 patient sera with TSH antagonist activity to influence TSH stimulation of cyclic AMP production in CHO cells expressing wild type TSHR and TSHR with Arg255 mutated to Asp was also investigated. All 4 sera acted as powerful TSH antagonists in CHO cells expressing wild type and mutated TSHR (Table 9). Furthermore, dose response studies indicated that the TSH antagonist effect was stronger at lower doses (higher dilution) of patient serum in the cells expressing mutated receptor (Table 10). Furthermore, the mutation Glu107 to Ala showed a similar enhanced antagonist effect with patient sera (Tables 23a and 24) while 2 other mutations, Arg109 to Ala and Lys183 to Ala had no effect (Tables 23b&c and 24) (summary in Table 24). The actions of a mouse monoclonal antibody to the TSHR with strong TSH antagonist (and hMAb TSHR1 antagonist) activities (9D33, described in WO2004/05078A2) were also investigated (Tables 11,13a-j, 17a-v and summary Tables 14 and 18). As can be seen in Table 11, 9D33 was able to block TSH stimulation of CHO cells expressing wild type TSHR or TSHR with Arg255 mutated to Asp. In addition, the antagonist effect of 9D33 was stronger at lower doses in cells expressing mutated receptor (Table 11). Two other mutations Asp160 to Ala and Arg274 to Ala showed enhanced antagonist effect with 9D33 compared to the wild type TSHR (Tables 17n and 17v) while Lys 58 to Ala, Arg80 to Ala, Arg80 to Asp, Tyr82 to Ala, Glu107 to Arg, Arg109 to Ala, Arg109 to Asp, Lys129 to Ala, Lys129 to Asp, Phe134 to Ala and Lys250 to Ala showed reduction in 9D33's ability to block TSH stimulation in CHO cells expressing these mutated TSHRs (Table 17 and summarised in Table 18). However, 19 out of 32 different mutations studied had no effect on 9D33's ability to block TSH stimulation of cyclic AMP (Tables 13, 14, 17 and 18).

Analysis of Binding to Mutated TSHR

The effects of mutating various TSHR aa to alanine, arginine or aspartic acid on the binding of TSH, hMAb TSHR1 and 9D33 MAb are shown in Tables 12, 25, 29 and summary Table 26.

Mutation of Asp43 to Ala, Glu61 to Ala, Asp203 to Ala, Gln235 to Ala, Glu251 to Ala, Asp276 to Ala and Ser281 to Ala had little or no effect on TSH, hMAb TSHR1 or 9D33 binding. However, mutation of Glu107 to Arg, Arg109 to Asp, Lys129 to Asp, Lys183 to Asp and Asp232 to Ala or Arg resulted in TSH, hMAb TSHR1 and 9D33 MAb binding becoming undetectable. Tyr206 to Ala had undetectable binding for TSH and 9D33 while hMAb TSHR1 was not tested. Mutation of Glu157 to Ala, Asp160 to Ala, Lys209 to Ala, Thr257 to Ala and Trp258 to Ala prevented detectable TSH binding but had little or no effect on hMAb TSHR1 and 9D33 MAb binding. Mutation of Lys58 to Ala, Ile60 to Ala and Tyr82 to Ala showed undetectable 9D33 MAb binding while binding to hMAb TSHR1 and TSH was similar to the wild type. Mutation of Arg80 to Ala and Arg80 to Asp resulted in undetectable 9D33 MAb and hMAb TSHR1 binding whereas TSH still bound well. Mutation of Glu107 to Ala and Phe134 to Ala resulted in lower binding affinity for hMAb TSHR1 and 9D33 MAb while TSH still bound well. Mutation of Arg109 to Ala showed a slight reduction in TSH binding while hMAb TSHR1 binding remained unchanged and 9D33 MAb binding was undetectable. Lower binding affinities for both TSH and hMAb TSHR1 were observed when Glu178 was mutated to Ala while 9D33 MAb binding was unaffected. In the case of Lys129 to Ala, TSH still bound well while the affinity for hMAb TSHR1 was markedly reduced and 9D33 MAb binding was undetectable. Mutation of Phe130 to Ala, Tyr185 to Ala and Arg255 to Ala resulted in a marked reduction in hMAb TSHR1 binding and a reduction in 9D33 MAb binding while TSH still bound well. In the case of Arg255 to Asp, TSH binding was undetectable and hMAb TSHR1 binding affinity was markedly reduced while 9D33 MAb binding was unaffected. In the case of Lys250 to Ala, Arg274 to Ala and Tyr279 to Ala, TSH binding was undetectable while hMAb TSHR1 and 9D33 binding affinities were reduced. The mutation Lys183 to Ala increased the binding affinity of TSH (hMAb TSHR1 and 9D33 MAb binding was not tested) (Table 25) as did the double mutation Tyr185 to Ala and Lys183 to Ala (hMAb TSHR1 binding was not tested while 9D33 MAb binding was reduced) (Table 29).

The double mutation Arg255 to Ala and Trp258 to Ala showed undetectable TSH binding, a slightly reduced affinity for hMAb TSHR1 while 9D33 MAb still bound well (Table 25). The mutation Asp232 to Arg and Arg255 to Asp; Asp232 to Ala and Trp258 to Ala; Asp232 to Ala, Arg255 to Ala and Trp258 to Ala; Trp258 to Ala and Lys183 to Ala; Arg255 to Ala and Lys183 to Ala; Trp258 to Ala, Lys183 to Ala and Tyr185 to Ala; Arg255 to Ala, Trp258 to Ala, Tyr185 to Ala and Lys183 to Ala all showed undetectable binding to TSH, hMAb TSHR1 and 9D33 MAb (Table 29). The double mutation Asp232 to Ala and Arg255 to Ala also showed no binding to TSH or 9D33 MAb and the affinity for hMAb TSHR1 was not tested (Table 29). In the case of double mutation Glu157 to Ala and Asp203 to Ala, TSH binding was undetectable, binding to hMAb TSHR1 was similar to wild type while 9D33 MAb binding was reduced (Table 29). Mutation of Glu178 to Ala and Asp203 to Ala; Trp258 to Ala and Tyr185 to Ala; Arg255 to Ala and Tyr185 to Ala; Arg255 to Ala, Trp258 to Ala and Tyr185 to Ala gave undetectable TSH binding, markedly reduced hMAb TSHR1 binding and slightly reduced 9D33 MAb binding (Table 29). In the case of Arg255 to Ala, Lys183 to Ala and Tyr185 to Ala, both TSH and hMAb TSHR1 binding were undetectable while 9D33 MAb binding was reduced (Table 29).

CONCLUSIONS/INTERPRETATION

1) The effects of mutating selected single aa of the TSHR were observed in terms of stimulation of cyclic AMP production by various ligands.

To our surprise, mutation of some aa had a greater influence on hMAb TSHR1 binding and/or stimulation than on TSH binding and/or stimulation. This difference between the effect of hormone and antibody was most evident in the case of mutation of aa Arg80 to Ala, Arg80 to Asp, Tyr82 to Ala, Glu107 to Ala, Arg109 to Ala, Arg109 to Asp, Lys129 to Ala, Lys129 to Asp, Phe130 to Ala, Lys183 to Ala, Lys183 to Asp, Tyr185 to Ala, Asp232 to Ala, Arg255 to Ala and Trp258 to Ala. In addition the double mutation Arg255 to Ala and Trp258 to Ala had a stronger effect than the mutation Arg255 to Ala alone or Trp258 to Ala alone.

Furthermore, mutation of Arg255 to the oppositely charged Asp essentially abolished the stimulatory effects of hMAb TSHR1 while stimulation by TSH was essentially unaffected. Also TSH receptor autoantibodies in 14 different patients with Graves' disease had their stimulatory effect essentially abolished by the Arg255 to Asp mutation as did 6 mouse monoclonal thyroid stimulating antibodies.

In contrast to mutation of Arg255 to Asp, mutation of other TSHR aa including Arg80 to Ala, Arg80 to Asp, Glu107 to Ala, Arg109 to Ala, Arg109 to Asp, Lys129 to Ala, Lys183 to Ala, Lys183 to Asp and double mutation of Arg255 to Ala and Trp258 to Ala reduced or abolished the stimulatory effect of hMAb TSHR1 but not all patient serum TSHR autoantibodies tested.

2) Consequently, and surprisingly mutation of TSHR aa Arg255 was the only one we found which allowed the clear distinction between the stimulatory actions of TSH and patient sera TSHR autoantibodies (including hMAb TSHR1).

3) Patient sera with TSH antagonist activity are effective at blocking TSH stimulation of CHO cells expressing the mutated TSHR (Arg255 Asp mutation). Also, a mouse monoclonal antibody with powerful TSH antagonist activity (9D33) is an effective TSH antagonists in CHO cells expressing wild type or mutated (Arg255 Asp) receptor.

We also found mutation of aa Arg109 to Ala prevented the ability of 9D33 to inhibit TSH stimulation but this mutation had no effect on the ability of a serum TSHR autoantibody (TSH antagonist autoantibody) to block TSH stimulation.

4) Consequently mutation of TSHR Arg255 to Asp essentially abolishes the ability of TSH agonist type TSHR autoantibodies (including hMAb TSHR1) to interact with the receptor. In contrast, TSH antagonist type TSHR autoantibodies (and TSH) are able to react well with the mutated receptor. The TSHR Arg255 to Asp mutation can be used therefore to distinguish between TSHR autoantibodies with TSH agonist and antagonist activities.

5) Analysis of labelled TSH and labelled hMAb TSHR1 binding to wild type and mutated TSHR preparations indicated that the Arg255 to Ala mutation reduced the affinity of the receptor for hMAb TSHR1 but had little effect on TSH binding. This is consistent with the effect of the mutation on stimulation of cyclic AMP production.

In the case of the Asp232 Ala mutation, no binding of hormone or antibody was detectable, probably because of reduced expression levels of the mutated receptor. TSH binding was also undetectable when Trp258 was mutated to Ala whereas hMAb TSHR1 binding was only reduced about 3 fold.

TABLE 1

| Primer name | Sequence (5'-3') | |
|---|---|---|
| Asp232 Ala F | a<br>accaagcttgctggccgtgtctcaaaccagtgt | (SEQ ID No: 1) |
| Asp232 Ala R | t<br>acactggtttgagacacggccagcaagcttggt | (SEQ ID No: 2) |
| Arg255 Ala F | ag<br>aggaactgatagcagcaaacacctggactctta | (SEQ ID No: 3) |
| Arg255 Ala R | ct<br>taagagtccaggtgtttgctgctatcagttcct | (SEQ ID No: 4) |
| Asp203 Ala F | a<br>atgggacaaagctggctgctgtttacctaaaca | (SEQ ID No: 5) |
| Asp203 Ala R | t<br>tgtttaggtaaacagcagccagctttgtcccat | (SEQ ID No: 6) |
| Glu178 Ala F | a<br>agggactatgcaatgcaaccttgacactgaagc | (SEQ ID No: 7) |
| Glu178 Ala R | t<br>gcttcagtgtcaaggttgcattgcatagtccct | (SEQ ID No: 8) |
| Glu157 Ala F | a<br>attctttatacttgcaattacagacaaccctta | (SEQ ID No: 9) |
| Glu157 Ala R | t<br>taagggttgtctgtaattgcaagtataaagaat | (SEQ ID No: 10) |
| Asp43 Ala F | a<br>agtcacctgcaaggctattcaacgcatccccag | (SEQ ID No: 11) |
| Asp43 Ala R | t<br>ctggggatgcgttgaatagccttgcaggtgact | (SEQ ID No: 12) |
| Glu61 Ala F | a<br>tctgaagcttattgcgactcacctgagaactat | (SEQ ID No: 13) |
| Glu61 Ala R | t<br>atagttctcaggtgagtcgcaataagcttcaga | (SEQ ID No: 14) |
| Ser281 Ala F | ag<br>acctttcttacccagcccactgctgtgccttta | (SEQ ID No: 15) |
| Ser281 Ala R | ct<br>taaaggcacagcagtgggctgggtaagaaaggt | (SEQ ID No: 16) |
| Asp276 Ala F | a<br>ctcacacgggctggccctttcttacccaagccac | (SEQ ID No: 17) |

TABLE 1-continued

| Primer name | Sequence (5'-3') | |
|---|---|---|
| Asp276 Ala R | t<br>gtggcttgggtaagaaag**ggc**agcccgtgtgag | (SEQ ID No: 18) |
| Trp258 Ala F | tg<br>agcaagaaacacc**gcg**actcttaagaaacttccact | (SEQ ID No: 19) |
| Trp258 Ala R | ca<br>agtggaagtttcttaagagt**cgc**ggtgtttcttgct | (SEQ ID No: 20) |
| BGH R | tagaaggcacagtcgagg | (SEQ ID No: 21) |
| T7 | taatacgactcactataggg | (SEQ ID No: 22) |
| Arg255 Asp F | aga<br>aggaactgatagca**gac**aacacctggactctta | (SEQ ID No: 23) |
| Arg255 Asp R | tct<br>taagagtccaggtgtt**gtc**tgctatcagttcct | (SEQ ID No: 24) |
| Arg255 Ala/ Trp258 Ala F | ag tg<br>aggaactgatagca**gc**aaacacc**gc**gactcttaagaaact | (SEQ ID No: 25) |
| Arg255 Ala/ Trp258 Ala R | ca ct<br>agtttcttaagagtc**gc**ggtgttt**gc**tgctatcagttcct | (SEQ ID No: 26) |

F = "forward" primer
R = "reverse" primer
BGH R = bovine growth hormone polyadenylation signal reverse primer
T7 = bacteriophage T7 RNA polymerase promoter TABLE 2a Mutation of TSHR Asp43 to Ala

| | Cyclic AMP produced (fmol/cell well) (mean ± SD; n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1636 ± 204 | 1940 ± 48 | 119 |
| 0.3 | 2550 ± 196 | 2772 ± 98 | 109 |
| 1 | 11362 ± 1120 | 12660 ± 3610 | 111 |
| 3 | 14498 ± 1400 | 13308 ± 1030 | 92 |
| 10 | 24914 ± 4330 | 17962 ± 1360 | 72 |
| TSH (ng/mL) | | | |
| 0.01 | 902 ± 168 | 894 ± 104 | 99 |
| 0.03 | 1454 ± 82 | 1532 ± 326 | 105 |
| 0.1 | 4210 ± 240 | 3996 ± 612 | 95 |
| 0.3 | 9158 ± 1440 | 8986 ± 560 | 98 |
| 1 | 20136 ± 1380 | 11864 ± 1200 | 59 |
| 3 | 24812[a] | 13496 ± 920 | 54 |
| Cyclic AMP assay buffer | 616 ± 30 | 680 ± 100 | |
| Experiment 2 | | | |
| hMAb TSHR1 (ng/mL) | | | |
| 0.1 | 1564 ± 390 | 1648 ± 120 | 105 |
| 0.3 | 3594 ± 426 | 3416 ± 522 | 95 |
| 1 | 10750 ± 200 | 6940 ± 530 | 65 |
| 3 | 17850 ± 940 | 16630 ± 1820 | 93 |
| 10 | 24850 ± 3050 | 20064 ± 1040 | 81 |
| TSH (ng/mL) | | | |
| 0.01 | 1000 ± 98 | 742 ± 60 | 74 |
| 0.03 | 1380 ± 326 | 1164 ± 282 | 83 |
| 0.1 | 2920 ± 498 | 2136 ± 142 | 73 |
| 0.3 | 10700 ± 960 | 6650 ± 1040 | 62 |
| 1 | 17200 ± 4010 | 13980 ± 330 | 81 |

TABLE 2a-continued

Mutation of TSHR Asp43 to Ala

| | Cyclic AMP produced (fmol/cell well) (mean ± SD; n = 3) | | Mutated/ Wild |
|---|---|---|---|
| | Wild type TSHR | Mutated TSHR | type (%) |
| 3 | 27864 ± 350 | 14260 ± 1460 | 51 |
| Cyclic AMP assay buffer | 720 ± 22 | 670 ± 116 | |

hMAb TSHR1 Fab was used in all experiments
[a]mean of duplicate

TABLE 2b

Mutation of TSHR Glu61 to Ala

| | Cyclic AMP produced (fmol/cell well) (mean; n = 2) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1648 | 998 | 61 |
| 0.3 | 3678 | 3204 | 87 |
| 1 | 19912 | 16020 | 80 |
| 3 | 25336 | 22304 | 88 |
| 10 | 28292 | 23370 | 83 |
| TSH (ng/mL) | | | |
| 0.01 | 740 | 482 | 65 |
| 0.03 | 824 | 612 | 74 |
| 0.1 | 2324 | 1688 | 73 |
| 0.3 | 4320 | 3392 | 79 |
| 1 | 24168 | 12914 | 53 |

TABLE 2b-continued

| Mutation of TSHR Glu61 to Ala | | | |
|---|---|---|---|
| | Cyclic AMP produced (fmol/cell well) (mean; n = 2) | | Mutated/ Wild |
| | Wild type TSHR | Mutated TSHR | type (%) |
| 3 | 23332 | 15842 | 68 |
| Cyclic AMP assay buffer | 578 | 366 | |
| Experiment 2 hMAb TSHR1 (ng/mL) | | | |
| 0.1 | 1808 | 1312 | 73 |
| 0.3 | 3926 | 2738 | 70 |
| 1 | 11452 | 6400 | 56 |
| 3 | 20400 | 20962 | 103 |
| 10 | 20114 | 26718 | 133 |
| TSH (ng/mL) | | | |
| 0.01 | 992 | 722 | 73 |
| 0.03 | 1796 | 960 | 53 |
| 0.1 | 3316 | 2452 | 74 |
| 0.3 | 10440 | 5296 | 51 |
| 1 | 15826 | 13840 | 87 |
| 3 | 17582 | 19448 | 111 |
| Cyclic AMP assay buffer | 794 | 680 | |

hMAb TSHR1 Fab was used in all experiments

TABLE 2c

| Mutation of TSHR Glu157 to Ala | | | |
|---|---|---|---|
| | Cyclic AMP produced (fmol/cell well) (mean ± SD; n = 3 or mean; n = 2) | | Mutated/ Wild |
| | Wild type TSHR | Mutated TSHR | type (%) |
| Experiment 1 hMAb TSHR1 (ng/mL) | | | |
| 0.1 | 1682 | 1216 | 72 |
| 0.3 | 4150 | 1284 | 31 |
| 1 | 13668 | 6264 | 46 |
| 3 | 17390 | 8366 | 48 |
| 10 | 25920 | 13156 | 51 |
| TSH (ng/mL) | | | |
| 0.01 | 548 | 800 | 146 |
| 0.03 | 760 | 820 | 107 |
| 0.1 | 2560 | 1190 | 46 |
| 0.3 | 5124 | 2668 | 52 |
| 1 | 19034 | 3288 | 17 |
| 3 | 22720 | 12830 | 56 |
| Cyclic AMP assay buffer | 582 | 710 | |
| Experiment 2 hMAb TSHR1 (ng/mL) | | | |
| 0.1 | 1584 ± 66 | 1490 ± 12 | 94 |
| 0.3 | 3568 ± 174 | 2584 ± 250 | 72 |
| 1 | 14560 ± 1680 | 7260 ± 990 | 50 |
| 3 | 16560 ± 2210 | 15350 ± 3370 | 93 |
| 10 | 20900 ± 3930 | 14910 ± 1120 | 71 |
| TSH (ng/mL) | | | |
| 0.01 | 1410 ± 270 | 1330 ± 206 | 94 |
| 0.03 | 1592 ± 28 | 1308 ± 216 | 82 |
| 0.1 | 3788 ± 534 | 1842 ± 54 | 49 |
| 0.3 | 10500 ± 170 | 2500 ± 1730 | 24 |
| 1 | 16730 ± 1650 | 7100 ± 740 | 42 |
| 3 | 32000 | 11380 ± 300 | 36 |
| Cyclic AMP assay buffer | 774 ± 58 | 1124 ± 42 | |

TABLE 2c-continued

| Mutation of TSHR Glu157 to Ala | | | |
|---|---|---|---|
| | Cyclic AMP produced (fmol/cell well) (mean ± SD; n = 3 or mean; n = 2) | | Mutated/ Wild |
| | Wild type TSHR | Mutated TSHR | type (%) |
| Experiment 3 hMAb TSHR1 (ng/mL) | | | |
| 0.1 | 1040 | 1260 | 121 |
| 0.3 | 1644 | 2000 | 122 |
| 1 | 12588 | 10924 | 87 |
| 3 | 15736 | 14816 | 94 |
| 10 | 21950 | 26304 | 120 |
| 0.01 | 708 | 1026 | 145 |
| 0.03 | 914 | 1486 | 163 |
| 0.1 | 2458 | 2008 | 82 |
| 0.3 | 5916 | 2444 | 41 |
| 1 | 17014 | 8382 | 49 |
| 3 | 20002 | 15158 | 76 |
| Cyclic AMP assay buffer | 608 | 988 | |

hMAb TSHR1 Fab was used in all experiments

TABLE 2d

| Mutation of TSHR Glu178 to Ala | | | |
|---|---|---|---|
| | Cyclic AMP produced (fmol/cell well) (mean; n = 2) | | Mutated/ Wild |
| | Wild type TSHR | Mutated TSHR | type (%) |
| Experiment 1 hMAb TSHR1 (ng/mL) | | | |
| 0.1 | 1210 | 1346 | 111 |
| 0.3 | 2710 | 2012 | 74 |
| 1 | 9190 | 4528 | 49 |
| 3 | 13790 | 9524 | 69 |
| 10 | 24166 | 12492 | 52 |
| TSH (ng/mL) | | | |
| 0.01 | 970 | 828 | 85 |
| 0.03 | 1416 | 1148 | 81 |
| 0.1 | 2218 | 1464 | 66 |
| 0.3 | 4564 | 3188 | 70 |
| 1 | 12524 | 9918 | 79 |
| 3 | 18440 | 13722 | 74 |
| Cyclic AMP assay buffer | 540 | 910 | |
| Experiment 2 hMAb TSHR1 (ng/mL) | | | |
| 0.1 | 1354 | 1028 | 76 |
| 0.3 | 3372 | 1424 | 42 |
| 1 | 8820 | 3822 | 43 |
| 3 | 15524 | 8070 | 52 |
| 10 | 19540 | 12040 | 62 |
| TSH (ng/mL) | | | |
| 0.01 | 826 | 648 | 78 |
| 0.03 | 1042 | 810 | 78 |
| 0.1 | 2446 | 1182 | 48 |
| 0.3 | 5626 | 3018 | 54 |
| 1 | 13900 | 8050 | 58 |
| 3 | 19330 | 9080 | 47 |
| Cyclic AMP assay buffer | 804 | 672 | |

hMAb TSHR1 Fab was used in all experiments

TABLE 2e

Mutation of TSHR Asp203 to Ala

| | Cyclic AMP produced (fmol/cell well) (mean ± SD; n = 3 or mean; n = 2) | | Mutated/ Wild |
|---|---|---|---|
| | Wild type TSHR | Mutated TSHR | type (%) |
| Experiment 1 hMAb TSHR1 (ng/mL) | | | |
| 0.1 | 1202 ± 222 | 968 ± 58 | 81 |
| 0.3 | 2508 ± 1198 | 1512 ± 162 | 60 |
| 1 | 8052 ± 1290 | 4824 ± 520 | 60 |
| 3 | 13696 ± 4150 | 8204 ± 310 | 60 |
| 10 | 16974 ± 1920 | 9680 ± 3420 | 57 |
| TSH (ng/mL) | | | |
| 0.01 | 796 ± 34 | 668 ± 96 | 84 |
| 0.03 | 1028 ± 72 | 984 ± 124 | 96 |
| 0.1 | 2216 ± 610 | 1248 ± 82 | 56 |
| 0.3 | nd | 5700 ± 380 | nd |
| 1 | 14976 ± 1990 | 8258 ± 116 | 55 |
| 3 | 18592 ± 1740 | 11406 ± 4130 | 61 |
| Cyclic AMP assay buffer | 804 ± 48 | 614 ± 36 | |
| Experiment 2 hMAb TSHR1 (ng/mL) | | | |
| 0.1 | 1666 | 1712 | 103 |
| 0.3 | 2978 | 2642 | 89 |
| 1 | nd | nd | nd |
| 3 | 15392 | 11414 | 74 |
| 10 | 17498 | 21486 | 123 |
| TSH (ng/mL) | | | |
| 0.01 | 1146 | 660 | 58 |
| 0.03 | 1566 | 1360 | 87 |
| 0.1 | 2048 | 2232 | 109 |
| 0.3 | 5236 | 3112 | 59 |
| 1 | 16252 | 8790 | 54 |
| 3 | 16092 | 16328 | 101 |
| Cyclic AMP assay buffer | 610 | 560 | |

hMAb TSHR1 Fab was used in all experiments
nd = not determined

TABLE 2f

Mutation of TSHR Asp232 to Ala

| | Cyclic AMP produced (fmol/cell well) (mean ± SD; n = 3 or mean; n = 2) | | Mutated/ Wild |
|---|---|---|---|
| | Wild type TSHR | Mutated TSHR | type (%) |
| Experiment 1 hMAb TSHR1 (ng/mL) | | | |
| 0.1 | 1776 | 720 | 41 |
| 0.3 | 4086 | 1442 | 35 |
| 1 | 10000 | 3560 | 36 |
| 3 | 18030 | 8120 | 45 |
| 10 | 11250 | 11210 | 100 |
| TSH (ng/mL) | | | |
| 0.01 | 730 | 632 | 87 |
| 0.03 | 978 | 798 | 82 |
| 0.1 | 2436 | 1998 | 82 |
| 0.3 | 5600 | 5600 | 100 |
| 1 | 10170 | 7400 | 73 |
| 3 | 12800 | 9384 | 73 |
| Cyclic AMP assay buffer | 368 | 586 | |

TABLE 2f-continued

Mutation of TSHR Asp232 to Ala

| | Cyclic AMP produced (fmol/cell well) (mean ± SD; n = 3 or mean; n = 2) | | Mutated/ Wild |
|---|---|---|---|
| | Wild type TSHR | Mutated TSHR | type (%) |
| Experiment 2 hMAb TSHR1 (ng/mL) | | | |
| 0.1 | 1006 ± 156 | 804 ± 384 | 80 |
| 0.3 | 2236 ± 94 | 968 ± 24 | 43 |
| 1 | 11138 ± 1080 | 3894 ± 320 | 35 |
| 3 | 12188 ± 860 | 5984 ± 690 | 49 |
| 10 | 16212 ± 570 | 9476 ± 650 | 58 |
| TSH (ng/mL) | | | |
| 0.01 | 850 ± 54 | 606 ± 34 | 71 |
| 0.03 | 908 ± 148 | 956 ± 152 | 105 |
| 0.1 | 2026 ± 202 | 1652 ± 256 | 82 |
| 0.3 | 4488 ± 2060 | 3632 ± 384 | 81 |
| 1 | 12034 ± 880 | 7280 ± 1070 | 60 |
| 3 | 16886 ± 1400 | 12216 ± 1460 | 72 |
| Cyclic AMP assay buffer | 538 ± 40 | 560 ± 24 | |

hMAb TSHR1 Fab was used in all experiments

TABLE 2g

Mutation of TSHR Arg255 to Ala

| | Cyclic AMP produced (fmol/cell well) (mean ± SD; n = 3 or mean; n = 2) | | Mutated/ Wild |
|---|---|---|---|
| | Wild type TSHR | Mutated TSHR | type (%) |
| Experiment 1 hMAb TSHR1 (ng/mL) | | | |
| 0.1 | 1644 ± 156 | 706 ± 108 | 43 |
| 0.3 | 3370 ± 256 | 808 ± 44 | 24 |
| 1 | 16964 ± 1380 | 4172 ± 660 | 25 |
| 3 | 18078 ± 1210 | 8500 ± 880 | 47 |
| 10 | 17820 ± 1150 | 11208 ± 670 | 63 |
| TSH (ng/mL) | | | |
| 0.01 | 950 ± 86 | 826 ± 50 | 87 |
| 0.03 | 1444 ± 90 | 1416 ± 86 | 98 |
| 0.1 | nd | 3784 ± 1410 | nd |
| 0.3 | 8624 ± 360 | 8920 ± 460 | 103 |
| 1 | 16014 ± 1220 | 12164 ± 1060 | 76 |
| 3 | 16244 ± 1570 | 13128 ± 1170 | 81 |
| Cyclic AMP assay buffer | 830 ± 140 | 718 ± 48 | |
| Experiment 2 hMAb TSHR1 (ng/mL) | | | |
| 0.1 | 1454 | 400 | 28 |
| 0.3 | 3126 | 534 | 17 |
| 1 | 6400 | 2278 | 36 |
| 3 | 11412 | 2606 | 23 |
| 10 | 16878 | 9584 | 57 |
| TSH (ng/mL) | | | |
| 0.01 | 450 | 404 | 90 |
| 0.03 | 778 | 610 | 78 |
| 0.1 | 1710 | 1566 | 92 |
| 0.3 | 4690 | 4680 | 100 |
| 1 | 10082 | 7180 | 71 |
| 3 | 14830 | 11938 | 80 |
| Cyclic AMP assay buffer | 496 | 290 | |

hMAb TSHR1 Fab was used in all experiments
nd = not determined

TABLE 2h

Mutation of TSHR Trp258 to Ala

| | Cyclic AMP produced (fmol/cell well) (mean; n = 2) | | Mutated/ Wild |
|---|---|---|---|
| | Wild type TSHR | Mutated TSHR | type (%) |
| Experiment 1 hMAb TSHR1 (ng/mL) | | | |
| 0.1 | 2040 | 1464 | 72 |
| 0.3 | 4908 | 4198 | 86 |
| 1 | nd | 5964 | nd |
| 3 | 17958 | 11242 | 63 |
| 10 | 29824 | 14208 | 48 |
| TSH (ng/mL) | | | |
| 0.01 | 1354 | 952 | 70 |
| 0.03 | 1464 | 1646 | 112 |
| 0.1 | 2954 | 3592 | 122 |
| 0.3 | 12154 | 10398 | 86 |
| 1 | 17270 | 14774 | 86 |
| 3 | 13142 | 17270 | 131 |
| Cyclic AMP assay buffer | 526 | 390 | |
| Experiment 2 hMAb TSHR1 (ng/mL) | | | |
| 0.1 | 2404 | 1206 | 50 |
| 0.3 | 5902 | 2518 | 43 |
| 1 | nd | nd | nd |
| 3 | 32000 | 9550 | 30 |
| 10 | 32000 | 17782 | 56 |
| TSH (ng/mL) | | | |
| 0.01 | 1026 | 514 | 50 |
| 0.03 | 2000 | 1416 | 71 |
| 0.1 | nd | nd | nd |
| 0.3 | 10716 | 12022 | 112 |
| 1 | 16596 | 13804 | 83 |
| 3 | 26302 | 18620 | 71 |
| Cyclic AMP assay buffer | 698 | 1158 | |

hMAb TSHR1 Fab was used in all experiments
nd = not determined

TABLE 2i

Mutation of TSHR Asp276 to Ala

| | Cyclic AMP produced (fmol/cell well) (mean; n = 2) | | Mutated/ Wild |
|---|---|---|---|
| | Wild type TSHR | Mutated TSHR | type (%) |
| Experiment 1 hMAb TSHR1 (ng/mL) | | | |
| 0.1 | 1490 | 1530 | 103 |
| 0.3 | 3056 | 3208 | 105 |
| 1 | nd | nd | nd |
| 3 | 12136 | 19610 | 162 |
| 10 | 21740 | 24030 | 111 |
| TSH (ng/mL) | | | |
| 0.01 | 1184 | 1282 | 108 |
| 0.03 | 1470 | 1550 | 105 |
| 0.1 | 3188 | 3748 | 118 |
| 0.3 | 9466 | 9180 | 97 |
| 1 | 12796 | 15670 | 122 |
| 3 | 13820 | 23070 | 167 |
| Cyclic AMP assay buffer | 866 | 960 | |
| Experiment 2 hMAb TSHR1 (ng/mL) | | | |
| 0.1 | 1346 | 2130 | 158 |
| 0.3 | 4120 | nd | nd |

TABLE 2i-continued

Mutation of TSHR Asp276 to Ala

| | Cyclic AMP produced (fmol/cell well) (mean; n = 2) | | Mutated/ Wild |
|---|---|---|---|
| | Wild type TSHR | Mutated TSHR | type (%) |
| 1 | nd | nd | nd |
| 3 | 14216 | 15236 | 107 |
| 10 | 18230 | 21320 | 117 |
| TSH (ng/mL) | | | |
| 0.01 | 866 | 1236 | 143 |
| 0.03 | 934 | 1594 | 171 |
| 0.1 | 2124 | 2160 | 102 |
| 0.3 | 5400 | 6000 | 111 |
| 1 | 9880 | 16640 | 168 |
| 3 | 16846 | 20480 | 122 |
| Cyclic AMP assay buffer | 894 | 1132 | |

hMAb TSHR1 Fab was used in all experiments
nd = not determined

TABLE 2j

Mutation of TSHR Ser281 to Ala

| | Cyclic AMP produced (fmol/cell well) (mean; n = 2) | | Mutated/ Wild |
|---|---|---|---|
| | Wild type TSHR | Mutated TSHR | type (%) |
| Experiment 1 hMAb TSHR1 (ng/mL) | | | |
| 0.1 | 1080 | 936 | 87 |
| 0.3 | 3236 | 2490 | 77 |
| 1 | nd | 4722 | nd |
| 3 | 15556 | 10416 | 67 |
| 10 | 27712 | 17190 | 62 |
| TSH (ng/mL) | | | |
| 0.01 | 402 | 828 | 206 |
| 0.03 | 708 | 1152 | 163 |
| 0.1 | 2068 | 1464 | 71 |
| 0.3 | 5200 | 3188 | 61 |
| 1 | 18548 | 9918 | 53 |
| 3 | 24136 | 13722 | 57 |
| Cyclic AMP assay buffer | 550 | 356 | |
| Experiment 2 hMAb TSHR1 (ng/mL) | | | |
| 0.1 | 1500 | 1400 | 93 |
| 0.3 | 4706 | 4486 | 95 |
| 1 | nd | nd | nd |
| 3 | 17110 | 11418 | 67 |
| 10 | 23010 | 16384 | 71 |
| TSH (ng/mL) | | | |
| 0.01 | 402 | 566 | 141 |
| 0.03 | 708 | 1028 | 145 |
| 0.1 | 2068 | 1824 | 88 |
| 0.3 | 5200 | 6250 | 120 |
| 1 | 18548 | 10032 | 54 |
| 3 | 24136 | 14130 | 59 |
| Cyclic AMP assay buffer | 582 | 696 | |

hMAb TSHR1 Fab was used in all experiments
nd = not determined

TABLE 3

| Summary of effects of mutation (relative to wild type) on stimulation of CHO cells containing mutated TSHR | | |
|---|---|---|
| aa mutation | TSH stimulation | hMAb TSHR1 Fab stimulation |
| Asp43 to Ala | some reduction | some reduction |
| Glu61 to Ala | some reduction | some reduction |
| Glu157 to Ala | marked reduction of some TSH doses | marked reduction of some antibody doses |
| Glu178 to Ala | some reduction | some reduction |
| Asp203 to Ala | some reduction | some reduction |
| Asp232 to Ala | some reduction | marked reduction |
| Arg255 to Ala | some reduction | marked reduction |
| Trp258 to Ala | little effect | marked reduction |
| Asp276 to Ala | little effect | little effect |
| Ser281 to Ala | some reduction | some reduction |

TABLE 4a

| Mutation of TSHR Gln235 to Ala | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 1 hMAb TSHR1 (ng/mL) | | | |
| 0.1 | 770 ± 174 | 764 ± 108 | 99 |
| 0.3 | 3020 ± 398 | 2434 ± 140 | 81 |
| 1 | 5904 ± 650 | 6356 ± 970 | 108 |
| 3 | 10538 ± 2380 | 13320 ± 2080 | 126 |
| 10 | 17314 ± 1980 | 13486 ± 2290 | 78 |
| Cyclic AMP assay buffer | 252 ± 58 | 234 ± 24 | |
| TSH (ng/mL) | | | |
| 0.01 | 422 ± 28 | 482 ± 34 | 114 |
| 0.03 | 816 ± 138 | 810 ± 116 | 99 |
| 0.1 | 1412 ± 86 | 1488 ± 264 | 105 |
| 0.3 | 4756 ± 280 | 4358 ± 690 | 92 |
| 1 | 9722 ± 2330 | 12656 ± 160 | 130 |
| 3 | 12826 ± 5000 | 14266 ± 2730 | 111 |
| Cyclic AMP assay buffer | 252 ± 58 | 234 ± 24 | |
| Experiment 2 hMAb TSHR1 (ng/mL) | | | |
| 0.1 | 1958 ± 40 | 1722 ± 172 | 88 |
| 0.3 | 3374 ± 244 | 3378 ± 556 | 100 |
| 1 | 11144 ± 1850 | 11128 ± 350 | 100 |
| 3 | 15536 ± 820 | 18374 ± 3140 | 118 |
| 10 | 17830 ± 1560 | 17616 ± 1750 | 99 |
| Cyclic AMP assay buffer | 518 ± 264 | 374 ± 70 | |
| TSH (ng/mL) | | | |
| 0.01 | 1074 ± 272 | 1054 ± 222 | 98 |
| 0.03 | 2062 ± 310 | 1878 ± 298 | 91 |
| 0.1 | 4192 ± 992 | 2912 ± 254 | 69 |
| 0.3 | 11260 ± 740 | 10458 ± 1240 | 93 |
| 1 | 14364 ± 720 | 18170 ± 1680 | 126 |
| 3 | 18175 ± 1220 | 20128 ± 3240 | 111 |
| Cyclic AMP assay buffer | 518 ± 264 | 374 ± 70 | |

hMAb TSHR1 Fab was used in all experiments

TABLE 4b

| Mutation of TSHR Thr257 to Ala | | | |
|---|---|---|---|
| | Cyclic AMP produced (fmol/cell well) (mean ± SD; n = 3) | | Mutated/ Wild |
| | Wild type TSHR | Mutated TSHR | type (%) |
| Experiment 1 hMAb TSHR1 (ng/mL) | | | |
| 0.1 | 1080 ± 26 | 972 ± 24 | 90 |
| 0.3 | 2438 ± 382 | 1796 ± 366 | 74 |
| 1 | 16096 ± 4100 | 12862 ± 4960 | 80 |
| 3 | 16788 ± 3320 | 11692 ± 1250 | 70 |
| 10 | 23688 ± 3800 | 19994 ± 3380 | 84 |
| Cyclic AMP assay buffer | 550 ± 58 | 402 ± 132 | |
| TSH (ng/mL) | | | |
| 0.01 | 680 ± 54 | 716 ± 216 | 105 |
| 0.03 | 996 ± 96 | 1142 ± 98 | 115 |
| 0.1 | 1752 ± 226 | 3188 ± 364 | 182 |
| 0.3 | 6962 ± 1320 | 6284 ± 100 | 90 |
| 1 | 12316 ± 4250 | 12486 ± 3100 | 101 |
| 3 | 18212 ± 3670 | 16674 ± 1650 | 92 |
| Cyclic AMP assay buffer | 550 ± 58 | 402 ± 132 | |
| Experiment 2 hMAb TSHR1 (ng/mL) | | | |
| 0.1 | 1532 ± 580 | 998 ± 80 | 65 |
| 0.3 | 3656 ± 744 | 2718 ± 286 | 74 |
| 1 | 8516 ± 2600 | 5694 ± 310 | 67 |
| 3 | 23294 ± 6540 | 21948 ± 740 | 94 |
| 10 | 30580 ± 400 | 27366 ± 2330 | 89 |
| Cyclic AMP assay buffer | 690 ± 50 | 584 ± 66 | |
| TSH (ng/mL) | | | |
| 0.01 | 864 ± 62 | 776 ± 34 | 90 |
| 0.03 | 1244 ± 550 | 1084 ± 1.2 | 87 |
| 0.1 | 2882 ± 584 | 3390 ± 294 | 118 |
| 0.3 | 8584 ± 2260 | 6996 ± 680 | 82 |
| 1 | 19548 ± 5380 | 25080 ± 3710 | 128 |
| 3 | 30344 | 31488 ± 430 | 104 |
| Cyclic AMP assay buffer | 690 ± 50 | 584 ± 66 | |

hMAb TSHR1 Fab was used in all experiments

TABLE 4c

| Mutation of TSHR Arg255 to Ala and TSHR Trp258 to Ala | | | |
|---|---|---|---|
| | Cyclic AMP produced (fmol/cell well) (mean ± SD; n = 3) | | Mutated/ Wild |
| | Wild type TSHR | Mutated TSHR | type (%) |
| Experiment 1 hMAb TSHR1 (ng/mL) | | | |
| 0.1 | 1718 ± 92 | 1502 ± 78 | 87 |
| 0.3 | 3116 ± 204 | 1622 ± 428 | 52 |
| 1 | 15540 ± 2370 | 2708 ± 340 | 17 |
| 3 | 14408 ± 1960 | 1958 ± 280 | 14 |
| 10 | 18652 ± 2170 | 5506 ± 130 | 30 |
| TSH (ng/mL) | | | |
| 0.01 | 1968 ± 136 | 1786 ± 66 | 91 |
| 0.03 | 2754 ± 318 | 2628 ± 144 | 95 |
| 0.1 | 4246 ± 196 | 4488 ± 742 | 106 |
| 0.3 | 12026 ± 870 | 12608 ± 1570 | 105 |
| 1 | 18016 ± 3270 | 16362 ± 700 | 91 |
| 3 | 18256 ± 990 | 19162 ± 1230 | 105 |
| Cyclic AMP assay buffer | 1014 ± 220 | 1386 ± 460 | |

TABLE 4c-continued

Mutation of TSHR Arg255 to Ala and TSHR Trp258 to Ala

| | Cyclic AMP produced (fmol/cell well) (mean ± SD; n = 3) | | Mutated/Wild |
|---|---|---|---|
| | Wild type TSHR | Mutated TSHR | type (%) |
| Experiment 2 hMAb TSHR1 (ng/mL) | | | |
| 0.1 | 1778 ± 24 | 646 ± 48 | 36 |
| 0.3 | 3282 ± 622 | 676 ± 14 | 21 |
| 1 | 7054 ± 2380 | 720 ± 270 | 10 |
| 3 | 15036 ± 700 | 1876 ± 240 | 12 |
| 10 | 18292 ± 2130 | 3330 ± 620 | 18 |
| TSH (ng/mL) | | | |
| 0.01 | 910 ± 146 | 796 ± 60 | 87 |
| 0.03 | 1998 ± 252 | 1558 ± 80 | 78 |
| 0.1 | 5492 ± 402 | 4066 ± 644 | 74 |
| 0.3 | 8304 ± 1280 | 7238 ± 850 | 87 |
| 1 | 16858 ± 1210 | 13718 ± 1250 | 81 |
| 3 | 17088 ± 2130 | 18132 ± 2870 | 106 |
| Cyclic AMP assay buffer | 666 ± 88 | 662 ± 78 | |

hMAb TSHR1 Fab was used in all experiments

TABLE 4d

Mutation of TSHR Arg255 to Asp

| | Cyclic AMP produced (fmol/cell well) (mean ± SD; n = 3) | | Mutated/Wild |
|---|---|---|---|
| | Wild type TSHR | Mutated TSHR | type (%) |
| Experiment 1 hMAb TSHR1 (ng/mL) | | | |
| 0.1 | 1124 ± 48 | 488 ± 60 | 43 |
| 0.3 | 2578 ± 152 | 478 ± 50 | 19 |
| 1 | 8950 ± 680 | 370 ± 150 | 4 |
| 3 | 14870 ± 2520 | 620 ± 110 | 4 |
| 10 | 13750 ± 1620 | 1440 ± 20 | 10 |
| TSH (ng/mL) | | | |
| 0.01 | 1110 ± 166 | 776 ± 94 | 70 |
| 0.03 | 1360 ± 210 | 1206 ± 54 | 89 |
| 0.1 | 3246 ± 594 | 2806 ± 586 | 86 |
| 0.3 | 8880 ± 800 | 8340 ± 350 | 94 |
| 1 | 10030 ± 2040 | 12400 ± 390 | 124 |
| 3 | 12260 ± 140 | 9980 ± 510 | 81 |
| Cyclic AMP assay buffer | 270 ± 84 | 170 ± 40 | |
| Experiment 2 hMAb TSHR1 (ng/mL) | | | |
| 0.1 | 1088 ± 88 | 374 ± 18 | 34 |
| 0.3 | 2250 ± 240 | 360 ± 30 | 16 |
| 1 | 5904 ± 620 | 154 ± 8 | 3 |
| 3 | 10604 ± 420 | 190 ± 4 | 2 |
| 10 | 17010 | 150 ± 20 | 1 |
| TSH (ng/mL) | | | |
| 0.01 | 516 ± 58 | 590 ± 148 | 114 |
| 0.03 | 1048 ± 320 | 908 ± 54 | 87 |
| 0.1 | 3788 ± 644 | 2382 ± 858 | 63 |
| 0.3 | 6906 ± 1090 | 9278 ± 1310 | 134 |
| 1 | 18284 ± 3660 | 9910 ± 1100 | 54 |
| 3 | 17370 | 16000 | 92 |
| Cyclic AMP assay buffer | 670 ± 548 | 424 ± 54 | |

TABLE 5

Summary of effect of mutations (relative to wild type) on stimulation of CHO cells containing mutated TSHR

| aa mutation | TSH stimulation | hMAb TSHR1 Fab stimulation |
|---|---|---|
| Gln235 to Ala | little effect | little effect |
| Thr237 to Ala | little effect | little effect |
| Arg255 to Asp | little effect | essentially abolished |
| Arg255 to Ala and Trp258 to Ala | little effect | essentially abolished |

TABLE 6

Stimulation of cyclic AMP production by 14 sera from patients with Graves' disease (G1-G14) in CHO cells expressing wild type TSHR and TSHR with Arg255 mutated to Asp

| | Cyclic AMP produced (fmol/cell well) mean ± SD (n = 3) | | Mutated/Wild |
|---|---|---|---|
| | Wild type TSHR | Mutated TSHR | type (%) |
| Experiment 1 | | | |
| Cyclic AMP assay buffer only | 520 ± 350 | 650 ± 4 | 125 |
| HBD pool | 570 ± 360 | 420 ± 360 | 74 |
| G1 | 11490 ± 1030 | 3840 ± 400 | 33 |
| G2 | 9250 ± 950 | 1420 ± 630 | 15 |
| G3 | 4590 ± 910 | 950 ± 240 | 21 |
| G4 | 7340 ± 370 | 750 ± 570 | 10 |
| G5 | 8480 ± 800 | 1390 ± 200 | 16 |
| G6 | 3820 ± 480 | 1140 ± 200 | 30 |
| G7 | 7880 ± 580 | 1680 ± 210 | 21 |
| G8 | 9310 ± 650 | 2530 ± 380 | 27 |
| TSH (3 ng/mL) | 10180 ± 640 | 12000 ± 1960 | 118 |
| hMAb TSHR1 Fab (10 ng/mL) | 12060 ± 1130 | 1860 ± 190 | 15 |
| Experiment 2 | | | |
| Cyclic AMP assay buffer only | 150 ± 20 | 340 ± 330 | 227 |
| HBD | 150[a] | 150 ± 10 | 100 |
| G9 | 12250 ± 1590 | 1470 ± 150 | 12 |
| G10 | 5880 ± 160 | 560 ± 350 | 10 |
| G11 | 1790 ± 230 | 340 ± 300 | 19 |
| G12 | 3290 ± 360 | 140[a] | 4 |
| G13 | 8580 ± 730 | 2160 ± 140 | 25 |
| G14 | 2750 ± 20 | 700 ± 80 | 25 |
| TSH (3 ng/mL) | 21130[a] | 20580 ± 2520 | 97 |
| hMAb TSHR1 Fab (10 ng/mL) | 19240 ± 2550 | 1510 ± 310 | 8 |

[a]mean of duplicate
HBD = pool of healthy blood donor sera.

TABLE 7

Stimulation of cyclic AMP production by different doses of hMAb TSHR1 IgG and the donor plasma[a] in CHO cells expressing wild type TSHR and TSHR with Arg255 mutated to Asp.

| Sample dilution or | Cyclic AMP produced (fmol/cell well) (mean ± SD; n = 3) | | Mutated/Wild |
|---|---|---|---|
| concentration[b] | Wild type TSHR | Mutated TSHR | type (%) |
| HBD/10 | 580 ± 180 | 270[c] | 47 |
| Cyclic AMP assay buffer only | 790 ± 180 | 450 ± 160 | 57 |
| TSH (3 ng/mL) | 19010 ± 2360 | 16120 ± 1230 | 85 |
| hMAb TSHR1 IgG | | | |
| 1 ng/mL | 4860 ± 720 | 940 ± 70 | 19 |
| 10 ng/mL | 16230 ± 230 | 3160 ± 380 | 19 |

TABLE 7-continued

Stimulation of cyclic AMP production by different doses of hMAb TSHR1 IgG and the donor plasma[a] in CHO cells expressing wild type TSHR and TSHR with Arg255 mutated to Asp.

| Sample dilution or concentration[b] | Cyclic AMP produced (fmol/cell well) (mean ± SD; n = 3) Wild type TSHR | Mutated TSHR | Mutated/Wild type (%) |
|---|---|---|---|
| 100 ng/mL | 15410 ± 1400 | 5700 ± 360 | 37 |
| 1 μg/mL | 16340 ± 3690 | 5030 ± 780 | 31 |
| Donor plasma dilution | | | |
| 2000x | 2400 ± 130 | 820 ± 120 | 34 |
| 1000x | 4180 ± 980 | 970 ± 240 | 23 |
| 200x | 11020 ± 900 | 1790 ± 240 | 16 |
| 100x | 14860 ± 1560 | 2550 ± 530 | 17 |
| 20x | 15750 ± 1480 | 3160 ± 500 | 20 |

[a]The donor plasma was obtained from the same blood sample used to isolate lymphocytes for the preparation of the hMAb TSHR1 hybridoma
[b]Samples diluted in cyclic AMP assay buffer
[c]mean of duplicate
HBD = pool of healthy blood donor sera

TABLE 8

Stimulation of cyclic AMP production by 6 different mouse thyroid stimulating monoclonal antibodies (mTSMAbs) in CHO cells expressing wild type TSHR and TSHR with Arg255 mutated to Asp

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 502 ± 76 | 456 ± 30 | 91 |
| hMAb TSHR1 (10 ng/mL) | 18220 ± 1210 | 1160 ± 150 | 6 |
| 2G2 (1 μg/mL) | 524 ± 22 | 540 ± 20 | 103 |
| TSMAb 1 (1 μg/mL) | 4810 ± 1250 | 1740 ± 170 | 36 |
| TSMAb 2 (1 μg/mL) | 3440 ± 420 | 860 ± 90 | 25 |
| TSMAb C (10 ng/mL) | 9960 ± 1130 | 1490 ± 150 | 15 |
| TSMAb D (1 μg/mL) | 10850 ± 1340 | 1520 ± 170 | 14 |
| TSMAb E (1 μg/mL) | 2490 ± 160 | 640 ± 10 | 26 |
| TSMAb F (100 ng/mL) | 16200 ± 2680 | 2670 ± 110 | 16 |

[a]Test samples in cyclic AMP buffer
2G2 is a mouse monoclonal antibody to thyroglobulin (negative control)

TABLE 9

TSH induced cyclic AMP production in CHO cells expressing wild type TSHR and TSHR with Arg255 mutated to Asp. Effect of 4 sera (B1-B4) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer | 936 ± 336 | 636 ± 86 | 68 |
| TSH[b] | 9550 ± 740 | 9580 ± 840 | 100 |
| HBD | 610 ± 84 | 514 ± 34 | 84 |
| HBD + TSH[b] | 8510 ± 590 | 5070 ± 720 | 60 |
| B1 | 390 ± 92 | 496 ± 90 | 127 |
| B1 + TSH[b] | 740 ± 590 | 520 ± 150 | 70 |
| B2 | 408 ± 30 | 408 ± 172 | 100 |
| B2 + TSH[b] | 240 ± 20 | 440 ± 140 | 183 |
| B3 | 504 ± 20 | 522 ± 96 | 104 |
| B3 + TSH[b] | 320 ± 60 | 550 ± 310 | 172 |

TABLE 9-continued

TSH induced cyclic AMP production in CHO cells expressing wild type TSHR and TSHR with Arg255 mutated to Asp. Effect of 4 sera (B1-B4) with TSH antagonist activity

| | | | |
|---|---|---|---|
| B4 | 414 ± 326 | 474 ± 12 | 114 |
| B4 + TSH[b] | 1180 ± 430 | 690 ± 340 | 58 |

B % inhibition results

| Serum with TSH antagonist activity | % inhibition of TSH stimulation[c] Wild type TSHR | Mutated TSHR |
|---|---|---|
| B1 | 91 | 90 |
| B2 | 97 | 91 |
| B3 | 96 | 89 |
| B4 | 86 | 86 |

HBD = Pool of healthy blood donor sera
[a]Test samples in cyclic AMP assay buffer; all sera were assayed at a final dilution of 10×
[b]TSH final concentration = 0.3 ng/mL $$^{c}\% \text{ inhibition} = 100 \times \left(1 - \frac{\text{cAMP in presence of TSH plus serum B1, B2, B3 or B4}}{\text{cAMP in presence of TSH plus HBD}}\right)$$

TABLE 10

TSH induced cyclic AMP production in CHO cells expressing wild type TSHR and TSHR with Arg255 mutated to Asp. Effect of different dilutions of serum B3 (Table 9) with TSH antagonist activity A Cyclic AMP levels

| Test sample dilution[a] | Cyclic AMP produced (fmol/cell well) (mean ± SD; n = 3) Wild type TSHR | Mutated TSHR | Mutated/Wild type (%) |
|---|---|---|---|
| B3 1000× | 718 ± 68 | 462 ± 80 | 64 |
| B3 1000× + TSH[c] | 11650 ± 710 | 3710 ± 570 | 32 |
| B3 100× | 626 ± 50 | 228 ± 24 | 36 |
| B3 100× + TSH[c] | 7590 ± 480 | 180 ± 20 | 2 |
| B3 10× | 358 ± 46 | 190 ± 20 | 53 |
| B3 10× + TSH[c] | 230 ± 98 | 310 ± 230 | 135 |
| HBD 1000× | 718[b] | 410 ± 22 | 57 |
| HBD 1000× + TSH[c] | 12210 ± 820 | 12594 ± 496 | 103 |
| HBD 100× | 768 ± 144 | 440 ± 62 | 57 |
| HBD 100× + TSH[c] | 9970 ± 800 | 10960 ± 750 | 110 |
| HBD 10× | 626 ± 106 | 346 ± 66 | 55 |
| HBD 10× + TSH[c] | 8130 ± 980 | 6920 ± 360 | 85 |

B % inhibition results

| Dilution of serum with TSH antagonist activity | % inhibition of TSH stimulation[d] Wild type TSHR | Mutated TSHR |
|---|---|---|
| B3 1000× | 5 | 70 |
| B3 100× | 24 | 98 |
| B3 10× | 97 | 96 |

HBD = Pool of healthy blood donor sera
[a]Test samples in cyclic AMP assay buffer
[b]mean of duplicate
[c]TSH final concentration = 0.3 ng/mL $$^{d}\% \text{ inhibition} = 100 \times \left(1 - \frac{\text{cAMP in presence of serum B3} + \text{TSH}}{\text{cAMP in presence of HBD} + \text{TSH}}\right)$$

where test sample and HBD dilutions are the same

TABLE 11

TSH induced cyclic AMP production in CHO cells expressing wild type TSHR and TSHR with Arg255 mutated to Asp. Effect of different dilutions of a monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 1208 ± 20 | 776 ± 344 | 64 |
| TSH[b] | 15410 ± 1450 | 12410 ± 3030 | 81 |
| 2G2 1 μg/mL + TSH[b] | 10890 ± 1130 | 10770 ± 1040 | 99 |
| 2G2 10 μg/mL + TSH[b] | 11580 ± 720 | 11540 ± 260 | 100 |
| 2G2 100 μg/mL + TSH[b] | 11710 ± 1890 | 10450 ± 1140 | 89 |
| 9D33 0.001 μg/mL + TSH[b] | 12960[c] | 11780 ± 750 | 91 |
| 9D33 0.01 μg/mL + TSH[b] | 11730 ± 220 | 11760 ± 940 | 100 |
| 9D33 0.1 μg/mL + TSH[b] | 9960 ± 520 | 5250 ± 610 | 53 |
| 9D33 1 μg/mL + TSH[b] | 7530 ± 1150 | 1160 ± 140 | 15 |
| 9D33 10 μg/mL + TSH[b] | 2560 ± 1470 | 700 ± 220 | 27 |
| 9D33 100 μg/mL + TSH[b] | 1180 ± 70 | 490 ± 80 | 42 |
| 9D33 100 μg | 1178 ± 60 | 558 ± 216 | 47 |

B % inhibition results

| Antibody concentration | % inhibition of TSH stimulation[d] Wild type TSHR | Mutated TSHR |
|---|---|---|
| 2G2 1 μg/mL | 29 | 13 |
| 2G2 10 μg/mL | 25 | 7 |
| 2G2 100 μg/mL | 24 | 16 |
| 9D33 0.001 μg/mL | 16 | 5 |
| 9D33 0.01 μg/mL | 24 | 5 |
| 9D33 0.1 μg/mL | 35 | 58 |
| 9D33 1 μg/mL | 51 | 91 |
| 9D33 10 μg/mL | 83 | 94 |
| 9D33 100 μg/mL | 92 | 96 |

[a]Test samples in cyclic AMP assay buffer

[b]TSH final concentration = 0.3 ng/mL

[c]mean of duplicate $$^{d}\%\ \text{inhibition} = 100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 12

Scatchard analysis of TSH and hMAb TSHR1 Fab binding to wild type (non-mutated) and mutated TSH receptor preparations

| Receptor preparation | Affinity for TSH | Affinity for hMAb TSHR1 Fab |
|---|---|---|
| Wild type | $4.2 \pm 1.0 \times 10^{9}$ L/mol | $2.9 \pm 0.6 \times 10^{10}$ L/mol |
| Asp43 mutated to Ala | $3.1 \times 10^{9}$ L/mol | $3.0 \times 10^{10}$ L/mol |
| Glu61 mutated to Ala | $2.7 \times 10^{9}$ L/mol | $2.9 \times 10^{10}$ L/mol |
| Glu157 mutated to Ala | TSH binding undetectable | $1.9 \times 10^{10}$ L/mol |
| Glu178 mutated to Ala | $0.9 \times 10^{9}$ L/mol | $0.6 \times 10^{10}$ L/mol |
| Asp203 mutated to Ala | $1.9 \times 10^{9}$ L/mol | $1.6 \times 10^{10}$ L/mol |
| Asp232 mutated to Ala | TSH binding undetectable | hMAb TSHR1 Fab binding undetectable |
| Arg255 mutated to Ala | $1.9 \times 10^{9}$ L/mol | $0.5 \times 10^{10}$ L/mol |
| Trp258 mutated to Ala | TSH binding undetectable | $1.0 \times 10^{10}$ L/mol |
| Asp276 mutated to Ala | $3.4 \times 10^{9}$ L/mol | $1.6 \times 10^{10}$ L/mol |
| Ser281 mutated to Ala | $3.4 \times 10^{9}$ L/mol | $2.3 \times 10^{10}$ L/mol |

TABLE 13a

TSH induced cyclic AMP production in CHO cells expressing wild type TSHR and TSHR with Asp43 mutated to Ala. Effect of different dilutions of a monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 84 ± 13 | 128 ± 20 | 152 |
| TSH | 7142 ± 389 | 6858 ± 2398 | 96 |
| 2G2 1 μg/mL + TSH[b] | 6631 ± 226 | 6854[c] | 103 |
| 2G2 10 μg/mL + TSH[b] | 7928 ± 1448 | 7876 ± 343 | 99 |
| 2G2 100 μg/mL + TSH[b] | 6011 ± 642 | 7572 ± 196 | 126 |
| 9D33 0.001 μg/mL + TSH[b] | 5670 ± 1727 | 5989 ± 366 | 106 |
| 9D33 0.01 μg/mL + TSH[b] | 6809 ± 411 | 6160[c] | 90 |
| 9D33 0.1 μg/mL + TSH[b] | 4958 ± 1852 | 5462 ± 467 | 110 |
| 9D33 1 μg/mL + TSH[b] | 1636 ± 226 | 1851 ± 314 | 113 |
| 9D33 10 μg/mL + TSH[b] | 1388 ± 416 | 1175 ± 116 | 85 |
| 9D33 100 μg/mL + TSH[b] | 681 ± 258 | 863 ± 192 | 127 |
| 9D33 100 μg | 1097 ± 362 | 107 ± 16 | 10 |

TABLE 13a-continued

TSH induced cyclic AMP production in CHO cells expressing wild type TSHR and TSHR with Asp43 mutated to Ala. Effect of different dilutions of a monoclonal antibody to the TSH receptor (9D33) with TSH antagonist activity B % inhibition results

| Antibody concentration | % inhibition of TSH stimulation[d] Wild type TSHR | Mutated TSHR |
|---|---|---|
| 2G2 1 μg/mL | 7 | 0 |
| 2G2 10 μg/mL | −11 | −15 |
| 2G2 100 μg/mL | 16 | −10 |
| 9D33 0.001 μg/mL | 21 | 13 |
| 9D33 0.01 μg/mL | 5 | 10 |
| 9D33 0.1 μg/mL | 31 | 20 |
| 9D33 1 μg/mL | 77 | 73 |
| 9D33 10 μg/mL | 81 | 83 |
| 9D33 100 μg/mL | 90 | 87 |

[a]Test samples in cyclic AMP assay buffer
[b]TSH final concentration = 0.5 ng/mL
[c]mean of duplicate $$^{d}\%\ \text{inhibition} = 100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 13b

TSH induced cyclic AMP production in CHO cells expressing wild type TSHR and TSHR with Glu61 mutated to Ala. Effect of different dilutions of a monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 154 ± 16 | 113 ± 35 | 86 |
| TSH | 15616 ± 3992 | 12824 ± 651 | 82 |
| 2G2 1 μg/mL + TSH[b] | 10613 ± 1188 | 15077 ± 2841 | 142 |
| 2G2 10 μg/mL + TSH[b] | 9163[c] | 12327[c] | 135 |
| 2G2 100 μg/mL + TSH[b] | 12967[c] | 14982 ± 908 | 116 |
| 9D33 0.001 μg/mL + TSH[b] | 11478 ± 1868 | 14708 ± 1441 | 128 |
| 9D33 0.01 μg/mL + TSH[b] | 12543[c] | 16118 ± 2133 | 129 |
| 9D33 0.1 μg/mL + TSH[b] | 13098 ± 253 | 7695 ± 3489 | 59 |
| 9D33 1 μg/mL + TSH[b] | 3249 ± 162 | 3960 ± 232 | 122 |
| 9D33 10 μg/mL + TSH[b] | 1819 ± 609 | 2800 ± 201 | 154 |
| 9D33 100 μg/mL + TSH[b] | 625 ± 27 | 1679 ± 546 | 269 |
| 9D33 100 μg | 87 ± 43 | nd | nd |

B % inhibition results

| Antibody concentration | % inhibition of TSH stimulation[d] Wild type TSHR | Mutated TSHR |
|---|---|---|
| 2G2 1 μg/mL | 32 | −18 |
| 2G2 10 μg/mL | 41 | 4 |
| 2G2 100 μg/mL | 17 | −17 |
| 9D33 0.001 μg/mL | 26 | −15 |

TABLE 13b-continued

TSH induced cyclic AMP production in CHO cells expressing wild type TSHR and TSHR with Glu61 mutated to Ala. Effect of different dilutions of a monoclonal antibody to the TSH receptor (9D33) with TSH antagonist activity

| | | |
|---|---|---|
| 9D33 0.01 μg/mL | 20 | −26 |
| 9D33 0.1 μg/mL | 16 | 40 |
| 9D33 1 μg/mL | 79 | 69 |
| 9D33 10 μg/mL | 88 | 78 |
| 9D33 100 μg/mL | 96 | 87 |

[a]Test samples in cyclic AMP assay buffer
[b]TSH final concentration = 0.5 ng/mL
[c]mean of duplicate $$^{d}\%\ \text{inhibition} = 100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)
nd = not determined TABLE 13c TSH induced cyclic AMP production in CHO cells expressing wild type TSHR and TSHR with Glu178 mutated to Ala. Effect of different dilutions of a monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 122 ± 25 | ud | nd |
| TSH | 6162 ± 458 | 4613[c] | 75 |
| 2G2 1 μg/mL + TSH[b] | 5070 ± 271 | 5825[c] | 115 |
| 2G2 10 μg/mL + TSH[b] | 4493[c] | nd | nd |
| 2G2 100 μg/mL + TSH[b] | 4468 ± 1019 | 4083 ± 1170 | 91 |
| 9D33 0.001 μg/mL + TSH[b] | 2784 ± 625 | 4062 ± 637 | 146 |
| 9D33 0.01 μg/mL + TSH[b] | 3255 ± 124 | 4476 ± 1383 | 138 |
| 9D33 0.1 μg/mL + TSH[b] | 3439 ± 147 | 1886 ± 396 | 55 |
| 9D33 1 μg/mL + TSH[b] | 754 ± 372 | 540 ± 303 | 72 |
| 9D33 10 μg/mL + TSH[b] | 774 ± 99 | 519 ± 135 | 67 |
| 9D33 100 μg/mL + TSH[b] | 654 ± 115 | 395 ± 241 | 60 |
| 9D33 100 μg | 83 ± 42 | 34 ± 7 | 41 |

B % inhibition results

| Antibody concentration | % inhibition of TSH stimulation[d] Wild type TSHR | Mutated TSHR |
|---|---|---|
| 2G2 1 μg/mL | 18 | −26 |
| 2G2 10 μg/mL | 27 | nd |
| 2G2 100 μg/mL | 27 | 11 |
| 9D33 0.001 μg/mL | 55 | 12 |
| 9D33 0.01 μg/mL | 53 | 3 |
| 9D33 0.1 μg/mL | 44 | 59 |
| 9D33 1 μg/mL | 88 | 88 |

TABLE 13c-continued

TSH induced cyclic AMP production in CHO cells expressing wild type TSHR and TSHR with Glu178 mutated to Ala. Effect of different dilutions of a monoclonal antibody to the TSH receptor (9D33) with TSH antagonist activity

| | | |
|---|---|---|
| 9D33 10 μg/mL | 87 | 89 |
| 9D33 100 μg/mL | 89 | 91 |

[a]Test samples in cyclic AMP assay buffer
[b]TSH final concentration = ng/mL
[c]mean of duplicate $$^{d}\%\ \text{inhibition} = 100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)
ud = undetectable
nd = not determined TABLE 13d TSH induced cyclic AMP production in CHO cells expressing wild type TSHR and TSHR with Asp203 mutated to Ala. Effect of different dilutions of a monoclonal antibody to the TSH receptor (9D33) with TSH antagonist activity A Cyclic AMP levels

| | Cyclic AMP produced (fmol/cell well) (mean ± SD; n = 3) | | |
|---|---|---|---|
| Test sample[a] | Wild type TSHR | Mutated TSHR | Mutated/Wild type (%) |
| Cyclic AMP assay buffer only | 140 ± 11 | 134[c] | 96 |
| TSH | 6227 ± 1211 | 6167 ± 923 | 99 |
| 2G2 1 μg/mL + TSH[b] | 4307 ± 553 | 6428[c] | 149 |
| 2G2 10 μg/mL + TSH[b] | 5579 ± 1128 | 4708 ± 908 | 84 |
| 2G2 100 μg/mL + TSH[b] | 6920 ± 1455 | 5204 ± 787 | 75 |
| 9D33 0.001 μg/mL + TSH[b] | 4916 ± 405 | 5093 ± 581 | 104 |
| 9D33 0.01 μg/mL + TSH[b] | 4600 ± 394 | 5671 ± 1164 | 123 |
| 9D33 0.1 μg/mL + TSH[b] | 3814 ± 342 | 2905 ± 295 | 76 |
| 9D33 1 μg/mL + TSH[b] | 760 ± 315 | 1322 ± 125 | 174 |
| 9D33 10 μg/mL + TSH[b] | 466[c] | 498 ± 97 | 107 |
| 9D33 100 μg/mL + TSH[b] | 171[c] | 275 ± 27 | 161 |
| 9D33 100 μg | 159 ± 22 | 151 ± 23 | 95 |

B % inhibition results

| | % inhibition of TSH stimulation[d] | |
|---|---|---|
| Antibody concentration | Wild type TSHR | Mutated TSHR |
| 2G2 1 μg/mL | 31 | −4 |
| 2G2 10 μg/mL | 10 | 24 |
| 2G2 100 μg/mL | −11 | 16 |
| 9D33 0.001 μg/mL | 21 | 17 |
| 9D33 0.01 μg/mL | 26 | 8 |
| 9D33 0.1 μg/mL | 39 | 53 |
| 9D33 1 μg/mL | 88 | 79 |

TABLE 13d-continued

TSH induced cyclic AMP production in CHO cells expressing wild type TSHR and TSHR with Asp203 mutated to Ala. Effect of different dilutions of a monoclonal antibody to the TSH receptor (9D33) with TSH antagonist activity

| | | |
|---|---|---|
| 9D33 10 μg/mL | 93 | 92 |
| 9D33 100 μg/mL | 97 | 96 |

[a]Test samples in cyclic AMP assay buffer
[b]TSH final concentration = 0.3 ng/mL
[c]mean of duplicate $$^{d}\%\ \text{inhibition} = 100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 13e

TSH induced cyclic AMP production in CHO cells expressing wild type TSHR and TSHR with Gln235 mutated to Ala. Effect of different dilutions of a monoclonal antibody to the TSH receptor (9D33) with TSH antagonist activity A Cyclic AMP levels

| | Cyclic AMP produced (fmol/cell well) (mean ± SD; n = 3) | | |
|---|---|---|---|
| Test sample[a] | Wild type TSHR | Mutated TSHR | Mutated/Wild type (%) |
| Cyclic AMP assay buffer only | 524[c] | 141[c] | 27 |
| TSH | 12503 ± 1060 | 11847 ± 689 | 95 |
| 2G2 1 μg/mL + TSH[b] | 12569 ± 1992 | 13130[c] | 104 |
| 2G2 10 μg/mL + TSH[b] | 14948 ± 1044 | 11648 ± 723 | 78 |
| 2G2 100 μg/mL + TSH[b] | 12514 ± 2316 | 11909 ± 533 | 95 |
| 9D33 0.001 μg/mL + TSH[b] | 10756 ± 1623 | 12067[c] | 112 |
| 9D33 0.01 μg/mL + TSH[b] | 13418 ± 1640 | 14843 ± 2529 | 111 |
| 9D33 0.1 μg/mL + TSH[b] | 11906 ± 1805 | 11792 ± 898 | 99 |
| 9D33 1 μg/mL + TSH[b] | 10325 ± 816 | 10567 ± 685 | 102 |
| 9D33 10 μg/mL + TSH[b] | 8185[c] | 4368[c] | 53 |
| 9D33 100 μg/mL + TSH[b] | 6127 ± 166 | 2171[c] | 35 |
| 9D33 100 μg | 156 ± 8 | 499 ± 37 | 320 |

B % inhibition results

| | % inhibition of TSH stimulation[d] | |
|---|---|---|
| Antibody concentration | Wild type TSHR | Mutated TSHR |
| 2G2 1 μg/mL | −1 | −11 |
| 2G2 10 μg/mL | −20 | 2 |
| 2G2 100 μg/mL | 0 | −1 |
| 9D33 0.001 μg/mL | 14 | −2 |
| 9D33 0.01 μg/mL | −7 | −25 |
| 9D33 0.1 μg/mL | 5 | 0 |
| 9D33 1 μg/mL | 17 | 11 |

TABLE 13e-continued

TSH induced cyclic AMP production in CHO cells expressing wild type TSHR and TSHR with Gln235 mutated to Ala. Effect of different dilutions of a monoclonal antibody to the TSH receptor (9D33) with TSH antagonist activity

| | | |
|---|---|---|
| 9D33 10 μg/mL | 35 | 63 |
| 9D33 100 μg/mL | 51 | 82 |

[a]Test samples in cyclic AMP assay buffer
[b]TSH final concentration = ng/mL
[c]mean of duplicate $$^{d}\% \text{ inhibition} = 100 \times \left(1 - \frac{\text{cAMP in presence of test sample + TSH}}{\text{cAMP in presence of cyclic AMP assay buffer + TSH}}\right)$$

2G2 is a mouse monoclonal antibody to thyroglobulin (negative control for 9D33)

TABLE 13f

TSH induced cyclic AMP production in CHO cells expressing wild type TSHR and TSHR with Arg255 mutated to Ala. Effect of different dilutions of a monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 197 ± 34 | 325 ± 47 | 165 |
| TSH | 6871 ± 970 | 10822 ± 1435 | 158 |
| 2G2 1 μg/mL + TSH[b] | 6407 ± 1141 | 11502 ± 2692 | 180 |
| 2G2 10 μg/mL + TSH[b] | 5803 ± 154 | 8806[c] | 152 |
| 2G2 100 μg/mL + TSH[b] | 8283 ± 1485 | 12027 ± 463 | 145 |
| 9D33 0.001 μg/mL + TSH[b] | 7451 ± 1473 | 12018 ± 2501 | 161 |
| 9D33 0.01 μg/mL + TSH[b] | 6528 ± 2277 | 11961 ± 1453 | 183 |
| 9D33 0.1 μg/mL + TSH[b] | 3019 ± 528 | 6107 ± 753 | 202 |
| 9D33 1 μg/mL + TSH[b] | 1765 ± 145 | 2858 ± 268 | 162 |
| 9D33 10 μg/mL + TSH[b] | 1369 ± 146 | 1873 ± 247 | 137 |
| 9D33 100 μg/mL + TSH[b] | 768 ± 158 | 1662 ± 177 | 216 |
| 9D33 100 μg/mL | 223 ± 19 | 402 ± 57 | 180 |

B % inhibition results

| Antibody concentration | % inhibition of TSH stimulation[d] Wild type TSHR | Mutated TSHR |
|---|---|---|
| 2G2 1 μg/mL | 7 | −6 |
| 2G2 10 μg/mL | 16 | 19 |
| 2G2 100 μg/mL | −21 | −11 |
| 9D33 0.001 μg/mL | −8 | −11 |
| 9D33 0.01 μg/mL | 5 | −11 |
| 9D33 0.1 μg/mL | 56 | 44 |
| 9D33 1 μg/mL | 74 | 74 |
| 9D33 10 μg/mL | 80 | 83 |
| 9D33 100 μg/mL | 89 | 85 |

[a]Test samples in cyclic AMP assay buffer
[b]TSH final concentration = 0.3 ng/mL
[c]mean of duplicate
[d]% inhibition =

$$100 \times \left(1 - \frac{\text{cAMP in presence of test sample + TSH}}{\text{cAMP in presence of cyclic AMP assay buffer + TSH}}\right)$$

2G2 is a mouse monoclonal antibody to thyroglobulin (negative control for 9D33)

TABLE 13g

TSH induced cyclic AMP production in CHO cells expressing wild type TSHR and TSHR with Thr257 mutated to Ala. Effect of different dilutions of a monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 365 ± 40 | 410 ± 82 | 112 |
| TSH | 4491[c] | 4179 ± 281 | 93 |
| 2G2 1 μg/mL + TSH[b] | 3900 ± 124 | 3723 ± 344 | 95 |
| 2G2 10 μg/mL + TSH[b] | 4478 ± 153 | 3549 ± 199 | 79 |
| 2G2 100 μg/mL + TSH[b] | 4038 ± 549 | 4191 ± 686 | 104 |
| 9D33 0.001 μg/mL + TSH[b] | 4400 ± 672 | 3655 ± 244 | 83 |
| 9D33 0.01 μg/mL + TSH[b] | 3301 ± 114 | 3796 ± 372 | 115 |
| 9D33 0.1 μg/mL + TSH[b] | 2804 ± 474 | 2225 ± 45 | 79 |
| 9D33 1 μg/mL + TSH[b] | 1256 ± 227 | 1486 ± 217 | 118 |
| 9D33 10 μg/mL + TSH[b] | 536[c] | 598[c] | 112 |
| 9D33 100 μg/mL + TSH[b] | 435 ± 19 | 523 ± 53 | 120 |
| 9D33 100 μg | 356 ± 11 | 457[c] | 128 |

B % inhibition results

| Antibody concentration | % inhibition of TSH stimulation[d] Wild type TSHR | Mutated TSHR |
|---|---|---|
| 2G2 1 μg/mL | 13 | 11 |
| 2G2 10 μg/mL | 0 | 15 |
| 2G2 100 μg/mL | 10 | 0 |
| 9D33 0.001 μg/mL | 2 | 13 |
| 9D33 0.01 μgImL | 26 | 9 |
| 9D33 0.1 μg/mL | 38 | 47 |
| 9D33 1 μg/mL | 72 | 64 |
| 9D33 10 μg/mL | 88 | 86 |
| 9D33 100 μg/mL | 90 | 87 |

[a]Test samples in cyclic AMP assay buffer
[b]TSH final concentration = 0.3 ng/mL
[c]mean of duplicate
[d]% inhibition =

$$100 \times \left(1 - \frac{\text{cAMP in presence of test sample + TSH}}{\text{cAMP in presence of cyclic AMP assay buffer + TSH}}\right)$$

2G2 is a mouse monoclonal antibody to thyroglobulin (negative control for 9D33)

TABLE 13h

TSH induced cyclic AMP production in CHO cells expressing wild type TSHR and TSHR with Trp258 mutated to Ala. Effect of different dilutions of a monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 119 ± 13 | 154 ± 41 | 129 |
| TSH | 8836 ± 2375 | 8958 ± 703 | 101 |
| 2G2 1 μg/mL + TSH[b] | 7339 ± 1966 | 6244 ± 1452 | 85 |
| 2G2 10 μg/mL + TSH[b] | 5250 ± 626 | 7015 ± 758 | 134 |
| 2G2 100 μg/mL + TSH[b] | 7991 ± 3095 | 6842 ± 771 | 111 |

TABLE 13h-continued

| | | | |
|---|---|---|---|
| 9D33 0.001 μg/mL + TSH[b] | 9371 ± 1878 | 7449[c] | 79 |
| 9D33 0.01 μg/mL + TSH[b] | 7411 ± 1694 | 6123 ± 685 | 83 |
| 9D33 0.1 μg/mL + TSH[b] | 6379 ± 226 | 3435 ± 359 | 54 |
| 9D33 1 μg/mL + TSH[b] | 1893 ± 1164 | 1990 ± 197 | 105 |
| 9D33 10 μg/mL + TSH[b] | 1342 ± 451 | 1150 ± 84 | 86 |
| 9D33 100 μg/mL + TSH[b] | 689 ± 118 | 601 ± 17 | 87 |
| 9D33 100 μg | 179 ± 11 | 117 ± 25 | 65 |

B % inhibition results

| | % inhibition of TSH stimulation[d] | |
|---|---|---|
| Antibody concentration | Wild type TSHR | Mutated TSHR |
| 2G2 1 μg/mL | 17 | 30 |
| 2G2 10 μg/mL | 41 | 22 |
| 2G2 100 μg/mL | 10 | 1 |
| 9D33 0.001 μg/mL | −6 | 17 |
| 9D33 0.01 μg/mL | 16 | 32 |
| 9D33 0.1 μg/mL | 28 | 62 |
| 9D33 1 μg/mL | 79 | 78 |
| 9D33 10 μg/mL | 85 | 87 |
| 9D33 100 μg/mL | 92 | 93 |

[a]Test samples in cyclic AMP assay buffer
[b]TSH final concentration = 0.3 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 13i

TSH induced cyclic AMP production in CHO cells expressing wild type TSHR and TSHR with Ser281 mutated to Ala. Effect of different dilutions of a monoclonal antibody to the TSH receptor (9D33) with TSH antagonist activity A Cyclic AMP levels

| | Cyclic AMP produced (fmol/cell well) (mean ± SD; n = 3) | | Mutated/ |
|---|---|---|---|
| Test sample[a] | Wild type TSHR | Mutated TSHR | Wild type (%) |
| Cyclic AMP assay buffer only | 94 ± 4 | 173 ± 58 | 184 |
| TSH | 4846 ± 620 | 9761 ± 4189 | 201 |
| 2G2 1 μg/mL + TSH[b] | 4887 ± 1492 | 7017[c] | 144 |
| 2G2 10 μg/mL + TSH[b] | 5206[c] | 6929 ± 1601 | 133 |
| 2G2 100 μg/mL + TSH[b] | 5128 ± 1801 | 13529 ± 2725 | 264 |
| 9D33 0.001 μg/mL + TSH[b] | 6502 ± 2731 | 5846 ± 613 | 90 |
| 9D33 0.01 μg/mL + TSH[b] | 4502 ± 716 | 7709 ± 1418 | 171 |
| 9D33 0.1 μg/mL + TSH[b] | 4745 ± 290 | 4119 ± 1045 | 87 |
| 9D33 1 μg/mL + TSH[b] | 1994 ± 361 | 1973 ± 45 | 99 |
| 9D33 10 μg/mL + TSH[b] | 1184 ± 136 | 1143 ± 322 | 97 |
| 9D33 100 μg/mL + TSH[b] | 1332 ± 469 | 1066 ± 319 | 80 |
| 9D33 100 μg | 186 ± 15 | 172 ± 24 | 92 |

B % inhibition results

| | % inhibition of TSH stimulation[d] | |
|---|---|---|
| Antibody concentration | Wild type TSHR | Mutated TSHR |
| 2G2 1 μg/mL | −1 | 28 |
| 2G2 10 μg/mL | −7 | 29 |
| 2G2 100 μg/mL | −6 | −39 |
| 9D33 0.001 μg/mL | −34 | 40 |

TABLE 13i-continued

| | | |
|---|---|---|
| 9D33 0.01 μg/mL | 7 | 21 |
| 9D33 0.1 μg/mL | 2 | 58 |
| 9D33 1 μg/mL | 59 | 80 |
| 9D33 10 μg/mL | 76 | 88 |
| 9D33 100 μg/mL | 73 | 89 |

[a]Test samples in cyclic AMP assay buffer
[b]TSH final concentration = 0.3 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 13j

TSH induced cyclic AMP production in CHO cells expressing wild type TSHR and TSHR with Arg255 mutated to Ala and Trp258 mutated to Ala. Effect of different dilutions of a monoclonal antibody to the TSH receptor (9D33) with TSH antagonist activity A Cyclic AMP levels

| | Cyclic AMP produced (fmol/cell well) (mean ± SD; n = 3) | | Mutated/ |
|---|---|---|---|
| Test sample[a] | Wild type TSHR | Mutated TSHR | Wild type (%) |
| Cyclic AMP assay buffer only | 876 ± 26 | 536 ± 108 | 61 |
| TSH | 11487 ± 683 | 6935 ± 796 | 60 |
| 2G2 1 μg/mL + TSH[b] | 9762 ± 684 | 7202 ± 334 | 74 |
| 2G2 10 μg/mL + TSH[b] | 9374 ± 1023 | 6369 ± 33 | 68 |
| 2G2 100 μg/mL + TSH[b] | 12285 ± 1718 | 6513 ± 254 | 53 |
| 9D33 0.001 μg/mL + TSH[b] | 8773 ± 1226 | 6741 ± 381 | 77 |
| 9D33 0.01 μg/mL + TSH[b] | 10499 ± 1934 | 5660 ± 157 | 54 |
| 9D33 0.1 μg/mL + TSH[b] | 7500 ± 336 | 1647 ± 197 | 22 |
| 9D33 1 μg/mL + TSH[b] | 3468 ± 548 | 643 ± 80 | 19 |
| 9D33 10 μg/mL + TSH[b] | 1243 ± 57 | 497 ± 132 | 40 |
| 9D33 100 μg/mL + TSH[b] | 1063 ± 163 | 189 ± 24 | 18 |
| 9D33 100 μg | 695 ± 33 | 386 ± 28 | 56 |

B % inhibition results

| | % inhibition of TSH stimulation[c] | |
|---|---|---|
| Antibody concentration | Wild type TSHR | Mutated TSHR |
| 2G2 1 μg/mL | 15 | −4 |
| 2G2 10 μg/mL | 18 | 8 |
| 2G2 100 μg/mL | −7 | 6 |
| 9D33 0.001 μg/mL | 24 | 3 |
| 9D33 0.01 μg/mL | 9 | 18 |
| 9D33 0.1 μg/mL | 35 | 76 |
| 9D33 1 μg/mL | 70 | 91 |
| 9D33 10 μg/mL | 89 | 93 |
| 9D33 100 μg/mL | 91 | 97 |

[a]Test samples in cyclic AMP assay buffer
[b]TSH final concentration = 0.3 ng/mL
[c]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 14

| Summary of effects of mutation (relative to wild type) on inhibition of TSH mediated cyclic AMP stimulation by the mouse monoclonal antibody 9D33 | |
|---|---|
| aa mutation | Inhibition of TSH mediated cyclic AMP stimulation by 9D33 |
| Asp43 to Ala | no effect |
| Glu61 to Ala | no effect |
| Glu178 to Ala | no effect |
| Asp203 to Ala | no effect |
| Gln235 to Ala | no effect |
| Arg255 to Ala | no effect |
| Arg255 to Asp | enhanced effect |
| Thr257 to Ala | no effect |
| Trp258 to Ala | no effect |
| Ser281 to Ala | no effect |
| Arg255 to Ala and Trp258 to Ala | no effect |

TABLE 15a

Effect of mutation of TSHR Lys58 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1410 ± 124 | 997 ± 132 | 71 |
| 0.3 | 1718 ± 381 | 1962 ± 135 | 114 |
| 1 | 3067 ± 270 | 8960 ± 1501 | 292 |
| 3 | 13569 ± 3730 | 6003 ± 242 | 44 |
| 10 | 16312 ± 1559 | 17808 ± 4348 | 109 |
| TSH (ng/ml) | | | |
| 0.01 | 1410 ± 124 | 1621 ± 162 | 115 |
| 0.03 | 2881 ± 684 | 3020 ± 443 | 105 |
| 0.1 | nd | nd | nd |
| 0.3 | 17623 ± 493 | 19584 ± 1889 | 111 |
| 1 | 15629 ± 2427 | 26367 ± 1861 | 169 |
| 3 | 16621 ± 1196 | 20053 ± 3738 | 121 |
| Cyclic AMP assay buffer | 377 ± 229 | 356 ± 122 | |
| Experiment 2 hMAb TSHR1 (ng/mL) | | | |
| 0.1 | 1206 ± 70 | 777 ± 75 | 64 |
| 0.3 | 2571 ± 130 | 1298 ± 121 | 50 |
| 1 | 6754 ± 1140 | 2948 ± 169 | 44 |
| 3 | 11485 ± 1262 | 7373 ± 197 | 64 |
| 10 | 12204 ± 1056 | 13538 ± 1409 | 111 |
| TSH (ng/mL) | | | |
| 0.01 | 675 ± 34 | 783 ± 57 | 116 |
| 0.03 | 1207 ± 251 | 1441 ± 175 | 119 |
| 0.1 | 3350 ± 326 | 3637 ± 245 | 109 |
| 0.3 | 9564 ± 785 | 8522 ± 335 | 89 |
| 1 | 12149 ± 73 | 14785 ± 1379 | 122 |
| 3 | 13701 ± 652 | 18020 ± 1527 | 132 |
| Cyclic AMP assay buffer | 429 ± 31 | 569 ± 23 | |

nd = not determined
hMAb TSHR1 Fab was used in all experiments

TABLE 15b

Effect of mutation of TSHR Ile60 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1432 ± 83 | 1574 ± 284 | 110 |
| 0.3 | 3834 ± 101 | 3060 ± 648 | 80 |
| 1 | 9355 ± 1170 | 6368 ± 673 | 68 |
| 3 | 17404 ± 2551 | 11276 ± 798 | 65 |
| 10 | 21898 ± 1209 | 22384 ± 3337 | 102 |
| TSH (ng/mL) | | | |
| 0.01 | 1106 ± 127 | 966 ± 72 | 87 |
| 0.03 | 1678 ± 37 | 1624 ± 166 | 97 |
| 0.1 | 5942[a] | 4550 ± 538 | 77 |
| 0.3 | 12023 ± 2060 | 9552 ± 846 | 79 |
| 1 | 18051 ± 1955 | 22768 ± 5454 | 126 |
| 3 | 24292 ± 1961 | 26734 ± 511 | 110 |
| Cyclic AMP assay buffer | 654 ± 19 | 857 ± 76 | |
| Experiment 2 hMAb TSHR1 (ng/mL) | | | |
| 0.1 | 1537 ± 223 | 1434 ± 115 | 93 |
| 0.3 | 3684 ± 149 | 2812 ± 192 | 76 |
| 1 | 9685 ± 723 | 7287 ± 833 | 81 |
| 3 | 17373 ± 656 | 12398 ± 775 | 71 |
| 10 | 20390[a] | 18968 ± 286 | 93 |
| TSH (ng/mL) | | | |
| 0.01 | 1104 ± 142 | 1191 ± 73 | 108 |
| 0.03 | 1699 ± 80 | 2014 ± 338 | 119 |
| 0.1 | 4731 ± 167 | 4642 ± 328 | 98 |
| 0.3 | 12871 ± 1429 | 11634 ± 434 | 90 |
| 1 | 17341 ± 592 | 17668 ± 1213 | 102 |
| 3 | 22282 ± 1483 | 20934 ± 554 | 94 |
| Cyclic AMP assay buffer | 834 ± 97 | 879 ± 54 | |

[a]mean of duplicate
hMAb TSHR1 Fab was used in all experiments

TABLE 15c

Effect of mutation of TSHR Arg80 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1758 ± 502 | 719 ± 78 | 41 |
| 0.3 | 4283 ± 192 | 745 ± 55 | 17 |
| 1 | 11225 ± 673 | 465 ± 57 | 4 |
| 3 | 20033 ± 3422 | 443 ± 29 | 2 |
| 10 | 22299 ± 1244 | 1026 ± 350 | 5 |
| TSH (ng/mL) | | | |
| 0.01 | 1019 ± 238 | 1612 ± 720 | 158 |
| 0.03 | 2350 ± 1100 | 3372 ± 721 | 143 |
| 0.1 | 5650 ± 304 | 5902[a] | 104 |
| 0.3 | 12387 ± 3782 | 17557 ± 4187 | 142 |
| 1 | 20052 ± 2829 | 20003 ± 2029 | 100 |
| 3 | 28631 ± 1464 | 17696 ± 3212 | 62 |
| Cyclic AMP assay buffer | 683 ± 19 | 676 ± 66 | |
| Experiment 2 hMAb TSHR1 (ng/mL) | | | |
| 0.1 | 2311 ± 631 | 1159 ± 214 | 50 |
| 0.3 | 4772 ± 930 | 1352 ± 404 | 28 |

TABLE 15c-continued

Effect of mutation of TSHR Arg80 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| 1 | 11729 ± 1421 | 1701 ± 19 | 15 |
| 3 | 19197 ± 6100 | 1714 ± 189 | 9 |
| 10 | 19820 ± 1443 | 1676 ± 293 | 8 |
| TSH (ng/mL) | | | |
| 0.01 | 1069 ± 227 | 1375 ± 136 | 129 |
| 0.03 | 2810 ± 539 | 3133 ± 292 | 111 |
| 0.1 | nd | 5894[a] | nd |
| 0.3 | 14592 ± 1531 | 13199 ± 2744 | 90 |
| 1 | 23710 ± 1972 | 19145 ± 1820 | 81 |
| 3 | 26019 ± 4795 | 21095 ± 3355 | 81 |
| Cyclic AMP assay buffer | 594 ± 38 | 1194 ± 231 | |

[a]mean of duplicate nd = not determined hMAb TSHR1 Fab was used in all experiments TABLE 15d Effect of mutation of TSHR Arg80 to Asp on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1153 ± 19 | 940 ± 157 | 82 |
| 0.3 | 1933 ± 194 | 923 ± 19 | 48 |
| 1 | 5567 ± 1067 | 895 ± 66 | 16 |
| 3 | 11325 ± 1045 | 1031 ± 87 | 9 |
| 10 | 18903 ± 3034 | 863 ± 127 | 5 |
| TSH (ng/mL) | | | |
| 0.01 | 1015 ± 71 | 1015 ± 163 | 100 |
| 0.03 | 1620 ± 309 | 1379 ± 58 | 85 |
| 0.1 | 3470 ± 271 | 2301 ± 96 | 66 |
| 0.3 | 8692 ± 455 | 7790 ± 203 | 90 |
| 1 | 17173 ± 1433 | 9859 ± 744 | 57 |
| 3 | 19360 ± 1243 | 14095 ± 1426 | 73 |
| Cyclic AMP assay buffer | 671 ± 69 | 1098 ± 66 | |
| Experiment 2 hMAb TSHR1 (ng/mL) | | | |
| 0.1 | 728 ± 54 | 1029 ± 122 | 141 |
| 0.3 | 1435 ± 135 | 807 ± 70 | 56 |
| 1 | 6506 ± 317 | 855 ± 344 | 13 |
| 3 | 9982 ± 1363 | 1089 ± 225 | 11 |
| 10 | 24283 ± 6165 | 649 ± 346 | 3 |
| TSH (ng/mL) | | | |
| 0.01 | 815 ± 69 | 1015 ± 126 | 125 |
| 0.03 | 1088 ± 116 | 1962 ± 137 | 180 |
| 0.1 | 3291 ± 424 | 4496 ± 47 | 137 |
| 0.3 | 6511 ± 785 | 11286 ± 2733 | 173 |
| 1 | 13663 ± 1309 | 13474 ± 981 | 99 |
| 3 | 20084 ± 4514 | 15230 ± 3881 | 76 |
| Cyclic AMP assay buffer | 905 ± 258 | 785 ± 113 | |

hMAb TSHR1 Fab was used in all experiments

TABLE 15e

Effect of mutation of TSHR Tyr82 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1307 ± 198 | 1316 ± 177 | 100 |
| 0.3 | 2717 ± 99 | 1611 ± 225 | 59 |
| 1 | 7883 ± 576 | 2993 ± 741 | 38 |
| 3 | 11500 ± 1811 | 6786 ± 228 | 59 |
| 10 | 15890 ± 3356 | 10749 ± 1312 | 68 |
| TSH (ng/mL) | | | |
| 0.01 | 658 ± 164 | 1764 ± 110 | 268 |
| 0.03 | 1335 ± 162 | 2070[a] | 155 |
| 0.1 | 3567 ± 428 | 3932 ± 553 | 110 |
| 0.3 | 8610[a] | 8104 ± 723 | 94 |
| 1 | 13021[a] | 13821 ± 1198 | 106 |
| 3 | 18076 ± 5118 | 15070 ± 2214 | 83 |
| Cyclic AMP assay buffer | 432 ± 53 | 914 ± 87 | |
| Experiment 2 hMAb TSHR1 (ng/mL) | | | |
| 0.1 | 1393 ± 27 | 1075 ± 85 | 77 |
| 0.3 | 3709 ± 434 | 1511 ± 140 | 41 |
| 1 | 7756 ± 918 | 3507 ± 455 | 42 |
| 3 | 13197 ± 2052 | 6528 ± 202 | 49 |
| 10 | 18635 ± 1877 | 9085[a] | 49 |
| TSH (ng/mL) | | | |
| 0.01 | 861 ± 83 | 1047 ± 74 | 122 |
| 0.03 | 1390 ± 181 | 1535 ± 234 | 110 |
| 0.1 | 3846 ± 303 | 3790 ± 288 | 99 |
| 0.3 | 7900 ± 820 | 6400 ± 278 | 81 |
| 1 | 12747 ± 1290 | 9605 ± 642 | 75 |
| 3 | 15892 ± 125 | 16516[a] | 104 |
| Cyclic AMP assay buffer | 682 ± 97 | 697 ± 12 | |

[a]mean of duplicate hMAb TSHR1 Fab was used in all experiments

TABLE 15f

Effect of mutation of TSHR Glu107 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1814 ± 152 | 1135 ± 53 | 63 |
| 0.3 | 4032 ± 258 | 1096 ± 28 | 27 |
| 1 | 9770 ± 1020 | 985 ± 90 | 10 |
| 3 | 17529 ± 1597 | 1136 ± 65 | 6 |
| 10 | 22348 ± 3565 | 1760 ± 175 | 8 |
| TSH (ng/mL) | | | |
| 0.01 | 1161 ± 153 | 1160 ± 68 | 100 |
| 0.03 | 2010 ± 197 | 1469 ± 111 | 73 |
| 0.1 | 4433 ± 794 | 1906 ± 138 | 43 |
| 0.3 | 10299[a] | 3717 ± 283 | 36 |
| 1 | 18214 ± 1154 | 8438 ± 300 | 46 |
| 3 | 18540 ± 1065 | 14885 ± 2525 | 80 |
| Cyclic AMP assay buffer | 784 ± 38 | 1117 ± 57 | |
| Experiment 2 hMAb TSHR1 (ng/mL) | | | |
| 0.1 | 1417 ± 215 | 1331 ± 95 | 94 |
| 0.3 | 3190 ± 264 | 1259 ± 39 | 39 |

TABLE 15f-continued

Effect of mutation of TSHR Glu107 to Ala on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| 1 | 7438 ± 656 | 1053 ± 79 | 14 |
| 3 | 11470 ± 6099 | 1215[a] | 11 |
| 10 | 19199 ± 1545 | 1793 ± 280 | 9 |
| TSH (ng/mL) | | | |
| 0.01 | 1129 ± 64 | 1302 ± 118 | 115 |
| 0.03 | 1482 ± 246 | 1465[a] | 99 |
| 0.1 | 3788 ± 432 | 1996[a] | 53 |
| 0.3 | 8384 ± 643 | 4290 ± 120 | 51 |
| 1 | 12459[a] | 7910 ± 64 | 63 |
| 3 | 15288 ± 691 | 12050[a] | 79 |
| Cyclic AMP assay buffer | 416 ± 78 | 1057 ± 53 | |

[a]mean of duplicate hMAb TSHR1 Fab was used in all experiments

TABLE 15g

Effect of mutation of TSHR Glu107 to Arg on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| Experiment 1 hMAb TSHR1 (ng/mL) | | | |
| 0.1 | 500 ± 28 | 468 ± 129 | 94 |
| 0.3 | 1118 ± 133 | 350 ± 13 | 31 |
| 1 | 5204 ± 225 | ud | ud |
| 3 | 5424 ± 566 | ud | ud |
| 10 | 9834 ± 709 | ud | ud |
| TSH (ng/mL) | | | |
| 0.01 | 376 ± 13 | 488 ± 2 | 130 |
| 0.03 | 608 ± 122 | 488 ± 65 | 80 |
| 0.1 | 1960 ± 109 | 496 ± 100 | 25 |
| 0.3 | 3516 ± 154 | 440 ± 183 | 13 |
| 1 | 7114 ± 67 | 1020 ± 340 | 14 |
| 3 | 8384 ± 666 | 2176 ± 244 | 26 |
| Cyclic AMP assay buffer | 404 ± 54 | 412 ± 23 | |
| Experiment 2 hMAb TSHR1 (ng/mL) | | | |
| 0.1 | 682 ± 141 | 612 ± 69 | 90 |
| 0.3 | 1578 ± 294 | 650 ± 27 | 41 |
| 1 | 4592 ± 38 | 366 ± 71 | 8 |
| 3 | 6706 ± 420 | 430 ± 48 | 6 |
| 10 | 8858 ± 503 | 404 ± 26 | 5 |
| TSH (ng/mL) | | | |
| 0.01 | 712 ± 62 | 662 ± 92 | 93 |
| 0.03 | 1072 ± 120 | 670 ± 55 | 63 |
| 0.1 | 3680 ± 178 | 732 ± 115 | 20 |
| 0.3 | 6874 ± 79 | 572 ± 12 | 8 |
| 1 | 7652 ± 379 | 2038 ± 340 | 27 |
| 3 | 9250 ± 2392 | 3922 ± 650 | 42 |
| Cyclic AMP assay buffer | 410 ± 121 | 586 ± 24 | |

ud = undetectable hMAb TSHR1 Fab was used in all experiments

TABLE 15h

Effect of mutation of TSHR Arg109 to Ala on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| Experiment 1 hMAb TSHR1 (ng/mL) | | | |
| 0.1 | 2160 ± 121 | 1287 ± 154 | 60 |
| 0.3 | 5494 ± 360 | 1704 ± 136 | 31 |
| 1 | 14680 ± 475 | 3291 ± 230 | 22 |
| 3 | 20089 ± 1269 | 7588 ± 451 | 38 |
| 10 | 25202 ± 1926 | 17348[a] | 69 |
| TSH (ng/mL) | | | |
| 0.01 | 1436 ± 152 | 1486 ± 183 | 103 |
| 0.03 | 2355 ± 85 | 1886 ± 22 | 80 |
| 0.1 | nd | 4588 ± 395 | nd |
| 0.3 | 13613 ± 712 | 8503 ± 292 | 62 |
| 1 | 20552 ± 921 | 19037 ± 1144 | 93 |
| 3 | 24503 ± 1410 | 20440 ± 299 | 83 |
| Cyclic AMP assay buffer | 1070 ± 141 | 902 ± 141 | |
| Experiment 2 hMAb TSHR1 (ng/mL) | | | |
| 0.1 | 2090[a] | 1122 ± 169 | 54 |
| 0.3 | 3104 ± 544 | 1529 ± 65 | 49 |
| 1 | 8081 ± 834 | 4013 ± 733 | 50 |
| 3 | 17745 ± 1891 | 5641 ± 475 | 32 |
| 10 | 23838 ± 3352 | 11764 ± 385 | 49 |
| TSH (ng/mL) | | | |
| 0.01 | 1037[a] | 1632 ± 121 | 112 |
| 0.03 | 1709 ± 389 | 2063 ± 317 | 121 |
| 0.1 | 2634[a] | 3970 ± 165 | 151 |
| 0.3 | 9355 ± 1215 | 10053 ± 1175 | 107 |
| 1 | 17724 ± 1701 | 12994 ± 2273 | 73 |
| 3 | 24335 ± 4993 | 20831[a] | 86 |
| Cyclic AMP assay buffer | 739 ± 49 | 843 ± 85 | |

[a]mean of duplicate nd = not determined hMAb TSHR1 Fab was used in all experiments TABLE 15i Effect of mutation of TSHR Arg109 to Asp on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| Experiment 1 hMAb TSHR1 (ng/mL) | | | |
| 0.1 | 1372 ± 71 | 481 ± 32 | 35 |
| 0.3 | 2649 ± 369 | 512 ± 71 | 19 |
| 1 | 6840 ± 108 | 606 ± 41 | 9 |
| 3 | 12527 ± 1189 | 888 ± 68 | 7 |
| 10 | 17301 ± 1894 | 4140 ± 1000 | 24 |
| TSH (ng/mL) | | | |
| 0.01 | 993 ± 120 | 756 ± 174 | 76 |
| 0.03 | 1433 ± 74 | 1034 ± 171 | 72 |
| 0.1 | 2742 ± 32 | 1740 ± 114 | 63 |
| 0.3 | 8283 ± 48 | 4818 ± 252 | 59 |
| 1 | 15571 ± 1346 | 11540 ± 379 | 74 |
| 3 | 20509 ± 2613 | 14110 ± 1048 | 69 |
| Cyclic AMP assay buffer | 654 ± 72 | 481 ± 2 | |

TABLE 15i-continued

Effect of mutation of TSHR Arg109 to Asp on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| Experiment 2 hMAb TSHR1 (ng/mL) | | | |
| 0.1 | 1192 ± 136 | 388 ± 19 | 33 |
| 0.3 | 2890 ± 205 | 431 ± 95 | 15 |
| 1 | 7784 ± 989 | 510 ± 56 | 7 |
| 3 | 14298 ± 2299 | 989 ± 95 | 7 |
| 10 | 20908 ± 696 | 2922 ± 196 | 14 |
| TSH (ng/mL) | | | |
| 0.01 | 967 ± 108 | 487 ± 50 | 50 |
| 0.03 | 1084 ± 32 | 711 ± 77 | 66 |
| 0.1 | 4432 ± 558 | 1148 ± 101 | 26 |
| 0.3 | 6555 ± 763 | 3211 ± 103 | 49 |
| 1 | 17706 ± 1115 | 7377 ± 813 | 42 |
| 3 | 21807 ± 2198 | 13421 ± 966 | 62 |
| Cyclic AMP assay buffer | 570 ± 14 | 420 ± 79 | |

hMAb TSHR1 Fab was used in all experiments

TABLE 15j

Effect of mutation of TSHR Lys129 to Ala on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| Experiment 1 hMAb TSHR1 (ng/mL) | | | |
| 0.1 | 1536 ± 125 | 1320 ± 213 | 86 |
| 0.3 | 4391 ± 441 | 1270 ± 267 | 29 |
| 1 | 10466 ± 1641 | 2398 ± 427 | 23 |
| 3 | 16666 ± 476 | 4050 ± 125 | 24 |
| 10 | 23264 ± 1103 | 10349 ± 944 | 44 |
| TSH (ng/mL) | | | |
| 0.01 | 868 ± 138 | 1761 ± 184 | 203 |
| 0.03 | 1561 ± 349 | 2482 ± 294 | 159 |
| 0.1 | 4548 ± 269 | 4236 ± 548 | 93 |
| 0.3 | 8505 ± 119 | 11128 ± 1340 | 131 |
| 1 | 17249 ± 430 | 11396 ± 1457 | 66 |
| 3 | 17007[a] | 16021 ± 4948 | 94 |
| Cyclic AMP assay buffer | 1099 ± 8 | 1217 ± 80 | |
| Experiment 2 hMAb TSHR1 (ng/mL) | | | |
| 0.1 | 1631 ± 75 | 1475 ± 76 | 90 |
| 0.3 | 3811 ± 556 | 1768 ± 233 | 46 |
| 1 | 9073 ± 850 | 1821 ± 143 | 20 |
| 3 | 15292 ± 1346 | 5892 ± 650 | 39 |
| 10 | 20878 ± 2859 | 10467[a] | 50 |
| TSH (ng/mL) | | | |
| 0.01 | 1682 ± 59 | 1715 ± 273 | 102 |
| 0.03 | 2042 ± 116 | 2889 ± 393 | 141 |
| 0.1 | 5969 ± 369 | 5326[a] | 89 |
| 0.3 | 12989 ± 613 | 9891 ± 347 | 76 |
| 1 | 20148 ± 3038 | 15817[a] | 79 |
| 3 | 23202 ± 1348 | 20875 ± 1639 | 90 |
| Cyclic AMP assay buffer | 1168 ± 47 | 970 ± 257 | |

[a]mean of duplicate
hMAb TSHR1 Fab was used in all experiments

TABLE 15k

Effect of mutation of TSHR Lys129 to Asp on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| Experiment 1 hMAb TSHR1 (ng/mL) | | | |
| 0.1 | 865 ± 26 | 367 ± 120 | 42 |
| 0.3 | 1553 ± 361 | 402 ± 64 | 26 |
| 1 | 5074[a] | 284[a] | 6 |
| 3 | 7400 ± 718 | 275 ± 76 | 4 |
| 10 | 9642 ± 210 | 412 ± 131 | 4 |
| TSH (ng/mL) | | | |
| 0.01 | 755 ± 116 | 514 ± 112 | 68 |
| 0.03 | 1034 ± 115 | 982 ± 44 | 95 |
| 0.1 | 3829 ± 514 | 2292 ± 294 | 60 |
| 0.3 | 4967[a] | 4805 ± 170 | 97 |
| 1 | 9675 ± 1581 | 6491 ± 607 | 67 |
| 3 | 9847 ± 725 | 6092 ± 160 | 61 |
| Cyclic AMP assay buffer | 536[a] | 244 ± 20 | |
| Experiment 2 hMAb TSHR1 (ng/mL) | | | |
| 0.1 | 2539[a] | 484 ± 96 | 19 |
| 0.3 | 4054 ± 540 | 508 ± 104 | 13 |
| 1 | 12154 ± 2505 | 438 ± 113 | 4 |
| 3 | 12618[a] | 423[a] | 3 |
| 10 | 18702 ± 804 | 511 ± 216 | 3 |
| TSH (ng/mL) | | | |
| 0.01 | 1236 ± 139 | 692 ± 122 | 56 |
| 0.03 | 4588 ± 952 | 2448 ± 410 | 53 |
| 0.1 | 5620 ± 610 | 4735 ± 757 | 84 |
| 0.3 | 15580 ± 2946 | 12130 ± 1978 | 78 |
| 1 | 22808[a] | 16915 ± 852 | 74 |
| 3 | 23480 ± 1160 | 18031 ± 3157 | 77 |
| Cyclic AMP assay buffer | 679 ± 48 | 243 ± 31 | |

[a]mean of duplicate
hMAb TSHR1 Fab was used in all experiments

TABLE 15l

Effect of mutation of TSHR Phe130 to Ala on stimulation of cyclic AMP in CHO cells containing TSHR by hMAb TSHR1 and TSH

| | Cyclic AMP produced (fmol/cell well) mean ± SD (n = 3) | | Mutated/Wild |
|---|---|---|---|
| | Wild type TSHR | Mutated TSHR | type (%) |
| Experiment 1 hMAb TSHR1 (ng/mL) | | | |
| 0.1 | 2990 ± 1000 | 1613 ± 706 | 54 |
| 0.3 | 6015 ± 512 | 2126 ± 163 | 35 |
| 1 | 16504 ± 2978 | 3905 ± 265 | 24 |
| 3 | 19850 ± 1256 | 7947 ± 841 | 40 |
| 10 | 21517 ± 1037 | 17480 ± 2580 | 81 |
| TSH (ng/mL) | | | |
| 0.01 | 1614 ± 336 | 3371 ± 1847 | 209 |
| 0.03 | 2590 ± 672 | 4668 ± 47 | 180 |
| 0.1 | nd | 6373[a] | nd |
| 0.3 | 14754 ± 1095 | 19325 ± 4162 | 131 |
| 1 | 19712 ± 2403 | 26459 ± 319 | 134 |
| 3 | 24515 ± 1525 | 21361 ± 805 | 87 |
| Cyclic AMP assay buffer | 704 ± 64 | 998 ± 123 | |

TABLE 15l-continued

Effect of mutation of TSHR Phe130 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 2 | | | |
| hMAb TSHR1 (ng/mL) | | | |
| 0.1 | 1820 ± 165 | 776 ± 83 | 43 |
| 0.3 | 3536 ± 433 | 899 ± 21 | 25 |
| 1 | 9107 ± 1296 | 1438 ± 274 | 16 |
| 3 | 10390 ± 870 | 3832 ± 701 | 37 |
| 10 | 11042 ± 688 | 6864 ± 636 | 62 |
| TSH (ng/mL) | | | |
| 0.01 | 694 ± 43 | 700 ± 54 | 101 |
| 0.03 | 1470 ± 395 | 1616 ± 48 | 110 |
| 0.1 | 2663 ± 155 | 2863 ± 400 | 108 |
| 0.3 | 8206 ± 678 | 4904 ± 625 | 60 |
| 1 | 8888 ± 1514 | 9401 ± 1058 | 106 |
| 3 | 11261 ± 937 | 9735 ± 739 | 86 |
| Cyclic AMP assay buffer | 620 ± 63 | 522 ± 68 | |

[a]mean of duplicate
nd = not determined
hMAb TSHR1 Fab was used in all experiments TABLE 15m Effect of mutation of TSHR Phe134 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 2205 ± 404 | 1284 ± 130 | 58 |
| 0.3 | 5369 ± 753 | 2149 ± 559 | 40 |
| 1 | 16037 ± 697 | 8482 ± 353 | 53 |
| 3 | 22039 ± 1469 | 12127 ± 1947 | 55 |
| 10 | 20117 ± 1880 | 24649 ± 1133 | 123 |
| TSH (ng/mL) | | | |
| 0.01 | 1189 ± 278 | 776 ± 70 | 65 |
| 0.03 | 2004 ± 570 | 1232 ± 52 | 61 |
| 0.1 | 5366 ± 665 | 2622 ± 267 | 49 |
| 0.3 | 11790 ± 1622 | 7654 ± 675 | 65 |
| 1 | 16489 ± 2900 | 12049 ± 1239 | 73 |
| 3 | 24168 ± 1405 | 18525 ± 602 | 77 |
| Cyclic AMP assay buffer | 999 ± 33 | 714 ± 142 | |
| Experiment 2 | | | |
| hMAb TSHR1 (ng/mL) | | | |
| 0.1 | 2089 ± 201 | 1404 ± 67 | 67 |
| 0.3 | 4016 ± 338 | 2460 ± 191 | 61 |
| 1 | 9400 ± 853 | 6484 ± 304 | 69 |
| 3 | 12799 ± 450 | 11263 ± 1128 | 88 |
| 10 | 14729 ± 2011 | 14146 ± 1380 | 96 |
| TSH (ng/mL) | | | |
| 0.01 | 1108 ± 43 | 1022 ± 72 | 92 |
| 0.03 | 1511 ± 34 | 1475 ± 92 | 98 |
| 0.1 | 4111 ± 316 | 2660 ± 338 | 65 |
| 0.3 | 8747 ± 646 | 7108 ± 673 | 81 |
| 1 | 10290 ± 108 | 12726 ± 761 | 124 |
| 3 | 12027 ± 996 | 14785 ± 2611 | 123 |
| Cyclic AMP assay buffer | 584 ± 168 | 317 ± 19 | |

hMAb TSHR1 Fab was used in all experiments

TABLE 15n

Effect of mutation of TSHR Asp160 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1328 ± 186 | 814 ± 98 | 61 |
| 0.3 | 3123 ± 117 | 1658 ± 180 | 53 |
| 1 | 8120 ± 1331 | 3850 ± 213 | 47 |
| 3 | 12867 ± 1041 | 7536 ± 839 | 59 |
| 10 | 19292 ± 2362 | 11234 ± 1575 | 58 |
| TSH (ng/mL) | | | |
| 0.01 | 1100 ± 27 | 770 ± 48 | 70 |
| 0.03 | 2136 ± 566 | 901 ± 95 | 42 |
| 0.1 | nd | 2012 ± 439 | nd |
| 0.3 | 11668 ± 2382 | 4149 ± 927 | 36 |
| 1 | 18079 ± 206 | 8590 ± 1072 | 48 |
| 3 | 16979 ± 868 | 11805 ± 1364 | 70 |
| Cyclic AMP assay buffer | 742 ± 66 | 546 ± 56 | |
| Experiment 2 | | | |
| hMAb TSHR1 (ng/mL) | | | |
| 0.1 | 1430 ± 532 | 578 ± 238 | 40 |
| 0.3 | 2906 ± 471 | 1465 ± 392 | 50 |
| 1 | 10703 ± 1591 | 3239 ± 699 | 30 |
| 3 | 10749 ± 662 | 6772 ± 2578 | 63 |
| 10 | 23355[a] | 10965 ± 2713 | 47 |
| TSH (ng/mL) | | | |
| 0.01 | 1054 ± 28 | 789 ± 164 | 75 |
| 0.03 | 2241 ± 232 | 804 ± 125 | 36 |
| 0.1 | 5517 ± 755 | 1419 ± 395 | 26 |
| 0.3 | 14042 ± 1192 | 2731 ± 1041 | 19 |
| 1 | 13411 ± 3331 | 7500 ± 531 | 56 |
| 3 | 22093 ± 2324 | 10942 ± 3387 | 50 |
| Cyclic AMP assay buffer | 988 ± 69 | 672 ± 180 | |

[a]mean of duplicate
nd = not determined
hMAb TSHR1 Fab was used in all experiments TABLE 15o Effect of mutation of TSHR Lys183 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1461 ± 50 | 766 ± 78 | 52 |
| 0.3 | 2482 ± 141 | 1006 ± 24 | 41 |
| 1 | 7550 ± 616 | 1163 ± 175 | 15 |
| 3 | 9020 ± 703 | 1875 ± 350 | 21 |
| 10 | 10168 ± 1016 | 4658 ± 518 | 46 |
| TSH (ng/mL) | | | |
| 0.01 | 910 ± 110 | 921 ± 121 | 101 |
| 0.03 | 1289 ± 184 | 1293 ± 124 | 100 |
| 0.1 | 3302 ± 482 | 2132 ± 269 | 65 |
| 0.3 | 6584 ± 630 | 6661 ± 293 | 101 |
| 1 | 8834 ± 878 | 10049 ± 996 | 114 |
| 3 | 9296 ± 1282 | 10131 ± 1244 | 109 |
| Cyclic AMP assay buffer | 530 ± 185 | 1020 ± 39 | |

TABLE 15o-continued

Effect of mutation of TSHR Lys183 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 2 | | | |
| hMAb TSHR1 (ng/mL) | | | |
| 0.1 | 1370 ± 113 | 1379 ± 177 | 101 |
| 0.3 | 2542 ± 236 | 1478 ± 290 | 58 |
| 1 | 6654 ± 690 | 806 ± 160 | 12 |
| 3 | 10310 ± 1621 | 2907 ± 267 | 28 |
| 10 | 14617 ± 3147 | 5071 ± 388 | 35 |
| TSH (ng/mL) | | | |
| 0.01 | 699 ± 168 | 1144 ± 139 | 163 |
| 0.03 | 1471 ± 144 | 2193 ± 76 | 149 |
| 0.1 | 3134 ± 388 | 4292 ± 917 | 137 |
| 0.3 | 5976 ± 693 | 7846 ± 475 | 131 |
| 1 | 8083 ± 1246 | 18003 ± 4157 | 222 |
| 3 | 8896 ± 565 | 17403 ± 1656 | 196 |
| Cyclic AMP assay buffer | 659 ± 105 | 1010 ± 108 | |
| Experiment 3 | | | |
| hMAb TSHR1 (ng/mL) | | | |
| 0.1 | 1123 ± 187 | 799 ± 17 | 71 |
| 0.3 | 2037 ± 537 | 914 ± 49 | 45 |
| 1 | 6313 ± 115 | 1697 ± 357 | 27 |
| 3 | 7121 ± 904 | 2997 ± 195 | 42 |
| 10 | 8543 ± 1196 | 4838 ± 957 | 57 |
| TSH (ng/mL) | | | |
| 0.01 | 964 ± 62 | 846 ± 14 | 88 |
| 0.03 | 1069 ± 139 | 1359 ± 87 | 127 |
| 0.1 | 2903 ± 332 | 3061 ± 1253 | 105 |
| 0.3 | 6579 ± 584 | 5867 ± 763 | 89 |
| 1 | 7556 ± 566 | 9442 ± 629 | 125 |
| 3 | 8963 ± 288 | 10414 ± 2070 | 116 |
| Cyclic AMP assay buffer | 610 ± 22 | 804 ± 103 | |

hMAb TSHR1 Fab was used in all experiments

TABLE 15p

Effect of mutation of TSHR Lys183 to Asp on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1201 ± 198 | 882 ± 175 | 73 |
| 0.3 | 3025 ± 387 | 756 ± 74 | 25 |
| 1 | 9184 ± 1712 | 1070 ± 74 | 12 |
| 3 | 11693 ± 254 | 1596 ± 561 | 14 |
| 10 | 13439 ± 1799 | 2665 ± 318 | 20 |
| TSH (ng/mL) | | | |
| 0.01 | 838 ± 45 | 1332 ± 75 | 159 |
| 0.03 | 1387 ± 318 | 2531 ± 425 | 182 |
| 0.1 | 3993 ± 712 | 4037 ± 370 | 101 |
| 0.3 | 9320 ± 80 | 12166 ± 821 | 131 |
| 1 | 12667 ± 1548 | 21066 ± 2286 | 166 |
| 3 | 15764 ± 1934 | 22044 ± 1567 | 140 |
| Cyclic AMP assay buffer | 441 ± 41 | 837 ± 95 | |

TABLE 15p-continued

Effect of mutation of TSHR Lys183 to Asp on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 2 | | | |
| hMAb TSHR1 (ng/mL) | | | |
| 0.1 | 1227 ± 154 | 668 ± 39 | 54 |
| 0.3 | 2518 ± 118 | 594 ± 38 | 24 |
| 1 | 8013 ± 646 | 809 ± 22 | 10 |
| 3 | 12474 ± 540 | 1097 ± 59 | 9 |
| 10 | 14960 ± 989 | 1822 ± 116 | 12 |
| TSH (ng/mL) | | | |
| 0.01 | 693 ± 33 | 1063 ± 219 | 153 |
| 0.03 | 1531 ± 101 | 1711 ± 125 | 112 |
| 0.1 | 3619 ± 171 | 3278 ± 7 | 91 |
| 0.3 | 10721 ± 729 | 10204 ± 685 | 95 |
| 1 | 13599 ± 380 | 13881 ± 1383 | 102 |
| 3 | 17172 ± 1329 | 15261 ± 1578 | 89 |
| Cyclic AMP assay buffer | 509 ± 51 | 710 ± 51 | |

hMAb TSHR1 Fab was used in all experiments

TABLE 15q

Effect of mutation of TSHR Tyr185 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1560 ± 238 | 938 ± 68 | 60 |
| 0.3 | 3654 ± 516 | 1178 ± 178 | 32 |
| 1 | 9506 ± 1399 | 1540 ± 537 | 16 |
| 3 | 13540 ± 3538 | 2974 ± 240 | 22 |
| 10 | 16190 ± 2880 | 4654 ± 390 | 29 |
| TSH (ng/mL) | | | |
| 0.01 | 1134 ± 36 | 1148 ± 124 | 101 |
| 0.03 | 1344 ± 46 | 1492 ± 72 | 111 |
| 0.1 | 2218 ± 256 | 2586 ± 544 | 117 |
| 0.3 | 4980 ± 464 | 5260 ± 506 | 106 |
| 1 | 10620 ± 1080 | 8976 ± 526 | 85 |
| 3 | 16054 ± 1372 | 9619 ± 1098 | 60 |
| Cyclic AMP assay buffer | 930 ± 152 | 896 ± 120 | |
| Experiment 2 | | | |
| hMAb TSHR1 (ng/mL) | | | |
| 0.1 | 1754 ± 418 | 620 ± 82 | 35 |
| 0.3 | 2914 ± 210 | 620 ± 32 | 21 |
| 1 | 8630 ± 650 | 1030 ± 266 | 12 |
| 3 | 20120[a] | 1690 ± 108 | 8 |
| 10 | 18380 ± 436 | 3360 ± 380 | 18 |
| TSH (ng/mL) | | | |
| 0.01 | 760 ± 22 | 840 ± 70 | 111 |
| 0.03 | 1174 ± 230 | 1150 ± 86 | 98 |
| 0.1 | 1994 ± 26 | 2476 ± 395 | 124 |
| 0.3 | 4980 ± 979 | 3770 ± 216 | 76 |
| 1 | 10460 ± 1392 | 6260 ± 792 | 60 |
| 3 | 16230 ± 1754 | 9060 ± 2086 | 56 |
| Cyclic AMP assay buffer | 694 ± 11 | 586 ± 56 | |

[a]mean of duplicate hMAb TSHR1 Fab was used in all experiments

TABLE 15r

| Effect of mutation of TSHR Tyr206 to Ala on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 1 hMAb TSHR1 (ng/mL) | | | |
| 0.1 | 2730 ± 626 | 1362 ± 632 | 50 |
| 0.3 | 4960 ± 300 | 3366 ± 320 | 68 |
| 1 | 11744 ± 1142 | 5307 ± 1033 | 45 |
| 3 | 14787 ± 2786 | 14223 ± 1327 | 96 |
| 10 | 19505 ± 1949 | 19885 ± 3161 | 102 |
| TSH (ng/mL) | | | |
| 0.01 | 920 ± 816 | 822 ± 624 | 89 |
| 0.03 | 2360 ± 232 | 2092 ± 198 | 89 |
| 0.1 | 4276 ± 1166 | 4612 ± 754 | 108 |
| 0.3 | 14415[a] | 6570 ± 2268 | 46 |
| 1 | 13467 ± 2475 | 20320 ± 4656 | 151 |
| 3 | 17150 ± 3474 | 20753 ± 5641 | 121 |
| Cyclic AMP assay buffer | 670 ± 46 | 730 ± 112 | |
| Experiment 2 hMAb TSHR1 (ng/mL) | | | |
| 0.1 | 1815 ± 256 | 1410 ± 264 | 78 |
| 0.3 | 3059 ± 388 | 2594 ± 71 | 85 |
| 1 | 10159 ± 2795 | 6218 ± 480 | 61 |
| 3 | 16264 ± 1688 | 12698 ± 705 | 78 |
| 10 | 18386 ± 170 | 18523 ± 3130 | 101 |
| TSH (ng/mL) | | | |
| 0.01 | 1138 ± 139 | 979 ± 22 | 86 |
| 0.03 | 1588 ± 262 | 1523 ± 225 | 96 |
| 0.1 | 2438 ± 364 | 2804 ± 211 | 115 |
| 0.3 | 7787 ± 1111 | 7931 ± 414 | 102 |
| 1 | 12685 ± 1379 | 15817 ± 320 | 125 |
| 3 | 17173 ± 512 | 20529 ± 6651 | 120 |
| Cyclic AMP assay buffer | 763 ± 122 | 758 ± 65 | |

[a]mean of duplicate
hMAb TSHR1 Fab was used in all experiments

TABLE 15s

| Effect of mutation of TSHR Lys209 to Ala on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 1 hMAb TSHR1 (ng/mL) | | | |
| 0.1 | 2078 ± 431 | 745 ± 9 | 36 |
| 0.3 | 5275 ± 941 | 1504 ± 235 | 29 |
| 1 | 10842 ± 505 | 3057 ± 158 | 28 |
| 3 | 17487 ± 2798 | 7931 ± 2983 | 45 |
| 10 | 23304 ± 1886 | 12495 ± 689 | 54 |
| TSH (ng/mL) | | | |
| 0.01 | 1605 ± 609 | 780 ± 80 | 49 |
| 0.03 | 2711 ± 343 | 1641 ± 375 | 61 |
| 0.1 | 5653[a] | 2798 ± 373 | 49 |
| 0.3 | 15819 ± 2569 | 7423 ± 2337 | 47 |
| 1 | 22465 ± 3295 | 15616 ± 336 | 70 |
| 3 | 24344 ± 6711 | 16125 ± 1656 | 66 |
| Cyclic AMP assay buffer | 735 ± 69 | 592 ± 14 | |

TABLE 15s-continued

| Effect of mutation of TSHR Lys209 to Ala on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 2 hMAb TSHR1 (ng/mL) | | | |
| 0.1 | 1485 ± 77 | 1169 ± 88 | 79 |
| 0.3 | 3934 ± 295 | 1390 ± 333 | 35 |
| 1 | 8271 ± 419 | 4929 ± 144 | 60 |
| 3 | 15762 ± 1879 | 7564 ± 528 | 48 |
| 10 | 25020 ± 2040 | 16556 ± 2821 | 66 |
| TSH (ng/mL) | | | |
| 0.01 | 1481 ± 286 | 1106 ± 230 | 75 |
| 0.03 | 2373 ± 519 | 1507 ± 160 | 64 |
| 0.1 | 6160[a] | 2781 ± 632 | 45 |
| 0.3 | 12743 ± 2376 | 6478 ± 883 | 51 |
| 1 | 19059 ± 1638 | 14596 ± 2090 | 77 |
| 3 | 18790 ± 2563 | 16519 ± 1386 | 88 |
| Cyclic AMP assay buffer | 911 ± 164 | 989 ± 87 | |

[a]mean of duplicate
hMAb TSHR1 Fab was used in all experiments

TABLE 15t

| Effect of mutation of TSHR Asp232 to Arg on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 1 hMAb TSHR1 (ng/mL) | | | |
| 0.1 | 872 ± 87 | 376 ± 33 | 43 |
| 0.3 | 1807 ± 541 | 345 ± 57 | 19 |
| 1 | 6117 ± 1041 | 336 ± 168 | 5 |
| 3 | 12613 ± 887 | 482 ± 112 | 4 |
| 10 | 17622 ± 2689 | 365 ± 176 | 2 |
| TSH (ng/mL) | | | |
| 0.01 | 565 ± 37 | 499 ± 36 | 88 |
| 0.03 | 730 ± 205 | 415 ± 83 | 57 |
| 0.1 | 1718 ± 238 | 401 ± 87 | 23 |
| 0.3 | 5104 ± 985 | 482 ± 68 | 9 |
| 1 | 9314 ± 805 | 247 ± 60 | 3 |
| 3 | 15288 ± 4763 | 337 ± 19 | 2 |
| Cyclic AMP assay buffer | 296 ± 96 | 326 ± 42 | |
| Experiment 2 hMAb TSHR1 (ng/mL) | | | |
| 0.1 | 579 ± 70 | 310 ± 38 | 54 |
| 0.3 | 1860 ± 720 | 260 ± 15 | 14 |
| 1 | 6492 ± 3623 | 202 ± 19 | 3 |
| 3 | 19766 ± 8102 | 191 ± 38 | 1 |
| 10 | 23054 ± 6165 | 185 ± 49 | 1 |
| TSH (ng/mL) | | | |
| 0.01 | 528 ± 53 | 407 ± 56 | 77 |
| 0.03 | 536 ± 104 | 314 ± 27 | 59 |
| 0.1 | 3114 ± 586 | 292 ± 29 | 9 |
| 0.3 | 3318 ± 676 | 598 ± 706 | 18 |
| 1 | 15396 ± 4345 | 220 ± 3 | 1 |
| 3 | 18431 ± 4386 | 174 ± 16 | 1 |
| Cyclic AMP assay buffer | 364 ± 20 | 326 ± 10 | |

hMAb TSHR1 Fab was used in all experiments

TABLE 15u

| Effect of mutation of TSHR Lys250 to Ala on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 1 | | | |
| hMAb TSHR1 (ng/mL) | | | |
| 0.1 | nd | nd | nd |
| 0.3 | 3513 ± 322 | 4225 ± 118 | 120 |
| 1 | 10885 ± 74 | 9440 ± 601 | 87 |
| 3 | 15718 ± 1932 | 15433 ± 841 | 98 |
| 10 | 21864 ± 441 | 18373 ± 860 | 84 |
| TSH (ng/mL) | | | |
| 0.01 | 1168 ± 206 | 1677 ± 259 | 144 |
| 0.03 | 1830 ± 144 | 2466 ± 430 | 135 |
| 0.1 | 4133 ± 300 | 4506 ± 348 | 109 |
| 0.3 | 9269 ± 1709 | 11416 ± 747 | 123 |
| 1 | 18165 ± 2560 | 16101 ± 794 | 89 |
| 3 | 24491 ± 903 | 18142 ± 1121 | 74 |
| Cyclic AMP assay buffer | 873 ± 101 | 1143 ± 47 | |
| Experiment 2 | | | |
| hMAb TSHR1 (ng/mL) | | | |
| 0.1 | 1599 ± 213 | 1756 ± 288 | 110 |
| 0.3 | 3312 ± 554 | 3370 ± 398 | 102 |
| 1 | 9469 ± 2932 | 7817 ± 924 | 83 |
| 3 | 15451 ± 1813 | 10944 ± 1432 | 71 |
| 10 | 23359 ± 998 | 16126 ± 1202 | 69 |
| TSH (ng/mL) | | | |
| 0.01 | 1543 ± 276 | 1242 ± 152 | 80 |
| 0.03 | 2150 ± 252 | 2129 ± 176 | 99 |
| 0.1 | nd | 4235 ± 542 | nd |
| 0.3 | 14628 ± 2493 | 11155 ± 1593 | 76 |
| 1 | 18693 ± 1137 | 15395 ± 1097 | 82 |
| 3 | 18628 ± 1570 | 18313 ± 677 | 98 |
| Cyclic AMP assay buffer | 1000 ± 82 | 899 ± 138 | |

nd = not determined hMAb TSHR1 Fab was used in all experiments

TABLE 15v

| Effect of mutation of TSHR Glu251 to Ala on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 1 | | | |
| hMAb TSHR1 (ng/mL) | | | |
| 0.1 | 1468 ± 150 | 1806 ± 113 | 123 |
| 0.3 | 2988 ± 150 | 2496 ± 368 | 84 |
| 1 | 8626 ± 473 | 6874 ± 146 | 80 |
| 3 | 13768 ± 1791 | 10810 ± 210 | 79 |
| 10 | 18100 ± 1361 | 12512 ± 297 | 69 |
| TSH (ng/mL) | | | |
| 0.01 | 1204 ± 57 | 1324 ± 63 | 110 |
| 0.03 | 1496 ± 111 | 1764 ± 134 | 118 |
| 0.1 | 3344 ± 617 | 2570 ± 273 | 77 |
| 0.3 | 9270 ± 962 | 6872 ± 457 | 74 |
| 1 | 15644 ± 2238 | 11232 ± 1478 | 72 |
| 3 | 18494 ± 1815 | 11560 ± 2771 | 63 |
| Cyclic AMP assay buffer | 998 ± 94 | 1200 ± 105 | |

TABLE 15v-continued

| Effect of mutation of TSHR Glu251 to Ala on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 2 | | | |
| hMAb TSHR1 (ng/mL) | | | |
| 0.1 | 990 ± 116 | 1332 ± 214 | 135 |
| 0.3 | 2186 ± 237 | 3034 ± 205 | 139 |
| 1 | 6726 ± 147 | 4690 ± 375 | 70 |
| 3 | 11466 ± 403 | 11476 ± 726 | 100 |
| 10 | 19820 ± 2013 | 16780 ± 1825 | 85 |
| TSH (ng/mL) | | | |
| 0.01 | 820 ± 133 | 1552 ± 322 | 186 |
| 0.03 | 1610 ± 150 | 2476 ± 321 | 187 |
| 0.1 | 3912 ± 298 | 4922 ± 750 | 126 |
| 0.3 | 10490 ± 1393 | 8630 ± 1595 | 82 |
| 1 | 12960 ± 2792 | 14110 ± 757 | 109 |
| 3 | 16684 ± 958 | 18476 ± 1985 | 111 |
| Cyclic AMP assay buffer | 660 ± 29 | 864 ± 106 | |

hMAb TSHR1 Fab was used in all experiments

TABLE 15w

| Effect of mutation of TSHR Arg274 to Ala on stimulation of cyclic AMP in CHO cells containing TSHR by hMAb TSHR1 and TSH | | | |
|---|---|---|---|
| | Cyclic AMP produced (fmol/cell well) mean ± SD (n = 3) | | Mutated/ Wild |
| | Wild type TSHR | Mutated TSHR | type (%) |
| Experiment 1 | | | |
| hMAb TSHR1 (ng/mL) | | | |
| 0.1 | 1390 ± 607 | 686 ± 63 | 49 |
| 0.3 | 2850 ± 170 | 1310 ± 284 | 46 |
| 1 | 7313 ± 587 | 3295 ± 25 | 45 |
| 3 | 13913 ± 3769 | 8454 ± 2347 | 61 |
| 10 | 14998 ± 1828 | 14567 ± 1722 | 97 |
| TSH (ng/mL) | | | |
| 0.01 | 666 ± 56 | 552 ± 30 | 83 |
| 0.03 | 712 ± 25 | 664 ± 28 | 93 |
| 0.1 | 2184 ± 104 | 1216 ± 340 | 56 |
| 0.3 | 3976 ± 254 | 2664 ± 14 | 67 |
| 1 | 11032 ± 1183 | 6310 ± 394 | 57 |
| 3 | 13956 ± 1306 | 9688 ± 1557 | 69 |
| Cyclic AMP assay buffer | 590 ± 30 | 553 ± 24 | |
| Experiment 2 | | | |
| hMAb TSHR1 (ng/mL) | | | |
| 0.1 | 1380 ± 276 | 996 ± 56 | 72 |
| 0.3 | 2858 ± 18 | 1510 ± 252 | 53 |
| 1 | 9024 ± 1360 | 4654 ± 1369 | 52 |
| 3 | 12920 ± 959 | 8230 ± 1371 | 64 |
| 10 | 15570 ± 454 | 12430 ± 2176 | 80 |
| TSH (ng/mL) | | | |
| 0.01 | 702 ± 152 | 1022 ± 370 | 146 |
| 0.03 | 854 ± 98 | 976 ± 72 | 114 |
| 0.1 | 1412 ± 106 | 1578 ± 382 | 112 |
| 0.3 | 3364 ± 122 | 3960 ± 587 | 118 |
| 1 | 9936 ± 1003 | 8954 ± 1158 | 90 |
| 3 | 12894 ± 1009 | 11234 ± 856 | 87 |
| Cyclic AMP assay buffer | 618 ± 51 | 608 ± 80 | |

hMAb TSHR1 Fab was used in all experiments

TABLE 15x

Effect of mutation of TSHR Tyr279 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1590 ± 124 | 656 ± 100 | 41 |
| 0.3 | 2760 ± 24 | 682 ± 188 | 7 |
| 1 | 8506 ± 419 | 996 ± 150 | 12 |
| 3 | 15260 ± 2326 | 680 ± 25 | 4 |
| 10 | 17580 ± 2606 | 784 ± 145 | 4 |
| TSH (ng/mL) | | | |
| 0.01 | 864 ± 24 | 1068 ± 124 | 124 |
| 0.03 | 1258 ± 80 | 926 ± 32 | 74 |
| 0.1 | 2410 ± 244 | 750 ± 250 | 31 |
| 0.3 | 5034 ± 178 | 1064 ± 220 | 21 |
| 1 | 13896 ± 1193 | 1236 ± 281 | 9 |
| 3 | 15820 ± 784 | 1424 ± 218 | 9 |
| Cyclic AMP assay buffer | 730 ± 16 | 750 ± 24 | |
| Experiment 2 | | | |
| hMAb TSHR1 (ng/mL) | | | |
| 0.1 | 1390 ± 136 | 686 ± 82 | 49 |
| 0.3 | 3116 ± 552 | 623 ± 114 | 20 |
| 1 | 6123 ± 514 | 410 ± 59 | 7 |
| 3 | 13878 ± 2820 | 500 ± 83 | 4 |
| 10 | 14995 ± 1266 | 674 ± 149 | 4 |
| TSH (ng/mL) | | | |
| 0.01 | 830 ± 32 | 684 ± 22 | 82 |
| 0.03 | 1164 ± 374 | 688 ± 118 | 59 |
| 0.1 | 1960 ± 126 | 766 ± 106 | 39 |
| 0.3 | 3780 ± 567 | 695 ± 162 | 18 |
| 1 | 8691 ± 662 | 810 ± 227 | 9 |
| 3 | 12673 ± 742 | 1217 ± 170 | 10 |
| Cyclic AMP assay buffer | 676 ± 44 | 578 ± 26 | |

hMAb TSHR1 Fab was used in all experiments

TABLE 16

Summary of effects of mutation (relative to wild type) on stimulation of CHO cells containing mutated TSHR

| aa mutation | TSH stimulation | hMAb TSHR1 Fab stimulation |
|---|---|---|
| Lys58 to Ala | no effect | no effect |
| Ile60 to Ala | no effect | no effect |
| Arg80 to Ala | no effect | marked reduction |
| Arg80 to Asp | no effect | marked reduction |
| Tyr82 to Ala | no effect | some reduction |
| Glu107 to Ala | some reduction | marked reduction |
| Glu107 to Arg | marked reduction | marked reduction |
| Arg109 to Ala | no effect | marked reduction |
| Arg109 to Asp | some reduction | marked reduction |
| Lys129 to Ala | no effect | marked reduction |
| Lys129 to Asp | no effect | marked reduction |
| Phe130 to Ala | no effect | marked reduction |
| Phe134 to Ala | no effect | no effect |
| Asp160 to Ala | some reduction | some reduction |
| Lys183 to Ala | no effect | marked reduction |
| Lys183 to Asp | no effect | marked reduction |
| Tyr185 to Ala | no effect | marked reduction |
| Tyr206 to Ala | no effect | no effect |
| Lys209 to Ala | some reduction | some reduction |
| Asp232 to Arg | marked reduction | marked reduction |
| Lys250 to Ala | no effect | no effect |
| Glu251 to Ala | no effect | no effect |
| Arg274 to Ala | no effect | no effect |
| Tyr279 to Ala | marked reduction | marked reduction |

TABLE 17a

TSH induced cyclic AMP production in CHO cells expressing wild type TSHR and TSHR with Lys58 mutated to Ala. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ Wild |
|---|---|---|---|
| Test sample[a] | Wild type TSHR | Mutated TSHR | type (%) |
| Cyclic AMP assay buffer only | 545 ± 200 | 640 ± 34 | 117 |
| TSH | 21110 ± 1582 | 17775 ± 1851 | 84 |
| 2G2 1 μg/mL + TSH[b] | 19943[c] | 22426 ± 3322 | 112 |
| 2G2 10 μg/mL + TSH[b] | 24474 ± 1746 | 17626 ± 3253 | 72 |
| 2G2 100 μg/mL + TSH[b] | 21471 ± 1436 | 17478 ± 679 | 81 |
| 9D33 0.001 μg/mL + TSH[b] | 18865 ± 2836 | 23464 ± 2827 | 124 |
| 9D33 0.01 μg/mL + TSH[b] | 21648 ± 2909 | 16053[c] | 74 |
| 9D33 0.1 μg/mL + TSH[b] | 27181[c] | 22621 ± 610 | 83 |
| 9D33 1 μg/mL + TSH[b] | 13290 ± 2829 | 20233 ± 2223 | 152 |
| 9D33 10 μg/mL + TSH[b] | 7942 ± 2403 | 20192 ± 3977 | 254 |
| 9D33 100 μg/mL + TSH[b] | 2447 ± 1679 | 23258 ± 4341 | 950 |
| 9D33 100 μg | 832 ± 89 | 1204 ± 366 | 145 |

B % inhibition results

| | % inhibition of TSH stimulation[d] | |
|---|---|---|
| Antibody concentration | Wild type TSHR | Mutated TSHR |
| 2G2 1 μg/mL | 6 | −26 |
| 2G2 10 μg/mL | −16 | 1 |
| 2G2 100 μg/mL | −2 | 2 |
| 9D33 0.001 μg/mL | 11 | −32 |
| 9D33 0.01 μg/mL | −3 | 10 |
| 9D33 0.1 μg/mL | −29 | −27 |
| 9D33 1 μg/mL | 37 | −14 |
| 9D33 10 μg/mL | 62 | −14 |
| 9D33 100 μg/mL | 88 | −31 |

[a]Test samples in cyclic AMP assay buffer
[b]TSH final concentration = 1.5 ng/mL
[c]mean of duplicate
[d]% inhibition =

$$100\times\left(1-\frac{\text{cAMP in presence of test sample}+\text{TSH}}{\text{cAMP in presence of cyclic AMP assay buffer}+\text{TSH}}\right)$$

2G2 is a mouse monoclonal antibody to thyroglobulin (negative control for 9D33)

TABLE 17b

TSH induced cyclic AMP production in CHO cells expressing wild type TSHR and TSHR with Ile60 mutated to Ala. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ Wild |
|---|---|---|---|
| Test sample[a] | Wild type TSHR | Mutated TSHR | type (%) |
| Cyclic AMP assay buffer only | 557 ± 105 | 889 ± 208 | 160 |
| TSH | 16781 ± 1025 | 14407 ± 3748 | 86 |
| 2G2 1 μg/mL + TSH[b] | 12022 ± 2220 | 16669 ± 2167 | 139 |
| 2G2 10 μg/mL + TSH[b] | 12439 ± 2453 | 15501 ± 1141 | 125 |
| 2G2 100 μg/mL + TSH[b] | 13056 ± 1630 | 15106 ± 931 | 116 |

TABLE 17b-continued

| | | | |
|---|---|---|---|
| 9D33 0.001 μg/mL + TSH[b] | 13587 ± 1777 | 18962 ± 4050 | 140 |
| 9D33 0.01 μg/mL + TSH[b] | 12993 ± 2404 | 18797[c] | 145 |
| 9D33 0.1 μg/mL + TSH[b] | 11196 ± 1798 | 14519 ± 3400 | 130 |
| 9D33 1 μg/mL + TSH[b] | 6601 ± 712 | 12120[c] | 184 |
| 9D33 10 μg/mL + TSH[b] | 4500 ± 678 | 7217 ± 512 | 160 |
| 9D33 100 μg/mL + TSH[b] | 1627 ± 166 | 4886 ± 382 | 300 |
| 9D33 100 μg | 849 ± 207 | 1174 ± 312 | 138 |

B % inhibition results

| | % inhibition of TSH stimulation[d] | |
|---|---|---|
| Antibody concentration | Wild type TSHR | Mutated TSHR |
| 2G2 1 μg/mL | 28 | −16 |
| 2G2 10 μg/mL | 26 | −8 |
| 2G2 100 μg/mL | 22 | −5 |
| 9D33 0.001 μg/mL | 19 | −32 |
| 9D33 0.01 μg/mL | 23 | −30 |
| 9D33 0.1 μg/mL | 33 | 0 |
| 9D33 1 μg/mL | 61 | 16 |
| 9D33 10 μg/mL | 73 | 50 |
| 9D33 100 μg/mL | 90 | 66 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17c

TSH induced cyclic AMP production in CHO cells expressing wild type TSHR and TSHR with Arg80 mutated to Ala. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ |
|---|---|---|---|
| Test sample[a] | Wild type TSHR | Mutated TSHR | Wild type (%) |
| Cyclic AMP assay buffer only | 714 ± 43 | 1088 ± 92 | 152 |
| TSH | 18979[c] | 19704 ± 2677 | 104 |
| 2G2 1 μg/mL + TSH[b] | 20640 ± 581 | 20980[c] | 102 |
| 2G2 10 μg/mL + TSH[b] | 18496 ± 343 | 19799 ± 1419 | 107 |
| 2G2 100 μg/mL + TSH[b] | 19699 ± 1947 | 23450 ± 923 | 119 |
| 9D33 0.001 μg/mL + TSH[b] | 19575 ± 4282 | 25960 ± 1357 | 133 |
| 9D33 0.01 μg/mL + TSH[b] | 23162 ± 1504 | 18751 ± 865 | 81 |
| 9D33 0.1 μg/mL + TSH[b] | 17648 ± 2178 | 23899 ± 300 | 135 |
| 9D33 1 μg/mL + TSH[b] | 9905 ± 1476 | 20875 ± 800 | 211 |
| 9D33 10 μg/mL + TSH[b] | 5145 ± 495 | 20797 ± 3441 | 404 |
| 9D33 100 μg/mL + TSH[b] | 2241 ± 281 | 21076 ± 2980 | 904 |
| 9D33 100 μg | 965 ± 86 | 1571 ± 205 | 163 |

B % inhibition results

| | % inhibition of TSH stimulation[d] | |
|---|---|---|
| Antibody concentration | Wild type TSHR | Mutated TSHR |
| 2G2 1 μg/mL | −9 | −6 |
| 2G2 10 μg/mL | 3 | 0 |

TABLE 17c-continued

| | | |
|---|---|---|
| 2G2 100 μg/mL | −4 | −19 |
| 9D33 0.001 μg/mL | −3 | −32 |
| 9D33 0.01 μg/mL | −22 | 5 |
| 9D33 0.1 μg/mL | 7 | −21 |
| 9D33 1 μg/mL | 49 | −6 |
| 9D33 10 μg/mL | 73 | −6 |
| 9D33 100 μg/mL | 88 | −7 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17d

TSH induced cyclic AMP production in CHO cells expressing wild type TSHR and TSHR with Arg80 mutated to Asp. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ |
|---|---|---|---|
| Test sample[a] | Wild type TSHR | Mutated TSHR | Wild type (%) |
| Cyclic AMP assay buffer only | 659 ± 58 | 514 ± 40 | 78 |
| TSH | 20019 ± 1871 | 17217 ± 2685 | 86 |
| 2G2 1 μg/mL + TSH[b] | 16429 ± 308 | 17022 ± 1123 | 104 |
| 2G2 10 μg/mL + TSH[b] | 18361 ± 1176 | 15857 ± 2364 | 86 |
| 2G2 100 μg/mL + TSH[b] | 16916 ± 814 | 16942 ± 1683 | 100 |
| 9D33 0.001 μg/mL + TSH[b] | 15724 ± 1763 | 20521 ± 3779 | 131 |
| 9D33 0.01 μg/mL + TSH[b] | 15737 ± 1060 | 19300 ± 1479 | 123 |
| 9D33 0.1 μg/mL + TSH[b] | 16788 ± 1341 | 16258 ± 3120 | 97 |
| 9D33 1 μg/mL + TSH[b] | 8613 ± 674 | 21217 ± 2058 | 246 |
| 9D33 10 μg/mL + TSH[b] | 3517 ± 798 | 17035 ± 1707 | 484 |
| 9D33 100 μg/mL + TSH[b] | 1869 ± 200 | 18217 ± 1061 | 975 |
| 9D33 100 μg | 950 ± 504 | 675 ± 80 | 71 |

B % inhibition results

| | % inhibition of TSH stimulation[c] | |
|---|---|---|
| Antibody concentration | Wild type TSHR | Mutated TSHR |
| 2G2 1 μg/mL | 18 | 1 |
| 2G2 10 μg/mL | 8 | 8 |
| 2G2 100 μg/mL | 16 | 2 |
| 9D33 0.001 μg/mL | 21 | −19 |
| 9D33 0.01 μg/mL | 21 | −12 |
| 9D33 0.1 μg/mL | 16 | 6 |
| 9D33 1 μg/mL | 57 | −23 |
| 9D33 10 μg/mL | 82 | 1 |
| 9D33 100 μg/mL | 95 | 6 |

[a]Test samples in cyclic AMP assay buffer
[b]TSH final concentration = 1.5 ng/mL
[c]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17e

TSH induced cyclic AMP production in CHO cells expressing wild type TSHR and TSHR with Tyr82 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 599 ± 71 | 548 ± 25 | 91 |
| TSH | 8350 ± 1303 | 6602 ± 96 | 79 |
| 2G2 1 μg/mL + TSH[b] | 7358 ± 1153 | 5446 ± 265 | 74 |
| 2G2 10 μg/mL + TSH[b] | 9821 ± 1749 | 5906 ± 335 | 60 |
| 2G2 100 μg/mL + TSH[b] | 7962 ± 1218 | 5771 ± 19 | 72 |
| 9D33 0.001 μg/mL + TSH[b] | 6393 ± 1036 | 8064 ± 1472 | 126 |
| 9D33 0.01 μg/mL + TSH[b] | 9482 ± 1536 | 7608 ± 875 | 80 |
| 9D33 0.1 μg/mL + TSH[b] | 8910 ± 526 | 6485 ± 146 | 73 |
| 9D33 1 μg/mL + TSH[b] | 4009 ± 447 | 7291 ± 591 | 181 |
| 9D33 10 μg/mL + TSH[b] | 3395 ± 238 | 7648 ± 1386 | 225 |
| 9D33 100 μg/mL + TSH[b] | 2869 ± 254 | 5951 ± 1035 | 207 |
| 9D33 100 μg | 596 ± 33 | 679 ± 48 | 114 |

B % inhibition results

| Antibody concentration | % inhibition of TSH stimulation[c] Wild type TSHR | Mutated TSHR |
|---|---|---|
| 2G2 1 μg/mL | 12 | 18 |
| 2G2 10 μg/mL | −18 | 11 |
| 2G2 100 μg/mL | 5 | 13 |
| 9D33 0.001 μg/mL | 23 | −22 |
| 9D33 0.01 μg/mL | −14 | −15 |
| 9D33 0.1 μg/mL | −7 | 2 |
| 9D33 1 μg/mL | 52 | −10 |
| 9D33 10 μg/mL | 59 | −16 |
| 9D33 100 μg/mL | 66 | 10 |

[a]Test samples in cyclic AMP assay buffer
[b]TSH final concentration = 1.5 ng/mL
[c]% inhibition =

$$100\times\left(1-\frac{\text{cAMP in presence of test sample}+\text{TSH}}{\text{cAMP in presence of cyclic AMP assay buffer}+\text{TSH}}\right)$$

2G2 is a mouse monoclonal antibody to thyroglobulin (negative control for 9D33)

TABLE 17f

TSH induced cyclic AMP production in CHO cells expressing wild type TSHR and TSHR with Glu107 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 893 ± 103 | 1215 ± 93 | 136 |
| TSH | 18593 ± 2469 | 14789 ± 3005 | 80 |
| 2G2 1 μg/mL + TSH[b] | 17253 ± 1508 | 13057 ± 1259 | 76 |
| 2G2 10 μg/mL + TSH[b] | 18423 ± 4503 | 9495 ± 1017 | 52 |

TABLE 17f-continued

| | | | |
|---|---|---|---|
| 2G2 100 μg/mL + TSH[b] | 18952 ± 3984 | 13210 ± 2663 | 70 |
| 9D33 0.001 μg/mL + TSH[b] | 17646 ± 1558 | 9589 ± 516 | 54 |
| 9D33 0.01 μg/mL + TSH[b] | 20021 ± 949 | 11194 ± 147 | 56 |
| 9D33 0.1 μg/mL + TSH[b] | 16937 ± 2431 | 7651 ± 1178 | 45 |
| 9D33 1 μg/mL + TSH[b] | 11655 ± 4674 | 5613 ± 1549 | 48 |
| 9D33 10 μg/mL + TSH[b] | 5903 ± 1022 | 2386 ± 1294 | 40 |
| 9D33 100 μg/mL + TSH[b] | 3493 ± 395 | 2536 ± 388 | 73 |
| 9D33 100 μg | 996 ± 108 | 963 ± 192 | 97 |

B % inhibition results

| Antibody concentration | % inhibition of TSH stimulation[c] Wild type TSHR | Mutated TSHR |
|---|---|---|
| 2G2 1 μg/mL | 7 | 12 |
| 2G2 10 μg/mL | 1 | 36 |
| 2G2 100 μg/mL | −2 | 11 |
| 9D33 0.001 μg/mL | 5 | 35 |
| 9D33 0.01 μg/mL | −8 | 24 |
| 9D33 0.1 μg/mL | 9 | 48 |
| 9D33 1 μg/mL | 37 | 62 |
| 9D33 10 μg/mL | 68 | 84 |
| 9D33 100 μg/mL | 81 | 83 |

[a]Test samples in cyclic AMP assay buffer
[b]TSH final concentration = 1.5 ng/mL
[c]% inhibition =

$$100\times\left(1-\frac{\text{cAMP in presence of test sample}+\text{TSH}}{\text{cAMP in presence of cyclic AMP assay buffer}+\text{TSH}}\right)$$

2G2 is a mouse monoclonal antibody to thyroglobulin (negative control for 9D33)

TABLE 17g

TSH induced cyclic AMP production in CHO cells expressing wild type TSHR and TSHR with Glu107 mutated to Arg. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 1126 ± 74 | 1263 ± 73 | 112 |
| TSH | 21406 ± 932 | 5857 ± 571 | 27 |
| 2G2 1 μg/mL + TSH[b] | 21490 ± 2227 | 5357 ± 756 | 25 |
| 2G2 10 μg/mL + TSH[b] | 18305 ± 2116 | 5502 ± 431 | 30 |
| 2G2 100 μg/mL + TSH[b] | 20965 ± 3258 | 4655 ± 243 | 22 |
| 9D33 0.001 μg/mL + TSH[b] | 23207 ± 5032 | 4504 ± 471 | 19 |
| 9D33 0.01 μg/mL + TSH[b] | 20373 ± 2048 | 5297 ± 1069 | 26 |
| 9D33 0.1 μg/mL + TSH[b] | 16380 ± 566 | 5577 ± 192 | 34 |
| 9D33 1 μg/mL + TSH[b] | 16364 ± 2028 | 5285 ± 885 | 32 |
| 9D33 10 μg/mL + TSH[b] | 8126 ± 407 | 5774 ± 866 | 71 |
| 9D33 100 μg/mL + TSH[b] | 3587[c] | 5290 ± 619 | 147 |
| 9D33 100 μg | 973[c] | 720 ± 105 | 74 |

B % inhibition results

| Antibody concentration | % inhibition of TSH stimulation[d] Wild type TSHR | Mutated TSHR |
|---|---|---|
| 2G2 1 μg/mL | 0 | 9 |
| 2G2 10 μg/mL | 14 | 6 |
| 2G2 100 μg/mL | 2 | 21 |
| 9D33 0.001 μg/mL | −8 | 23 |

TABLE 17g-continued

| | | |
|---|---|---|
| 9D33 0.01 μg/mL | 5 | 10 |
| 9D33 0.1 μg/mL | 23 | 5 |
| 9D33 1 μg/mL | 24 | 10 |
| 9D33 10 μg/mL | 62 | 1 |
| 9D33 100 μg/mL | 83 | 10 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17h

TSH induced cyclic AMP production in CHO cells expressing wild type TSHR and TSHR with Arg109 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 734 ± 285 | 1214 ± 66 | 165 |
| TSH | 15683 ± 3332 | 16060 ± 3546 | 102 |
| 2G2 1 μg/mL + TSH[b] | 16962 ± 3784 | 15661 ± 1152 | 92 |
| 2G2 10 μg/mL + TSH[b] | 16231[c] | 12589 ± 1450 | 78 |
| 2G2 100 μg/mL + TSH[b] | 16675 ± 3301 | 16387 ± 1142 | 98 |
| 9D33 0.001 μg/mL + TSH[b] | 16646 ± 2135 | 15716 ± 283 | 94 |
| 9D33 0.01 μg/mL + TSH[b] | 18722 ± 1091 | 14075 ± 905 | 75 |
| 9D33 0.1 μg/mL + TSH[b] | 13435 ± 333 | 13803 ± 1416 | 103 |
| 9D33 1 μg/mL + TSH[b] | 8004 ± 2106 | 14551 ± 2498 | 182 |
| 9D33 10 μg/mL + TSH[b] | 4718 ± 867 | 11169 ± 488 | 237 |
| 9D33 100 μg/mL + TSH[b] | 1991 ± 494 | 9554 ± 830 | 480 |
| 9D33 100 μg | 1155 ± 73 | 1148 ± 19 | 99 |

B % inhibition results

| Antibody concentration | % inhibition of TSH stimulation[d] Wild type TSHR | Mutated TSHR |
|---|---|---|
| 2G2 1 μg/mL | −8 | 2 |
| 2G2 10 μg/mL | −3 | 22 |
| 2G2 100 μg/mL | −6 | −2 |
| 9D33 0.001 μg/mL | −6 | 2 |
| 9D33 0.01 μg/mL | −19 | 12 |
| 9D33 0.1 μg/mL | 14 | 14 |
| 9D33 1 μg/mL | 49 | 9 |
| 9D33 10 μg/mL | 70 | 30 |
| 9D33 100 μg/mL | 87 | 59 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17i

TSH induced cyclic AMP production in CHO cells expressing wild type TSHR and TSHR with Arg109 mutated to Asp. Effect of different dilutions of monoclonal antibody to the TSH receptor (9D33) with TSR antagonist actiyity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 656 ± 50 | 312 ± 151 | 48 |
| TSH | 16975[c] | 12341 ± 1724 | 73 |
| 2G2 1 μg/mL + TSH[b] | 13540 ± 1490 | 11663 ± 980 | 86 |
| 2G2 10 μg/mL + TSH[b] | 12805 ± 785 | 10932 ± 1779 | 85 |
| 2G2 100 μg/mL + TSH[b] | 13629 ± 689 | 12795 ± 2243 | 94 |
| 9D33 0.001 μg/mL + TSH[b] | 14034 ± 1530 | 14046 ± 2244 | 100 |
| 9D33 0.01 μg/mL + TSH[b] | 12506 ± 1906 | 10787 ± 1468 | 86 |
| 9D33 0.1 μg/mL + TSH[b] | 10790 ± 1948 | 14003 ± 89 | 130 |
| 9D33 1 μg/mL + TSH[b] | 7392 ± 661 | 15087 ± 2096 | 204 |
| 9D33 10 μg/mL + TSH[b] | 3293 ± 457 | 11271 ± 1633 | 342 |
| 9D33 100 μg/mL + TSH[b] | 2062 ± 439 | 10178 ± 1136 | 494 |
| 9D33 100 μg | 564 ± 66 | 367 ± 45 | 65 |

B % inhibition results

| Antibody concentration | % inhibition of TSH stimulation[d] Wild type TSHR | Mutated TSHR |
|---|---|---|
| 2G2 1 μg/mL | 20 | 5 |
| 2G2 10 μg/mL | 25 | 11 |
| 2G2 100 μg/mL | 20 | 4 |
| 9D33 0.001 μg/mL | 17 | −14 |
| 9D33 0.01 μg/mL | 26 | 13 |
| 9D33 0.1 μg/mL | 36 | −13 |
| 9D33 1 μg/mL | 56 | −22 |
| 9D33 10 μg/mL | 81 | 9 |
| 9D33 100 μg/mL | 88 | 18 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17j

TSH induced cyclic AMP production in CHO cells expressing wild type TSHR and TSHR with Lys129 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 748 ± 106 | 710 ± 70 | 95 |
| TSH | 21197 ± 1858 | 11364 ± 1348 | 54 |
| 2G2 1 μg/mL + TSH[b] | 20669 ± 1577 | 13312 ± 424 | 64 |
| 2G2 10 μg/mL + TSH[b] | 21235 ± 2707 | 11279 ± 1786 | 53 |
| 2G2 100 μg/mL + TSH[b] | 20993 ± 1117 | 14886 ± 2848 | 71 |

TABLE 17j-continued

| | | | |
|---|---|---|---|
| 9D33 0.001 μg/mL + TSH[b] | 20299 ± 2578 | 12194 ± 1369 | 60 |
| 9D33 0.01 μg/mL + TSH[b] | 21147 ± 908 | 12452 ± 1342 | 59 |
| 9D33 0.1 μg/mL + TSH[b] | 19098 ± 1944 | 12812 ± 1016 | 67 |
| 9D33 1 μg/mL + TSH[b] | 10880 ± 1530 | 14217 ± 959 | 131 |
| 9D33 10 μg/mL + TSH[b] | 6851 ± 1132 | 12058 ± 80 | 176 |
| 9D33 100 μg/mL + TSH[b] | 3170 ± 713 | 10607 ± 754 | 335 |
| 9D33 100 μg | 1029 ± 120 | 1140 ± 58 | 111 |

B % inhibition results

| Antibody concentration | % inhibition of TSH stimulation[c] Wild type TSHR | Mutated TSHR |
|---|---|---|
| 2G2 1 μg/mL | 2 | −17 |
| 2G2 10 μg/mL | 0 | 0 |
| 2G2 100 μg/mL | 1 | −31 |
| 9D33 0.001 μg/mL | 4 | −7 |
| 9D33 0.01 μg/mL | 0 | −10 |
| 9D33 0.1 μg/mL | 10 | −13 |
| 9D33 1 μg/mL | 49 | −25 |
| 9D33 10 μg/mL | 68 | −6 |
| 9D33 100 μg/mL | 95 | 7 |

[a]Test samples in cyclic AMP assay buffer
[b]TSH final concentration = 1.5 ng/mL
[c]% inhibition =

$$100\times\left(1-\frac{\text{cAMP in presence of test sample}+\text{TSH}}{\text{cAMP in presence of cyclic AMP assay buffer}+\text{TSH}}\right)$$

2G2 is a mouse monoclonal antibody to thyroglobulin (negative control for 9D33)

TABLE 17k

TSH induced cyclic AMP production in CHO cells expressing wild type TSHR and TSHR with Lys129 mutated to Asp. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 412[c] | 401 ± 16 | 97 |
| TSH | 12783 ± 422 | 4914 ± 292 | 38 |
| 2G2 1 μg/mL + TSH[b] | 12434 ± 264 | 5191[c] | 42 |
| 2G2 10 μg/mL + TSH[b] | 11974 ± 467 | 4830 ± 119 | 40 |
| 2G2 100 μg/mL + TSH[b] | 12042 ± 1466 | 4168 ± 45 | 35 |
| 9D33 0.001 μg/mL + TSH[b] | 10568 ± 844 | 5012 ± 134 | 47 |
| 9D33 0.01 μg/mL + TSH[b] | 11833 ± 1266 | 8035[c] | 68 |
| 9D33 0.1 μg/mL + TSH[b] | 9392 ± 1300 | 4905 ± 805 | 52 |
| 9D33 1 μg/mL + TSH[b] | 5031 ± 397 | 6339 ± 823 | 126 |
| 9D33 10 μg/mL + TSH[b] | 2515 ± 278 | 4567 ± 505 | 182 |
| 9D33 100 μg/mL + TSH[b] | 776c | 3346 ± 419 | 431 |
| 9D33 100 μg | 509 ± 46 | 473 ± 102 | 93 |

B % inhibition results

| Antibody concentration | % inhibition of TSH stimulation[d] Wild type TSHR | Mutated TSHR |
|---|---|---|
| 2G2 1 μg/mL | 3 | −6 |
| 2G2 10 μg/mL | 6 | 2 |
| 2G2 100 μg/mL | 6 | 15 |
| 9D33 0.001 μg/mL | 17 | −2 |

TABLE 17k-continued

| | | |
|---|---|---|
| 9D33 0.01 μg/mL | 7 | −64 |
| 9D33 0.1 μg/mL | 27 | 0 |
| 9D33 1 μg/mL | 61 | −29 |
| 9D33 10 μg/mL | 80 | 7 |
| 9D33 100 μg/mL | 94 | 32 |

[a]Test samples in cyclic AMP assay buffer
[b]TSH final concentration = 1.5 ng/mL
[c]mean of duplicate
[d]% inhibition =

$$100\times\left(1-\frac{\text{cAMP in presence of test sample}+\text{TSH}}{\text{cAMP in presence of cyclic AMP assay buffer}+\text{TSH}}\right)$$

2G2 is a mouse monoclonal antibody to thyroglobulin (negative control for 9D33)

TABLE 17l

TSH induced cyclic AMP production in CHO cells expressing wild type TSHR and TSHR with Phe130 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 1019 ± 65 | 915 ± 83 | 90 |
| TSH | 18088 ± 2962 | 11466 ± 995 | 63 |
| 2G2 1 μg/mL + TSH[b] | 15207 ± 1297 | 12415 ± 570 | 82 |
| 2G2 10 μg/mL + TSH[b] | 16741 ± 1303 | 11439 ± 440 | 68 |
| 2G2 100 μg/mL + TSH[b] | 19281 ± 3245 | 12223 ± 895 | 63 |
| 9D33 0.001 μg/mL + TSH[b] | 14911 ± 417 | 10584 ± 1719 | 71 |
| 9D33 0.01 μg/mL + TSH[b] | 15722 ± 693 | 11744 ± 281 | 75 |
| 9D33 0.1 μg/mL + TSH[b] | 14409 ± 810 | 9104 ± 407 | 63 |
| 9D33 1 μg/mL + TSH[b] | 10277 ± 629 | 5212 ± 251 | 51 |
| 9D33 10 μg/mL + TSH[b] | 7116 ± 438 | 3071 ± 421 | 43 |
| 9D33 100 μg/mL + TSH[b] | 3953 ± 523 | 1572 ± 150 | 40 |
| 9D33 100 μg | 1110 ± 43 | 890 ± 78 | 80 |

B % inhibition results

| Antibody concentration | % inhibition of TSH stimulation[c] Wild type TSHR | Mutated TSHR |
|---|---|---|
| 2G2 1 μg/mL | 16 | −8 |
| 2G2 10 μg/mL | 7 | 0 |
| 2G2 100 μg/mL | −7 | −7 |
| 9D33 0.001 μg/mL | 18 | 8 |
| 9D33 0.01 μg/mL | 13 | −2 |
| 9D33 0.1 μg/mL | 20 | 21 |
| 9D33 1 μmL | 43 | 55 |
| 9D33 10 μg/mL | 61 | 73 |
| 9D33 100 μg/mL | 78 | 86 |

[a]Test samples in cyclic AMP assay buffer
[b]TSH final concentration = 1.5 ng/mL
[c]% inhibition =

$$100\times\left(1-\frac{\text{cAMP in presence of test sample}+\text{TSH}}{\text{cAMP in presence of cyclic AMP assay buffer}+\text{TSH}}\right)$$

2G2 is a mouse monoclonal antibody to thyroglobulin (negative control for 9D33)

TABLE 17m

TSH induced cyclic AMP production in CHO cells expressing wild type TSHR and TSHR with Phe134 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 1045 ± 98 | 740 ± 160 | 71 |
| TSH | 19796 ± 1401 | 20249 ± 425 | 102 |
| 2G2 1 μg/mL + TSH[b] | 20013 ± 2808 | 19662 ± 1329 | 98 |
| 2G2 10 μg/mL + TSH[b] | 19219 ± 3257 | 19001 ± 657 | 99 |
| 2G2 100 μg/mL + TSH[b] | 20722 ± 1156 | 20770 ± 594 | 100 |
| 9D33 0.001 μg/mL + TSH[b] | 20420 ± 2123 | 22086 ± 351 | 108 |
| 9D33 0.01 μg/mL + TSH[b] | 18407 ± 1250 | 21142 ± 1984 | 115 |
| 9D33 0.1 μg/mL + TSH[b] | 18571 ± 1082 | 21620 ± 1118 | 116 |
| 9D33 1 μg/mL + TSH[b] | 13342 ± 433 | 21312 ± 1471 | 160 |
| 9D33 10 μg/mL + TSH[b] | 9106 ± 1056 | 16724 ± 1503 | 184 |
| 9D33 100 μg/mLTSH[b] | 4341 ± 1186 | 11788 ± 760 | 272 |
| 9D33 100 μg | 1193 ± 108 | 1149 ± 112 | 96 |

B % inhibition results

| Antibody concentration | % inhibition of TSH stimulation[c] Wild type TSHR | Mutated TSHR |
|---|---|---|
| 2G2 1 μg/mL | −1 | 3 |
| 2G2 10 μg/mL | 3 | 6 |
| 2G2 100 μg/mL | −5 | −3 |
| 9D33 0.001 μg/mL | −3 | −9 |
| 9D33 0.01 μg/mL | 7 | −4 |
| 9D33 0.1 μg/mL | 6 | −7 |
| 9D33 1 μg/mL | 33 | −5 |
| 9D33 10 μg/mL | 54 | 17 |
| 9D33 100 μg/mL | 78 | 42 |

[a]Test samples in cyclic AMP assay buffer
[b]TSH final concentration = 1.5 ng/mL
[c]% inhibition =

$$100\times\left(1-\frac{\text{cAMP in presence of test sample + TSH}}{\text{cAMP in presence of cyclic AMP assay buffer + TSH}}\right)$$

2G2 is a mouse monoclonal antibody to thyroglobulin (negative control for 9D33)

TABLE 17n

TSH induced cyclic AMP production in CHO cells expressing wild type TSHR and TSHR with Asp160 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 521 ± 32 | 483 ± 60 | 93 |
| TSH | 16267 ± 1932 | 12291 ± 1040 | 76 |
| 2G2 1 μg/mL + TSH[b] | 15536 ± 1852 | 13116 ± 693 | 84 |
| 2G2 10 μg/mL + TSH[b] | 14976 ± 1066 | 10613 ± 759 | 71 |
| 2G2 100 μg/mL + TSH[b] | 15211 ± 1303 | 12054 ± 447 | 79 |

TABLE 17n-continued

| Test sample[a] | Wild type TSHR | Mutated TSHR | Mutated/Wild type (%) |
|---|---|---|---|
| 9D33 0.001 μg/mL + TSH[b] | 12507 ± 1070 | 14316 ± 554 | 114 |
| 9D33 0.01 μg/mL + TSH[b] | 14146 ± 50 | 11125 ± 1618 | 79 |
| 9D33 0.1 μg/mL + TSH[b] | 13139 ± 526 | 1312 ± 116 | 10 |
| 9D33 1 μg/m TSH[b] | 10290[c] | 985 ± 285 | 10 |
| 9D33 10 μg/mL + TSH[b] | 3445 ± 491 | 796 ± 135 | 23 |
| 9D33 100 μg/mL + TSH[b] | 2211 ± 125 | 752 ± 82 | 34 |
| 9D33 100 μg | 498 ± 3 | 539 ± 53 | 108 |

B % inhibition results

| Antibody concentration | % inhibition of TSH stimulation[d] Wild type TSHR | Mutated TSHR |
|---|---|---|
| 2G2 1 μg/mL | 4 | −7 |
| 2G2 10 μg/mL | 8 | 14 |
| 2G2 100 μg/mL | 6 | 2 |
| 9D33 0.001 μg/mL | 23 | −16 |
| 9D33 0.01 μg/mL | 13 | 9 |
| 9D33 0.1 μg/mL | 19 | 89 |
| 9D33 1 μg/mL | 63 | 92 |
| 9D33 10 μg/mL | 79 | 94 |
| 9D33 100 μg/mL | 86 | 94 |

[a]Test samples in cyclic AMP assay buffer
[b]TSH final concentration = 1.5 ng/mL
[c]mean of duplicate
[d]% inhibition =

$$100\times\left(1-\frac{\text{cAMP in presence of test sample + TSH}}{\text{cAMP in presence of cyclic AMP assay buffer + TSH}}\right)$$

2G2 is a mouse monoclonal antibody to thyroglobulin (negative control for 9D33)

TABLE 17o

TSH induced cyclic AMP production in CHO cells expressing wild type TSHR and TSHR with Lys183 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/Wild type (%) |
|---|---|---|---|
| Cyclic AMP assay buffer only | 371 ± 17 | 264 ± 29 | 71 |
| TSH | 13792 ± 1706 | 12173 ± 3906 | 88 |
| 2G2 1 μg/mL + TSH[b] | 9996 ± 1289 | 14200 ± 5323 | 142 |
| 2G2 10 μg/mL + TSH[b] | 12279 ± 2013 | 10616 ± 2142 | 86 |
| 2G2 100 μg/mL + TSH[b] | 10520 ± 1450 | 12789 ± 902 | 122 |
| 9D33 0.001 μg/mL + TSH[b] | 10372[c] | 13874 ± 1472 | 134 |
| 9D33 0.01 μg/mL + TSH[b] | 12431 ± 2262 | 17223 ± 6145 | 139 |
| 9D33 0.1 μg/mL + TSH[b] | 9470 ± 865 | 14012 ± 1217 | 148 |
| 9D33 1 μg/mL + TSH[b] | 2920 ± 597 | 10713 ± 3015 | 367 |
| 9D33 10 μg/mL + TSH[b] | 2828 ± 744 | 3857 ± 316 | 136 |
| 9D33 100 μg/mL + TSH[b] | 2210 ± 391 | 3220 ± 261 | 146 |
| 9D33 100 μg | 260 ± 76 | 320 ± 12 | 123 |

B % inhibition results

| Antibody concentration | % inhibition of TSH stimulation[d] Wild type TSHR | Mutated TSHR |
|---|---|---|
| 2G2 1 μg/mL | 28 | −17 |
| 2G2 10 μg/mL | 11 | 13 |
| 2G2 100 μg/mL | 24 | −5 |

TABLE 17o-continued

| | | |
|---|---|---|
| 9D33 0.001 μg/mL | 25 | −14 |
| 9D33 0.01 μg/mL | 10 | −42 |
| 9D33 0.1 μg/mL | 31 | −15 |
| 9D33 1 μg/mL | 79 | 12 |
| 9D33 10 μg/mL | 79 | 68 |
| 9D33 100 μg/mL | 84 | 74 |

[a]Test samples in cyclic AMP assay buffer
[b]TSH final concentration = 0.3 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17p

TSH induced cyclic AMP production in CHO cells expressing wild type TSHR and TSHR with Lys183 mutated to Asp. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 346 ± 47 | 405 ± 38 | 117 |
| TSH | 8666 ± 185 | 5131 ± 788 | 59 |
| 2G2 1 μg/mL + TSH[b] | 8025 ± 514 | 3993 ± 499 | 50 |
| 2G2 10 μg/mL + TSH[b] | 9382 ± 722 | 4641 ± 1139 | 49 |
| 2G2 100 μg/mL + TSH[b] | 6810 ± 871 | 4838 ± 543 | 71 |
| 9D33 0.001 μg/mL + TSH[b] | 6931 ± 631 | 4903 ± 880 | 70 |
| 9D33 0.01 μg/mL + TSH[b] | 7419 ± 989 | 3778 ± 300 | 51 |
| 9D33 0.1 μg/mL + TSH[b] | 6250 ± 208 | 4025 ± 1208 | 64 |
| 9D33 1 g/mL + TSH[b] | 3686 ± 390 | 2757 ± 297 | 75 |
| 9D33 10 μg/mL + TSH[b] | 2197 ± 141 | 1818 ± 233 | 83 |
| 9D33 100 μg/mL + TSH[b] | 1293 ± 113 | 1294 ± 177 | 100 |
| 9D33 100 μg | 437 ± 30 | 294 ± 46 | 67 |

B % inhibition results

| Antibody concentration | % inhibition of TSH stimulation[c] Wild type TSHR | Mutated TSHR |
|---|---|---|
| 2G2 1 μg/mL | 7 | 22 |
| 2G2 10 μg/mL | −8 | 10 |
| 2G2 100 μg/mL | 21 | 6 |
| 9D33 0.001 μg/mL | 20 | 4 |
| 9D33 0.01 μg/mL | 14 | 26 |
| 9D33 0.1 μg/mL | 28 | 22 |
| 9D33 1 μg/mL | 57 | 46 |
| 9D33 10 μg/mL | 75 | 65 |
| 9D33 100 μg/ml | 85 | 75 |

[a]Test samples in cyclic AMP assay buffer
[b]TSH final concentration = 1.5 ng/mL
[c]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17q

TSH induced cyclic AMP production in CHO cells expressing wild type TSHR and TSHR with Tyr185 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 33[c] | 118 ± 60 | 358 |
| TSH | 8951 ± 1717 | 4807 ± 518 | 54 |
| 2G2 1 μg/mL + TSH[b] | 9852 ± 2211 | 4219 ± 193 | 43 |
| 2G2 10 μg/mL + TSH[b] | 10415 ± 1974 | 5199 ± 1202 | 50 |
| 2G2 100 μg/mL + TSH[b] | 10829 ± 2611 | 5153 ± 1552 | 48 |
| 9D33 0.001 μg/mL + TSH[b] | 11064 ± 2932 | 5476 ± 216 | 49 |
| 9D33 0.01 μg/mL + TSH[b] | 9945 ± 366 | 5437 ± 632 | 55 |
| 9D33 0.1 μg/mL + TSH[b] | 10451 ± 299 | 3132 ± 251 | 30 |
| 9D33 1 μg/mL + TSH[b] | 2849 ± 627 | 1717 ± 219 | 60 |
| 9D33 10 μg/mL + TSH[b] | 1955 ± 582 | 1038 ± 27 | 53 |
| 9D33 100 μg/mL + TSH[b] | 1263 ± 204 | 614 ± 329 | 49 |
| 9D33 100 μg | 103 ± 106 | 178 ± 18 | 173 |

B % inhibition results

| Antibody concentration | % inhibition of TSH stimulation[d] Wild type TSHR | Mutated TSHR |
|---|---|---|
| 2G2 1 μg/mL | −10 | 12 |
| 2G2 10 μg/mL | −16 | −8 |
| 2G2 100 μg/mL | −20 | −7 |
| 9D33 0.001 μg/mL | −24 | −14 |
| 9D33 0.01 μg/mL | −11 | −13 |
| 9D33 0.1 μg/mL | −17 | 35 |
| 9D33 1 μg/mL | 68 | 64 |
| 9D33 10 μg/mL | 78 | 78 |
| 9D33 100 μg/mL | 86 | 87 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17r

TSH induced cyclic AMP production in CHO cells expressing wild type TSHR and TSHR with Tyr206 mutated to Ala. Effect of different dilutions of monoclonal antibody to the TSH receptor (9D33) with TSH antagonist activity A Cyclic AMP levels

| Test sample[a] | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 125 ± 13 | 127 ± 39 | 102 |
| TSH | 7714 ± 372 | 6022 ± 922 | 78 |
| 2G2 1 μg/mL + TSH[b] | 9832 ± 2099 | 7272 ± 732 | 74 |
| 2G2 10 μg/mL + TSH[b] | 6648 ± 859 | 6423 ± 781 | 97 |
| 2G2 100 μg/mL + TSH[b] | 9666 ± 1599 | 6251 ± 289 | 65 |

TABLE 17r-continued

| | | | |
|---|---|---|---|
| 9D33 0.001 µg/mL + TSH[b] | 7654 ± 1675 | 6523 ± 485 | 85 |
| 9D33 0.01 µg/mL + TSH[b] | 7699 ± 770 | 7540 ± 1313 | 98 |
| 9D33 0.1 µg/mL + TSH[b] | 8113 ± 222 | 3392 ± 190 | 42 |
| 9D33 1 µg/mL + TSH[b] | 2495 ± 581 | 1439 ± 466 | 58 |
| 9D33 10 µg/mL + TSH[b] | 2487 ± 396 | 776 ± 128 | 31 |
| 9D33 100 µg/mL + TSH[b] | 920 ± 210 | 832 ± 207 | 90 |
| 9D33 100 µg | 117 ± 31 | 132 ± 10 | 113 |

B % inhibition results

| | % inhibition of TSH stimulation[c] | |
|---|---|---|
| Antibody concentration | Wild type TSHR | Mutated TSHR |
| 2G2 1 µg/mL | −27 | −21 |
| 2G2 10 µg/mL | 14 | −7 |
| 2G2 100 µg/mL | −25 | −4 |
| 9D33 0.001 µg/mL | 1 | −8 |
| 9D33 0.01 µg/mL | 0 | −25 |
| 9D33 0.1 µg/mL | −5 | 44 |
| 9D33 1 µg/mL | 68 | 76 |
| 9D33 10 µg/mL | 68 | 87 |
| 9D33 100 µg/mL | 88 | 86 |

[a]Test samples in cyclic AMP assay buffer
[b]TSH final concentration = 1.5 ng/mL
[c]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17s

TSH induced cyclic AMP production in CHO cells expressing wild type TSHR and TSHR with Lys209 mutated to Ala. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ Wild |
|---|---|---|---|
| Test sample[a] | Wild type TSHR | Mutated TSHR | type (%) |
| Cyclic AMP assay buffer only | 638 ± 46 | 173 ± 26 | 27 |
| TSH | 14724 ± 601 | 5685 ± 1592 | 39 |
| 2G2 1 µg/mL + TSH[b] | 15078 ± 2313 | 10707 ± 2563 | 71 |
| 2G2 10 µg/mL + TSH[b] | 16435 ± 427 | 11223 ± 2495 | 68 |
| 2G2 100 µg/mL + TSH[b] | 17412[c] | 7649 ± 1735 | 44 |
| 9D33 0.001 µg/mL + TSH[b] | 13867[c] | 8335 ± 691 | 60 |
| 9D33 0.01 µg/mL + TSH[b] | 19164 ± 1515 | 7447 ± 3118 | 39 |
| 9D33 0.1 µg/mL + TSH[b] | 18410[c] | 5547 ± 2107 | 30 |
| 9D33 1 µg/mL + TSH[b] | 7982 ± 1605 | 1292 ± 512 | 16 |
| 9D33 10 µg/mL + TSH[b] | 3503 ± 1401 | 772 ± 89 | 22 |
| 9D33 100 µg/mL + TSH[b] | 964 ± 474 | 710 ± 148 | 74 |
| 9D33 100 µg | 529 ± 22 | 860 ± 212 | 163 |

B % inhibition results

| | % inhibition of TSH stimulation[d] | |
|---|---|---|
| Antibody concentration | Wild type TSHR | Mutated TSHR |
| 2G2 1 µg/mL | 2 | −88 |
| 2G2 10 µg/mL | −12 | −97 |
| 2G2 100 µg/mL | −18 | −35 |
| 9D33 0.001 µg/mL | 6 | −47 |

TABLE 17s-continued

| | | |
|---|---|---|
| 9D33 0.01 µg/mL | −30 | −31 |
| 9D33 0.1 µg/mL | −25 | 2 |
| 9D33 1 µg/mL | 54 | 77 |
| 9D33 10 µg/mL | 76 | 86 |
| 9D33 100 µg/mL | 93 | 88 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17t

TSH induced cyclic AMP production in CHO cells expressing wild type TSHR and TSHR with Lys250 mutated to Ala. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ Wild |
|---|---|---|---|
| Test sample[a] | Wild type TSHR | Mutated TSHR | type (%) |
| Cyclic AMP assay buffer only | 1068 ± 164 | 1491 ± 182 | 140 |
| TSH | 22245[c] | 15844 ± 2736 | 71 |
| 2G2 1 µg/mL + TSH[b] | 19749 ± 2395 | 21309 ± 1640 | 108 |
| 2G2 10 µg/mL + TSH[b] | 17609 ± 981 | 13048 ± 1718 | 74 |
| 2G2 100 µg/mL + TSH[b] | 22060 ± 2265 | 17966 ± 1997 | 81 |
| 9D33 0.001 µg/mL + TSH[b] | 21265 ± 375 | 19697 ± 2129 | 93 |
| 9D33 0.01 µg/mL + TSH[b] | 21435 ± 3957 | 24374 ± 4050 | 114 |
| 9D33 0.1 µg/mL + TSH[b] | 16626 ± 1019 | 20358 ± 2627 | 122 |
| 9D33 1 µg/mL + TSH[b] | 10260 ± 1863 | 17657 ± 2149 | 172 |
| 9D33 10 µg/mL + TSH[b] | 7115 ± 1337 | 9725 ± 1349 | 137 |
| 9D33 100 µg/mL + TSH[b] | 2012[c] | 6387 ± 916 | 317 |
| 9D33 100 µg | 1349 ± 122 | 1714 ± 144 | 127 |

B % inhibition results

| | % inhibition of TSH stimulation[d] | |
|---|---|---|
| Antibody concentration | Wild type TSHR | Mutated TSHR |
| 2G2 1 µg/mL | 11 | −34 |
| 2G2 10 µg/mL | 21 | 18 |
| 2G2 100 µg/mL | 1 | −13 |
| 9D33 0.001 µg/mL | 4 | −24 |
| 9D33 0.01 µg/mL | 4 | −54 |
| 9D33 0.1 µg/mL | 25 | −28 |
| 9D33 1 µg/mL | 54 | −11 |
| 9D33 10 µg/mL | 68 | 39 |
| 9D33 100 µg/mL | 91 | 60 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17u

TSH induced cyclic AMP production in CHO cells expressing wild type TSHR and TSHR with Glu251 mutated to Ala. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ Wild |
|---|---|---|---|
| Test sample[a] | Wild type TSHR | Mutated TSHR | type (%) |
| Cyclic AMP assay buffer only | 636 ± 116 | 779 ± 119 | 122 |
| TSH | 23009 ± 3972 | 11398 ± 2719 | 50 |
| 2G2 1 μg/mL + TSH[b] | 17299 ± 1029 | 18350[c] | 106 |
| 2G2 10 μg/mL + TSH[b] | 18521 ± 472 | 11028 ± 839 | 60 |
| 2G2 100 μg/mL + TSH[b] | 17147[c] | 6999 ± 631 | 41 |
| 9D33 0.001 μg/mL + TSH[b] | 19901[c] | 12930 ± 1264 | 65 |
| 9D33 0.01 μg/mL + TSH[b] | 15319 ± 2933 | 17445 ± 1677 | 114 |
| 9D33 0.1 μg/mL + TSH[b] | 18030 ± 4806 | 8723 ± 1100 | 48 |
| 9D33 1 μg/mL + TSH[b] | 7108 ± 1592 | 4776 ± 933 | 67 |
| 9D33 10 μg/mL + TSH[b] | 4059 ± 704 | 2300 ± 680 | 57 |
| 9D33 100 μg/mL + TSH[b] | 1809 ± 1090 | 1546 ± 614 | 85 |
| 9D33 100 μg | 718 ± 122 | 954 ± 49 | 133 |

B % inhibition results

| | % inhibition of TSH stimulation[d] | |
|---|---|---|
| Antibody concentration | Wild type TSHR | Mutated TSHR |
| 2G2 1 μg/mL | 25 | −61 |
| 2G2 10 μg/mL | 20 | −3 |
| 2G2 100 μg/mL | 25 | 39 |
| 9D33 0.001 μg/mL | 14 | −13 |
| 9D33 0.01 μg/mL | 33 | −53 |
| 9D33 0.1 μg/mL | 22 | 23 |
| 9D33 1 μg/mL | 69 | 58 |
| 9D33 10 μg/mL | 82 | 80 |
| 9D33 100 μg/mL | 92 | 86 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 17v

TSH induced cyclic AMP production in CHO cells expressing wild type TSHR and TSHR with Arg274 mutated to Ala. Effect of different dilutions of monoclonal antibody to the TSH receptor (9D33) with TSH antagonist activity A Cyclic AMP levels

| | Cyclic AMP produced (fmol/cell well) (mean ± SD; n = 3) | | Mutated/ Wild |
|---|---|---|---|
| Test sample[a] | Wild type TSHR | Mutated TSHR | type (%) |
| Cyclic AMP assay buffer only | 621 ± 37 | 157[c] | 25 |
| TSH | 5355 ± 1126 | 3335[c] | 62 |
| 2G2 1 μg/mL + TSH[b] | 4032[c] | 4830[c] | 120 |
| 2G2 10 μg/mL + TSH[b] | 4399 ± 504 | 3099 ± 407 | 70 |
| 2G2 100 μg/mL + TSH[b] | 4247[c] | 3292 ± 271 | 78 |
| 9D33 0.001 μg/mL + TSH[b] | 3663 ± 310 | 4012 ± 591 | 110 |

TABLE 17v-continued

| | | | |
|---|---|---|---|
| 9D33 0.01 μg/mL + TSH[b] | 3881 ± 459 | 4330 ± 631 | 112 |
| 9D33 0.1 μg/mL + TSH[b] | 4788 ± 1443 | 721 ± 111 | 15 |
| 9D33 1 μg/mL + TSH[b] | 741 ± 104 | 169 ± 3 | 23 |
| 9D33 10 μg/mL + TSH[b] | 885[c] | 145[c] | 16 |
| 9D33 100 μg/mL + TSH[b] | 645 ± 53 | 131[c] | 20 |
| 9D33 100 μg | 637[c] | 710 ± 23 | 111 |

B % inhibition results

| | % inhibition of TSH stimulation[d] | |
|---|---|---|
| Antibody concentration | Wild type TSHR | Mutated TSHR |
| 2G2 1 μg/mL | 25 | −45 |
| 2G2 10 μg/mL | 18 | 7 |
| 2G2 100 μg/mL | 21 | 1 |
| 9D33 0.001 μg/mL | 32 | −20 |
| 9D33 0.01 μg/mL | 28 | −30 |
| 9D33 0.1 μg/mL | 11 | 78 |
| 9D33 1 μg/mL | 86 | 95 |
| 9D33 10 μg/mL | 83 | 96 |
| 9D33 100 μg/mL | 88 | 96 |

[a]Test samples in cyclic AMP assay buffer
[b]TSH final concentration = 1.5 ng/mL
[c]mean of duplicate
[d]% inhibition =

$$100 \times \left(1 - \frac{\text{cAMP in presence of test sample} + \text{TSH}}{\text{cAMP in presence of cyclic AMP assay buffer} + \text{TSH}}\right)$$

2G2 is a mouse monoclonal antibody to thyroglobulin (negative control for 9D33)

TABLE 18

Summary of effects of mutation (relative to wild type) on inhibition of TSH mediated cyclic AMP stimulation by the mouse monoclonal antibody 9D33

| aa mutation | Inhibition of TSH mediated cyclic AMP stimulation by 9D33 |
|---|---|
| Lys58 to Ala | marked reduction |
| Ile60 to Ala | no effect |
| Arg80 to Ala | marked reduction |
| Arg80 to Asp | marked reduction |
| Tyr82 to Ala | marked reduction |
| Glu107 to Ala | no effect |
| Glu107 to Arg | marked reduction |
| Arg109 to Ala | marked reduction |
| Arg109 to Asp | marked reduction |
| Lys129 to Ala | marked reduction |
| Lys129 to Asp | marked reduction |
| Phe130 to Ala | no effect |
| Phe134 to Ala | marked reduction |
| Asp160 to Ala | enhanced effect |
| Lys183 to Ala | no effect |
| Lys183 to Asp | no effect |
| Tyr185 to Ala | no effect |
| Tyr206 to Ala | no effect |
| Lys209 to Ala | no effect |
| Lys250 to Ala | some reduction |
| Glu251 to Ala | no effect |
| Arg255 to Asp | enhanced effect |
| Arg274 to Ala | enhanced effect |

TABLE 19a

Stimulation of cyclic AMP production by 8 sera from patients with Graves' disease in CHO cells expressing wild type TSHR and TSHR with Arg80 mutated to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 720 ± 122 | 1003 ± 85 | 139 |
| HBD pool | 787 ± 125 | 848 ± 153 | 108 |
| G1 | 14546 ± 1913 | 10329 ± 1326 | 71 |
| G9 | 9192[a] | 633 ± 36 | 7 |
| G15 | 10180 ± 1530 | 5538 ± 958 | 54 |
| G17 | 6592 ± 291 | 6897 ± 77 | 105 |
| G19 | 9042 ± 1407 | 6907 ± 621 | 76 |
| G20 | 11821 ± 1569 | 1895 ± 702 | 16 |
| G21 | 11951 ± 1402 | 11911 ± 2267 | 100 |
| G22 | 10877 ± 752 | 12125 ± 2063 | 111 |
| TSH (3 ng/mL) | 12439 ± 1630 | 18231 ± 1357 | 147 |
| hMAb TSHR1 Fab (10 ng/mL) | 15900 ± 1903 | 965 ± 164 | 6 |

[a]mean of duplicate
HBD = pool of healthy blood donor sera.
G1-G23 = sera from patients with Graves' disease TABLE 19b Stimulation of cyclic AMP production by 8 sera from patients with Graves' disease in CHO cells expressing wild type TSHR and TSHR with Arg80 mutated to Asp

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 645 ± 99 | 1208 ± 141 | 187 |
| HBD pool | 496 ± 78 | 1150 ± 206 | 232 |
| G1 | 23914 ± 3837 | 9108 ± 130 | 38 |
| G9 | 14026 ± 2339 | 434[a] | 3 |
| G15 | 9131[a] | 2592 ± 1027 | 28 |
| G17 | 6311 ± 545 | 7947 ± 733 | 126 |
| G19 | 10232 ± 1812 | 8840 ± 135 | 86 |
| G20 | 7893 ± 359 | 1670 ± 275 | 21 |
| G21 | 11033 ± 1326 | 12006 ± 1256 | 109 |
| G22 | 14261 ± 686 | 15182 ± 2888 | 106 |
| TSH (3 ng/mL) | 26172 ± 3344 | 18825 ± 1323 | 72 |
| hMAb TSHR1 Fab (10 ng/mL) | 22054 ± 1743 | 830 ± 44 | 4 |

[a]mean of duplicate
HBD = pool of healthy blood donor sera.
G1-G23 = sera from patients with Graves' disease TABLE 19c Stimulation of cyclic AMP production by 8 sera from patients with Graves' disease in CHO cells expressing wild type TSHR and TSHR with Glu107 mutated to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 467 ± 55 | 1044 ± 120 | 224 |
| HBD pool | 349 ± 31 | 563 ± 16 | 161 |
| G1 | 24022 ± 2266 | 11449 ± 1745 | 48 |
| G2 | 10291 ± 2092 | 9515 ± 1660 | 92 |

TABLE 19c-continued

Stimulation of cyclic AMP production by 8 sera from patients with Graves' disease in CHO cells expressing wild type TSHR and TSHR with Glu107 mutated to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| G3 | 1750 ± 89 | 945 ± 68 | 54 |
| G4 | 5654 ± 902 | 630 ± 105 | 11 |
| G5 | 1997 ± 429 | 841 ± 90 | 42 |
| G6 | 8862 ± 648 | 2741 ± 502 | 31 |
| G7 | 8524 ± 1333 | 563 ± 9 | 7 |
| G10 | 1072 ± 78 | 862 ± 57 | 80 |
| TSH (3 ng/mL) | 21689 ± 4541 | 14393 ± 3517 | 66 |
| hMAb TSHR1 Fab (10 ng/mL) | 20193[a] | 1269 ± 214 | 6 |

[a]mean of duplicate
HBD = pool of healthy blood donor sera.
G1-G23 = sera from patients with Graves' disease TABLE 19d Stimulation of cyclic AMP production by 8 sera from patients with Graves' disease in CHO cells expressing wild type TSHR and TSHR with Arg109 mutated to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 1109 ± 216 | 837 ± 166 | 75 |
| HBD pool | 469 ± 68 | 538 ± 156 | 115 |
| G1 | 20487 ± 2394 | 18398 ± 2682 | 90 |
| G11 | 1541 ± 40 | 471 ± 116 | 31 |
| G15 | 12402 ± 671 | 6619[a] | 53 |
| G16 | 2382 ± 166 | 508[a] | 21 |
| G17 | 8351 ± 142 | 240[a] | 3 |
| G18 | 2160[a] | 271 ± 33 | 13 |
| G19 | 11235 ± 1167 | 7134 ± 458 | 63 |
| G20 | 10485 ± 1872 | 5486 ± 231 | 52 |
| TSH (3 ng/mL) | 22177 ± 3724 | 18545 ± 1365 | 84 |
| hMAb TSHR1 Fab (10 ng/mL) | 18509 ± 1980 | 8835[a] | 48 |

[a]mean of duplicate
HBD = pool of healthy blood donor sera.
G1-G23 = sera from patients with Graves' disease TABLE 19e Stimulation of cyclic AMP production by 8 sera from patients with Graves' disease in CHO cells expressing wild type TSHR and TSHR with Arg109 mutated to Asp

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 1164 ± 135 | 156 ± 17 | 13 |
| HBD pool | 684 ± 9 | 142[a] | 21 |
| G1 | 13261 ± 1829 | 12183 ± 440 | 92 |
| G9 | 10959 ± 1289 | 3985 ± 714 | 36 |
| G15 | 10163 ± 1093 | 2895 ± 372 | 28 |
| G17 | 8802 ± 1300 | ud | nd |
| G19 | 9120 ± 1226 | 7588 ± 261 | 83 |
| G20 | 9028 ± 0 | 774 ± 170 | 9 |
| G21 | 11249 ± 665 | 2711 ± 47 | 24 |

TABLE 19e-continued

Stimulation of cyclic AMP production by 8 sera from patients with Graves' disease in CHO cells expressing wild type TSHR and TSHR with Arg109 mutated to Asp

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| G22 | 10929 ± 605 | 592 ± 159 | 5 |
| TSH (3 ng/mL) | 13087 ± 1240 | 12308 ± 500 | 94 |
| hMAb TSHR1 Fab (10 ng/mL) | 12318 ± 513 | 29701[a] | 24 |

[a]mean of duplicate
HBD = pool of healthy blood donor sera.
G1-G23 = sera from patients with Graves' disease
ud = undetectable
nd = not determined TABLE 19f Stimulation of cyclic AMP production by 8 sera from patients with Graves' disease in CHO cells expressing wild type TSHR and TSHR with Lys129 mutated to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 733 ± 130 | 774 ± 116 | 106 |
| HBD pool | 555 ± 82 | 676 ± 63 | 122 |
| G1 | 14504 ± 1914 | 12217 ± 1309 | 84 |
| G9 | 11371 ± 1268 | 6705 ± 490 | 59 |
| G15 | 8331 ± 413 | 5896 ± 841 | 71 |
| G17 | 6769 ± 1311 | 3642 ± 534 | 54 |
| G19 | 6232[a] | 5588 ± 433 | 90 |
| G20 | 6974 ± 416 | 4561[a] | 65 |
| G21 | 9638 ± 923 | 6384 ± 717 | 66 |
| G22 | 11167 ± 849 | 8579 ± 1015 | 77 |
| TSH (3 ng/mL) | 12021 ± 597 | 10747 ± 1097 | 89 |
| hMAb TSHR1 Fab (10 ng/mL) | 15281 ± 2616 | 5457 ± 294 | 36 |

[a]mean of duplicate
HBD = pool of healthy blood donor sera.
G1-G23 = sera from patients with Graves' disease TABLE 19g Stimulation of cyclic AMP production by 8 sera from patients with Graves' disease in CHO cells expressing wild type TSHR and TSHR with Lys183 mutated to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Experiment 1 | | | |
| Cyclic AMP assay buffer only | 564[a] | 501 ± 30 | 89 |
| HBD pool | 388 ± 7 | 423 ± 83 | 109 |
| G1 | 20190[a] | 13292 ± 1339 | 66 |
| G2 | 11793 ± 1112 | 4213 ± 350 | 36 |
| G3 | 3406 ± 149 | 2699 ± 246 | 79 |
| G4 | 3465 ± 102 | 2473 ± 302 | 71 |
| G5 | 3850 ± 297 | 4540[a] | 118 |
| G6 | 2702 ± 76 | 2148 ± 262 | 79 |
| G7 | 3666 ± 72 | 11567 ± 604 | 316 |
| G10 | 3682 ± 136 | 9445[a] | 257 |

TABLE 19g-continued

Stimulation of cyclic AMP production by 8 sera from patients with Graves' disease in CHO cells expressing wild type TSHR and TSHR with Lys183 mutated to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| TSH (3 ng/mL) | 15633 ± 1329 | 15528 ± 2057 | 99 |
| hMAb TSHR1 Fab (10 ng/mL) | 12921 ± 1927 | 2685 ± 166 | 21 |
| Experiment 2 | | | |
| Cyclic AMP assay buffer only | 609 ± 103 | 824 ± 115 | 135 |
| HBD | 767[a] | 847 ± 82 | 110 |
| G7 | 8582 ± 919 | 21820 ± 3119 | 254 |
| G10 | 6900 ± 1020 | 11315 ± 582 | 164 |
| TSH (3 ng/mL) | 6652 ± 507 | 10158[a] | 153 |

[a]mean of duplicate
HBD = pool of healthy blood donor sera.
G1-G23 = sera from patients with Graves' disease TABLE 19h Stimulation of cyclic AMP production by 8 sera from patients with Graves' disease in CHO cells expressing wild type TSHR and TSHR with Lys183 mutated to Asp

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 1177 ± 84 | 1060 ± 129 | 90 |
| HBD pool | 1083 ± 90 | 818 ± 87 | 76 |
| G1 | 23805 ± 711 | 16885 ± 3813 | 71 |
| G2 | 15218 ± 742 | 5498 ± 463 | 36 |
| G3 | 6751 ± 299 | 2222[a] | 33 |
| G4 | 8658[a] | 1891 ± 383 | 21 |
| G5 | 9597 ± 880 | 5432 ± 502 | 57 |
| G6 | 6452 ± 251 | 6751 ± 295 | 105 |
| G7 | 9408 ± 1016 | 8245 ± 1419 | 88 |
| G10 | 10221 ± 634 | 5346 ± 794 | 52 |
| TSH (3 ng/mL) | 20683 ± 1193 | 20430 ± 1646 | 99 |
| hMAb TSHR1 Fab (10 ng/mL) | 21674 ± 6631 | 2288 ± 332 | 11 |

[a]mean of duplicate
HBD = pool of healthy blood donor sera.
G1-G23 = sera from patients with Graves' disease TABLE 19i Stimulation of cyclic AMP production by 8 sera from patients with Graves' disease in CHO cells expressing wild type TSHR and TSHR with double mutation Arg255 to Ala and Trp258 to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| Cyclic AMP assay buffer only | 971 ± 158 | 852 ± 39 | 88 |
| HBD pool | 195 ± 15 | 192 ± 11 | 98 |
| G1 | 23823 ± 3713 | 10040[a] | 42 |
| G15 | 16707[a] | 988 ± 184 | 6 |
| G16 | 5936[a] | 284 ± 56 | 5 |
| G18 | 4188 ± 249 | 539 ± 54 | 13 |
| G19 | 9319 ± 2112 | 1166 ± 187 | 13 |

TABLE 19i-continued

Stimulation of cyclic AMP production by 8 sera from patients with Graves' disease in CHO cells expressing wild type TSHR and TSHR with double mutation Arg255 to Ala and Trp258 to Ala

| Test sample in cyclic AMP assay buffer | Cyclic AMP produced (fmol/cell well) mean ± SD (n = 3) Wild type TSHR | Mutated TSHR | Mutated/Wild type (%) |
|---|---|---|---|
| G21 | 18524[a] | 1131 ± 90 | 6 |
| G22 | 20146 ± 599 | 10350[a] | 51 |
| G23 | 3135 ± 965 | 614 ± 112 | 20 |
| TSH (3 ng/mL) | 22914 ± 3567 | 21673 ± 2216 | 95 |
| hMAb TSHR1 Fab (10 ng/mL) | 22605 ± 2137 | 1228 ± 48 | 5 |

[a]mean of duplicate

HBD = pool of healthy blood donor sera.

G1-G23 = sera from patients with Graves' disease

TABLE 20

Summary of effect of mutation (relative to wild type) on stimulation of cyclic AMP production by sera (n = 8) from patients with Graves' disease

| aa mutation | marked reduction | reduction | small effect | no effect | enhanced effect |
|---|---|---|---|---|---|
| Arg80 to Ala | 2/8 | 1/8 | 2/8 | 3/8 | 0/8 |
| Arg80 to Asp | 3/8 | 1/8 | 1/8 | 3/8 | 0/8 |
| Glu107 to Ala | 2/8 | 4/8 | 1/8 | 1/8 | 0/8 |
| Arg109 to Ala | 3/8 | 3/8 | 1/8 | 1/8 | 0/8 |
| Arg109 to Asp | 5/8 | 1/8 | 1/8 | 1/8 | 0/8 |
| Lys129 to Ala | 0/8 | 2/8 | 5/8 | 1/8 | 0/8 |
| Lys183 to Ala | 0/8 | 1/8 | 4/8 | 1/8 | 2/8 |
| Lys183 to Asp | 1/8 | 4/8 | 2/8 | 1/8 | 0/8 |
| Arg255 to Asp | 8/8 | 0/8 | 0/8 | 0/8 | 0/8 |
| Arg255 to Ala and Trp258 to Ala | 6/8 | 2/8 | 0/8 | 0/8 | 0/8 |

Number of sera affected/out of 8 sera tested for each mutation is shown.

TABLE 21a

Stimulation of cyclic AMP production by 6 different mouse thyroid stimulating monoclonal antibodies (mTSMAbs) in CHO cells expressing wild type TSHR and TSHR with Arg80 mutated to Asp.

| Test sample in cyclic AMP assay buffer | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 484 ± 74 | 880 ± 142 | 182 |
| hMAb TSHR1 (10 ng/mL) | 15218 ± 1052 | 1284 ± 469 | 8 |
| 2G2 (1 μg/mL) | 726 ± 164 | 946 ± 207 | 130 |
| TSMAb 1 (1 μg/mL) | 4862 ± 510 | 1480 ± 160 | 30 |
| TSMAb 2 (1 μg/mL) | 3390 ± 459 | 945 ± 200 | 28 |
| TSMAb C (10 ng/mL) | 5261 ± 472 | 1532 ± 320 | 29 |
| TSMAb D (1 μg/mL) | 6714 ± 398 | 1255 ± 316 | 19 |
| TSMAb E (1 μg/mL) | 6861 ± 1025 | 1083 ± 199 | 16 |
| TSMAb F (100 ng/mL) | 11271 ± 1753 | 1424 ± 279 | 13 |

2G2 is a mouse monoclonal antibody to thyroglobulin (negative control)

TABLE 21b

Stimulation of cyclic AMP production by 6 different mouse thyroid stimulating monoclonal antibodies (mTSMAbs) in CHO cells expressing wild type TSHR and TSHR with Glu107 mutated to Ala.

| Test sample in cyclic AMP assay buffer | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 470 ± 85 | 1130 ± 119 | 240 |
| hMAb TSHR1 (10 ng/mL) | 19175[a] | 1238 ± 15 | 6 |
| 2G2 (1 μg/mL) | 632 ± 214 | 1057 ± 129 | 167 |
| TSMAb 1 (1 μg/mL) | 5986 ± 374 | 1049 ± 170 | 18 |
| TSMAb 2 (1 μg/mL) | 4214 ± 448 | 1106 ± 105 | 26 |
| TSMAb C (10 ng/mL) | 7181 ± 678 | 1267 ± 140 | 18 |
| TSMAb D (1 μg/mL) | 10157[a] | 1149 ± 120 | 11 |
| TSMAb E (1 μg/mL) | 7425[a] | 1224 ± 50 | 16 |
| TSMAb F (100 ng/mL) | 13203 ± 891 | 1158 ± 137 | 9 |

[a]mean of duplicate

2G2 is a mouse monoclonal antibody to thyroglobulin (negative control)

TABLE 21c

Stimulation of cyclic AMP production by 6 different mouse thyroid stimulating monoclonal antibodies (mTSMAbs) in CHO cells expressing wild type TSHR and TSHR with Arg109 mutated to Ala.

| Test sample in cyclic AMP assay buffer | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 727 ± 41 | 1036 ± 190 | 143 |
| hMAb TSHR1 (10 ng/mL) | 18093 ± 2166 | 9972 ± 697 | 55 |
| 2G2 (1 μg/mL) | 935[a] | 718 ± 161 | 77 |
| TSMAb 1 (1 μg/mL) | 5622 ± 381 | 526[a] | 9 |
| TSMAb 2 (1 μg/mL) | 4325 ± 731 | 444 ± 86 | 10 |
| TSMAb C (10 ng/mL) | 5807 ± 708 | 3706 ± 207 | 64 |
| TSMAb D (1 μg/mL) | 8462 ± 1673 | 3047 ± 395 | 36 |
| TSMAb E (1 μg/mL) | 6729 ± 813 | 3246 ± 612 | 48 |
| TSMAb F (100 ng/mL) | 13964 ± 1780 | 6727 ± 791 | 48 |

[a]mean of duplicate

2G2 is a mouse monoclonal antibody to thyroglobulin (negative control)

TABLE 21d

Stimulation of cyclic AMP production by 6 different mouse thyroid stimulating monoclonal antibodies (mTSMAbs) in CHO cells expressing wild type TSHR and TSHR with Arg109 mutated to Asp.

| Test sample in cyclic AMP assay buffer | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 630 ± 22 | 413 ± 1 | 66 |
| hMAb TSHR1 (10 ng/mL) | 17787 ± 1359 | 3733 ± 395 | 21 |
| 2G2 (1 μg/mL) | 645 ± 103 | 359 ± 113 | 56 |
| TSMAb 1 (1 μg/mL) | 4489 ± 576 | 491 ± 36 | 11 |
| TSMAb 2 (1 μg/mL) | 4102 ± 413 | 278[a] | 7 |
| TSMAb C (10 ng/mL) | 7440 ± 548 | 709[a] | 10 |
| TSMAb D (1 μg/mL) | 9305 ± 1019 | 591 ± 30 | 6 |
| TSMAb E (1 μg/mL) | 8387 ± 720 | 530 ± 52 | 6 |
| TSMAb F (100 ng/mL) | 12292 ± 1280 | 473[a] | 4 |

[a]mean of duplicate

2G2 is a mouse monoclonal antibody to thyroglobulin (negative control)

TABLE 21e

Stimulation of cyclic AMP production by 6 different mouse thyroid stimulating monoclonal antibodies (mTSMAbs) in CHO cells expressing wild type TSHR and TSHR with Lys129 mutated to Ala.

| Test sample in cyclic AMP assay buffer | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 1196 ± 28 | 1002 ± 154 | 84 |
| hMAb TSHR1 (10 ng/mL) | 28890 ± 2504 | 10900 ± 818 | 38 |
| 2G2 (1 μg/mL) | 1396 ± 146 | 331[a] | 24 |
| TSMAb 1 (1 μg/mL) | 6220 ± 850 | 4700 ± 840 | 76 |
| TSMAb 2 (1 μg/mL) | 5706 ± 792 | 3394 ± 560 | 59 |
| TSMAb C (10 ng/mL) | 10288[a] | 540 ± 186 | 5 |
| TSMAb D (1 μg/mL) | 13806 ± 716 | 816 ± 26 | 6 |
| TSMAb E (1 μg/mL) | 8746 ± 968 | 656 ± 82 | 8 |
| TSMAb F (100 ng/mL) | 20126 ± 1972 | 2264[a] | 11 |

[a]mean of duplicate
2G2 is a mouse monoclonal antibody to thyroglobulin (negative control)

TABLE 21f

Stimulation of cyclic AMP production by 6 different mouse thyroid stimulating monoclonal antibodies (mTSMAbs) in CHO cells expressing wild type TSHR and TSHR with Lys183 mutated to Ala.

| Test sample in cyclic AMP assay buffer | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 717 ± 98 | 601 ± 83 | 84 |
| hMAb TSHR1 (10 ng/mL) | 25794 ± 1025 | 3182 ± 771 | 12 |
| 2G2 (1 μg/mL) | 784 ± 77 | 796 ± 104 | 102 |
| TSMAb 1 (1 μg/mL) | 4213[a] | 881 ± 188 | 21 |
| TSMAb 2 (1 μg/mL) | 3455 ± 435 | 524[a] | 15 |
| TSMAb C (10 ng/mL) | 7935[a] | 655[a] | 8 |
| TSMAb D (1 μg/mL) | 9919 ± 983 | 556 ± 89 | 6 |
| TSMAb E (1 μg/mL) | 8487 ± 1541 | 703 ± 20 | 8 |
| TSMAb F (100 ng/mL) | 15068 ± 1503 | 797 ± 131 | 5 |

[a]mean of duplicate
2G2 is a mouse monoclonal antibody to thyroglobulin (negative control)

TABLE 21g

Stimulation of cyclic AMP production by 6 different mouse thyroid stimulating monoclonal antibodies (mTSMAbs) in CHO cells expressing wild type TSHR and TSHR with Lys183 mutated to Asp.

| Test sample in cyclic AMP assay buffer | Cyclic AMP produced (fmol/cell well) (mean ± SD; n = 3) Wild type TSHR | Mutated TSHR | Mutated/ Wild type (%) |
|---|---|---|---|
| Cyclic AMP assay buffer only | 909 ± 51 | 1005 ± 136 | 111 |
| hMAb TSHR1 (10 ng/mL) | 25297[a] | 1755 ± 83 | 7 |
| 2G2 (1 μg/mL) | 1296 ± 126 | 1256 ± 134 | 97 |
| TSMAb 1 (1 μg/mL) | 8228 ± 1348 | 653 ± 174 | 8 |
| TSMAb 2 (1 μg/mL) | 8026 ± 1398 | 370[a] | 5 |
| TSMAb C (10 ng/mL) | 10381 ± 70 | 540 ± 144 | 5 |
| TSMAb D (1 μg/mL) | 16466 ± 5817 | 1350 ± 98 | 8 |
| TSMAb E (1 μg/mL) | 10765 ± 1543 | 325 ± 13 | 8 |
| TSMAb F (100 ng/mL) | 17634 ± 1701 | 390 ± 34 | 2 |

[a]mean of duplicate
2G2 is a mouse monoclonal antibody to thyroglobulin (negative control)

TABLE 22

Summary of effect of mutation (relative to wild type) on stimulation of cyclic AMP production by mouse thyroid stimulating monoclonal antibodies (mTSMAbs)

| aa mutation | marked reduction | reduction | small effect | no effect |
|---|---|---|---|---|
| Arg80 to Asp | 6/6 | 0/6 | 0/6 | 0/6 |
| Glu107 to Ala | 6/6 | 0/6 | 0/6 | 0/6 |
| Arg109 to Ala | 2/6 | 3/6 | 1/6 | 0/6 |
| Arg109 to Asp | 6/6 | 0/6 | 0/6 | 0/6 |
| Lys129 to Ala | 4/6 | 2/6 | 0/6 | 0/6 |
| Lys183 to Ala | 6/6 | 0/6 | 0/6 | 0/6 |
| Lys183 to Asp | 6/6 | 0/6 | 0/6 | 0/6 |
| Arg255 to Asp | 6/6 | 0/6 | 0/6 | 0/6 |

Number of monoclonal antibodies affected/out of 6 monoclonal antibodies tested for each mutation is shown.

TABLE 23a

TSH induced cyclic AMP production in CHO cells expressing wild type TSHR and TSHR with Glu107 mutated to Ala. Effect of different dilutions of serum B3 (Table 9) with TSH antagonist activity A Cyclic AMP levels

| Test sample dilution[a] | Cyclic AMP produced (fmol/cell well) (mean ± SD; n = 3) Wild type TSHR | Mutated TSHR | Mutated/ Wild type (%) |
|---|---|---|---|
| B3 1000× | 1041 ± 143 | 1073 ± 251 | 103 |
| B3 1000× + TSH[b] | 15561 ± 1630 | 10918 ± 601 | 70 |
| B3 100× | 567[c] | 214 ± 24 | 38 |
| B3 100× + TSH[b] | 10246 ± 469 | 478[c] | 5 |
| B3 10× | 161 ± 23 | 168 ± 33 | 104 |
| B3 10× + TSH[b] | 165[c] | 156 ± 26 | 95 |
| HBD 1000× | 877 ± 154 | 1518 ± 195 | 173 |
| HBD 1000× + TSH[b] | 18086 ± 1390 | 11896 ± 1044 | 66 |
| HBD 100× | 931 ± 73 | 1001 ± 244 | 108 |
| HBD 100× + TSH[b] | 18850 ± 1541 | 11777 ± 759 | 62 |
| HBD 10× | 563 ± 302 | 515 ± 308 | 91 |
| HBD 10× +TSH[b] | 20456 ± 1912 | 10284 ± 146 | 50 |

B % inhibition results

| Serum with TSH antagonist activity | % inhibition of TSH stimulation[d] Wild type TSHR | Mutated TSHR |
|---|---|---|
| B3 1000x | 14 | 8 |
| B3 100x | 46 | 96 |
| B3 10x | 99 | 98 |

HBD = Pool of healthy blood donor sera
[a]Test samples in cyclic AMP assay buffer
[b]TSH final concentration = 1.5 ng/mL
[c]mean of duplicate $$^{d}\%\ \text{inhibition} = 100\times\left(1-\frac{\text{cAMP in presence of serum B3 + TSH}}{\text{cAMP in presence of HBD + TSH}}\right)$$

where test sample and HBD dilutions are the same

TABLE 23b

TSH induced cyclic AMP production in CHO cells expressing wild type TSHR and TSHR with Arg109 mutated to Ala. Effect of different dilutions of serum B3 (Table 9) with TSH antagonist activity A Cyclic AMP levels

| Test sample | Cyclic AMP produced (fmol/cell well) (mean ± SD; n = 3) | | Mutated/ Wild |
|---|---|---|---|
| dilution[a] | Wild type TSHR | Mutated TSHR | type (%) |
| B3 1000× | 510 ± 100 | 1224[c] | 240 |
| B3 1000× + TSH[b] | 20938[c] | 12248 ± 824 | 58 |
| B3 100× | 425[c] | 378 ± 55 | 89 |
| B3 100× + TSH[b] | 20790[c] | 10358 ± 1447 | 50 |
| B3 10× | 226 ± 18 | 269 ± 16 | 119 |
| B3 10× + TSH[b] | 349 ± 64 | 294 ± 46 | 84 |
| HBD 1000× | 419[c] | 473[c] | 113 |
| HBD 1000× + TSH[b] | 21126 ± 884 | 14225 ± 2494 | 67 |
| HBD 100× | 462[c] | 478[c] | 103 |
| HBD 100× + TSH[b] | 22146 ± 919 | 11051[c] | 50 |
| HBD 10× | 378 ± 14 | 302[c] | 80 |
| HBD 10× + TSH[b] | 22973 ± 514 | 14197 ± 1977 | 62 |

B % inhibition results

| Serum with TSH | % inhibition of TSH stimulation[d] | |
|---|---|---|
| antagonist activity | Wild type TSHR | Mutated TSHR |
| B3 1000× | 1 | 14 |
| B3 100× | 6 | 6 |
| B3 10× | 98 | 98 |

HBD = Pool of healthy blood donor sera
[a]Test samples in cyclic AMP assay buffer
[b]TSH final concentration = 1.5 ng/mL
[c]mean of duplicate $$^{d}\% \text{ inhibition} = 100\times\left(1-\frac{\text{cAMP in presence of serum B3}+\text{TSH}}{\text{cAMP in presence of HBD}+\text{TSH}}\right)$$

where test sample and HBD dilutions are the same

TABLE 23c

TSH induced cyclic AMP production in CHO cells expressing wild type TSHR and TSHR with Lys183 mutated to Ala. Effect of different dilutions of serum B3 (Table 9) with TSH antagonist activity A Cyclic AMP levels

| Test sample | Cyclic AMP produced (fmol/cell well) (mean ± SD; n = 3) | | Mutated/ Wild |
|---|---|---|---|
| dilution[a] | Wild type TSHR | Mutated TSHR | type (%) |
| B3 1000× | 535 ± 52 | 549 ± 31 | 103 |
| B3 1000× + TSH[b] | 12400 ± 790 | 14656 ± 2399 | 118 |
| B3 100× | 389 ± 36 | 267 ± 12 | 69 |
| B3 100× TSH[b] | 3420 ± 159 | 2929 ± 310 | 86 |
| B3 10× | 149 ± 6 | 150[c] | 101 |
| B3 10× + TSH[b] | 157 ± 21 | 170[c] | 108 |
| HBD 1000× | 569[c] | 648 ± 65 | 114 |
| HBD 1000× + TSH[b] | 12762 ± 150 | 13589 ± 2282 | 106 |
| HBD 100× | 548 ± 16 | 404 ± 237 | 74 |
| HBD 100× + TSH[b] | 13803 ± 747 | 13112 ± 1442 | 95 |
| HBD 10× | 396 ± 102 | 368[c] | 93 |
| HBD 10× + TSH[b] | 11959 ± 940 | 14161 ± 1648 | 118 |

B % inhibition results

| Serum with TSH | % inhibition of TSH stimulation[d] | |
|---|---|---|
| antagonist activity | Wild type TSHR | Mutated TSHR |
| B3 1000× | 3 | −8 |
| B3 100× | 75 | 78 |
| B3 10× | 99 | 99 |

HBD = Pool of healthy blood donor sera
[a]Test samples in cyclic AMP assay buffer
[b]TSH final concentration = 1.5 ng/mL
[c]mean of duplicate $$^{d}\% \text{ inhibition} = 100\times\left(1-\frac{\text{cAMP in presence of serum B3}+\text{TSH}}{\text{cAMP in presence HBD}+\text{TSH}}\right)$$

where test sample and HBD dilutions are the same

TABLE 24

Summary of effect of mutation (relative to wild type) on inhibition of TSH mediated cyclic AMP stimulation by serum B3 (Table 9) with TSH antagonist activity

| aa mutation | Inhibition of TSH mediated cyclic AMP stimulation by serum B3 with TSH antagonist activity |
|---|---|
| Glu107 to Ala | enhanced effect |
| Arg109 to Ala | no effect |
| Lys183 to Ala | no effect |
| Arg255 to Asp | enhanced effect |

TABLE 25

Scatchard analysis of TSH, hMAb TSHR1 Fab and 9D33 MAb binding to wild type (non-mutated) and mutated TSH receptor preparations

| Receptor preparation | Affinity for TSH | Affinity for hMAb TSHR1 Fab | Affinity for 9D33 MAb |
|---|---|---|---|
| Wild type | $6.0 \pm 0.9 \times 10^{9}$ L/mol | $3.4 \pm 1.0 \times 10^{10}$ L/mol | $1.8 \pm 0.7 \times 10^{10}$ L/mol |
| Asp43 to Ala | $3.4 \times 10^{9}$ L/mol | $2.7 \times 10^{10}$ L/mol | $1.4 \times 10^{10}$ L/mol |
| Lys58 to Ala | $5.9 \times 10^{9}$ L/mol | $1.6 \times 10^{10}$ L/mol | 9D33 MAb binding undetectable |
| Ile60 to Ala | $5.1 \times 10^{9}$ L/mol | $4.4 \times 10^{10}$ L/mol | 9D33 MAb binding undetectable |
| Glu61 to Ala | $2.4 \times 10^{9}$ L/mol | $3.4 \times 10^{9}$ L/mol | $0.9 \times 10^{10}$ L/mol |
| Arg80 to Ala | $4.2 \times 10^{9}$ L/mol | hMAb TSHR1 Fab binding undetectable | 9D33 MAb binding undetectable |
| Arg80 to Asp | $2.8 \times 10^{9}$ L/mol | hMAb TSHR1 Fab binding undetectable | 9D33 MAb binding undetectable |
| Tyr82 to Ala | $4.0 \times 10^{9}$ L/mol | $1.8 \times 10^{10}$ L/mol | 9D33 MAb binding undetectable |

TABLE 25-continued

Scatchard analysis of TSH, hMAb TSHR1 Fab and 9D33 MAb binding to wild type (non-mutated) and mutated TSH receptor preparations

| Receptor preparation | Affinity for TSH | Affinity for hMAb TSHR1 Fab | Affinity for 9D33 MAb |
|---|---|---|---|
| Glu107 to Ala | $3.7 \times 10^9$ L/mol | $0.1 \times 10^{10}$ L/mol | $0.6 \times 10^{10}$ L/mol |
| Glu107 to Arg | TSH binding undetectable | hMAb TSHR1 Fab binding undetectable | 9D33 MAb binding undetectable |
| Arg109 to Ala | $1.1 \times 10^9$ L/mol | $2.3 \times 10^{10}$ L/mol | 9D33 MAb binding undetectable |
| Arg109 to Asp | TSH binding undetectable | hMAb TSHR1 Fab binding undetectable | 9D33 MAb binding undetectable |
| Lys129 to Ala | $2.2 \times 10^9$ L/mol | $0.3 \times 10^{10}$ L/mol | 9D33 MAb binding undetectable |
| Lys129 to Asp | TSH binding undetectable | hMAb TSHR1 Fab binding undetectable | 9D33 MAb binding undetectable |
| Phe130 to Ala | $2.4 \times 10^9$ L/mol | $0.3 \times 10^{10}$ L/mol | $0.9 \times 10^{10}$ L/mol |
| Phe134 to Ala | $2.1 \times 10^9$ L/mol | $0.9 \times 10^{10}$ L/mol | $0.5 \times 10^{10}$ L/mol |
| Glu157 to Ala | TSH binding undetectable | $2.2 \times 10^{10}$ L/mol | $1.3 \times 10^{10}$ L/mol |
| Asp160 to Ala | TSH binding undetectable | $1.8 \times 10^{10}$ L/mol | $1.0 \times 10^{10}$ L/mol |
| Glu178 to Ala | $1.0 \times 10^9$ L/mol | $0.5 \times 10^{10}$ L/mol | $1.3 \times 10^{10}$ L/mol |
| Lys183 to Ala | $16 \times 10^9$ L/mol | nt | nt |
| Lys183 to Asp | TSH binding undetectable | hMAb TSHR1 Fab binding undetectable | 9D33 MAb binding undetectable |
| Tyr185 to Ala | $3.4 \times 10^9$ L/mol | $0.4 \times 10^{10}$ L/mol | $0.9 \times 10^{10}$ L/mol |
| Asp203 to Ala | $2.2 \times 10^9$ L/mol | $1.9 \times 10^{10}$ L/mol | $1.4 \times 10^{10}$ L/mol |
| Tyr206 to Ala | TSH binding undetectable | nt | 9D33 MAb binding undetectable |
| Lys209 to Ala | TSH binding undetectable | $1.3 \times 10^{10}$ L/mol | $0.8 \times 10^{10}$ L/mol |
| Asp232 to Ala | TSH binding undetectable | hMAb TSHR1 Fab binding undetectable | 9D33 MAb binding undetectable |
| Asp232 to Arg | TSH binding undetectable | hMAb TSHR1 Fab binding undetectable | 9D33 MAb binding undetectable |
| Gln235 to Ala | $4.9 \times 10^{10}$ L/mol | $2.5 \times 10^{10}$ L/mol | $1.1 \times 10^{10}$ L/mol |
| Lys250 to Ala | TSH binding undetectable | $0.9 \times 10^{10}$ L/mol | $0.6 \times 10^{10}$ L/mol |
| Glu251 to Ala | $2.0 \times 10^9$ L/mol | $1.9 \times 10^{10}$ L/mol | $0.8 \times 10^{10}$ L/mol |
| Arg255 to Ala | $2.3 \times 10^9$ L/mol | $0.7 \times 10^{10}$ L/mol | $0.8 \times 10^{10}$ L/mol |
| Arg255 to Asp | TSH binding undetectable | $0.3 \times 10^{10}$ L/mol | $1.3 \times 10^{10}$ L/mol |
| Thr257 to Ala | TSH binding undetectable | $1.8 \times 10^{10}$ L/mol | $0.7 \times 10^{10}$ L/mol |
| Trp258 to Ala | TSH binding undetectable | $1.4 \times 10^{10}$ L/mol | $1.2 \times 10^{10}$ L/mol |
| Arg274 to Ala | TSH binding undetectable | $0.8 \times 10^{10}$ L/mol | $0.5 \times 10^{10}$ L/mol |
| Asp276 to Ala | $5.5 \times 10^9$ L/mol | $1.6 \times 10^{10}$ L/mol | $1.3 \times 10^{10}$ L/mol |
| Tyr279 to Ala | TSH binding undetectable | $0.7 \times 10^{10}$ L/mol | $0.6 \times 10^{10}$ L/mol |
| Ser281 to Ala | $3.4 \times 10^9$ L/mol | $2.3 \times 10^{10}$ L/mol | $0.9 \times 10^{10}$ L/mol |
| Arg255 to Ala and Trp258 to Ala | TSH binding undetectable | $1.0 \times 10^{10}$ L/mol | $1.1 \times 10^{10}$ L/mol |

nt = not tested

TABLE 26

Binding affinity of hMAb TSHR1 Fab and TSH for the TSH receptor containing amino acid mutations that showed differences between the effect on cyclic AMP stimulation by hormone and antibody

| aa mutation | Affinity for TSH | Affinity for hMAb TSHR1 Fab |
|---|---|---|
| Arg80 to Ala | unchanged | undetectable binding |
| Arg80 to Asp | unchanged | undetectable binding |
| Tyr82 to Ala | unchanged | unchanged |
| Glu107 to Ala | unchanged | markedly reduced |
| Arg109 to Ala | reduced | unchanged |
| Arg109 to Asp | undetectable binding | undetectable binding |
| Lys129 to Ala | unchanged | markedly reduced |
| Lys129 to Asp | undetectable binding | undetectable binding |
| Phe130 to Ala | unchanged | markedly reduced |
| Lys183 to Ala | increased | not tested |
| Lys183 to Asp | undetectable binding | undetectable binding |
| Tyr185 to Ala | unchanged | markedly reduced |
| Asp232 to Ala | undetectable binding | undetectable binding |
| Arg255 to Ala | unchanged | markedly reduced |
| Arg255 to Asp | undetectable binding | markedly reduced |
| Trp258 to Ala | undetectable binding | slightly reduced |
| Arg255 to Ala and Trp258 to Ala | undetectable binding | slightly reduced |

TABLE 27a

Effect of double mutation of TSHR Glu157 to Ala and Asp203 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1737 ± 112 | 1136 ± 109 | 65 |
| 0.3 | 5032 ± 458 | 1686 ± 419 | 34 |
| 1 | 9528 ± 1680 | 2499 ± 1359 | 26 |
| 3 | 14622 ± 2685 | 6831 ± 65 | 47 |
| 10 | 20515 ± 3415 | 9527 ± 1081 | 46 |
| TSH (ng/mL) | | | |
| 0.01 | 953 ± 166 | 1037 ± 56 | 109 |
| 0.03 | 836 ± 447 | 1128 ± 57 | 135 |
| 0.1 | 2083 ± 337 | 1114 ± 113 | 53 |
| 0.3 | 13295 ± 5822 | 1197 ± 112 | 9 |
| 1 | 22327 ± 1531 | 4622 ± 245 | 21 |
| 3 | 20802 ± 6167 | 7710 ± 329 | 37 |
| Cyclic AMP assay buffer | 1108 ± 206 | 1029 ± 67 | |

TABLE 27a-continued

Effect of double mutation of TSHR Glu157 to Ala and Asp203 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 2 | | | |
| hMAb TSHR1 (ng/mL) | | | |
| 0.1 | 2278 ± 607 | 2489 ± 91 | 109 |
| 0.3 | 4233 ± 270 | 2856 ± 227 | 63 |
| 1 | 13534 ± 999 | 5506 ± 1111 | 41 |
| 3 | 20909 ± 500 | 13767 ± 1284 | 66 |
| 10 | 23297 ± 3180 | 19498 ± 1786 | 84 |
| TSH (ng/mL) | | | |
| 0.01 | 1071 ± 531 | 1769 ± 426 | 165 |
| 0.03 | 2110 ± 36 | 2291 ± 230 | 109 |
| 0.1 | 4574 ± 181 | 2306 ± 339 | 50 |
| 0.3 | 12723 ± 362 | 2342 ± 342 | 18 |
| 1 | 22463 ± 916 | 6969 ± 1339 | 31 |
| 3 | 24331 ± 834 | 13458 ± 745 | 55 |
| Cyclic AMP assay buffer | 877 ± 118 | 2467 ± 251 | |

hMAb TSHR1 Fab was used in all experiments

TABLE 27b

Effect of double mutation of TSHR Glu178 to Ala and Asp203 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1845 ± 349 | 2199 ± 25 | 119 |
| 0.3 | 2995 ± 74 | 2388 ± 474 | 80 |
| 1 | 10614 ± 386 | 7005 ± 975 | 66 |
| 3 | 14298 ± 3757 | 13707 ± 903 | 96 |
| 10 | 17794 ± 1486 | 14808 ± 1165 | 83 |
| TSH (ng/mL) | | | |
| 0.01 | 1682 ± 329 | 2574 ± 408 | 153 |
| 0.03 | 1913 ± 132 | 3206 ± 86 | 168 |
| 0.1 | 3881 ± 290 | 3702 ± 114 | 95 |
| 0.3 | 11501 ± 1064 | 10892 ± 616 | 95 |
| 1 | 17275 ± 970 | 16664 ± 1429 | 96 |
| 3 | 19963 ± 2506 | 20605 ± 1452 | 103 |
| Cyclic AMP assay buffer | 895 ± 30 | 1531 ± 114 | |
| Experiment 2 | | | |
| hMAb TSHR1 (ng/mL) | | | |
| 0.1 | 1326 ± 139 | 815 ± 51 | 61 |
| 0.3 | 2244[a] | 1195 ± 57 | 53 |
| 1 | 6558 ± 1708 | 1965 ± 89 | 30 |
| 3 | 14499 ± 3232 | 5238 ± 636 | 36 |
| 10 | 19735 ± 1460 | 10913 ± 2826 | 55 |
| TSH (ng/mL) | | | |
| 0.01 | 949 ± 64 | 637 ± 93 | 67 |
| 0.03 | 1343 ± 240 | 1106 ± 98 | 82 |
| 0.1 | 4351 ± 928 | 1367 ± 120 | 31 |
| 0.3 | 9438 ± 1460 | 2540 ± 232 | 27 |
| 1 | 18296 ± 2078 | 7852 ± 1106 | 43 |
| 3 | 20253 ± 735 | 13321 ± 3239 | 66 |
| Cyclic AMP assay buffer | 613 ± 45 | 500 ± 55 | |

[a]mean of duplicate hMAb TSHR1 Fab was used in all experiments

TABLE 27c

Effect of double mutation of TSHR Asp232 to Ala and Arg255 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1653 ± 187 | 609 ± 20 | 37 |
| 0.3 | 2956 ± 209 | 623 ± 42 | 21 |
| 1 | 9782 ± 1779 | 1153 ± 516 | 12 |
| 3 | 13850 ± 1496 | 1341 ± 424 | 10 |
| 10 | 14827 ± 1864 | 2713 ± 289 | 18 |
| TSH (ng/mL) | | | |
| 0.01 | 1031 ± 94 | 604 ± 39 | 59 |
| 0.03 | 2142 ± 256 | 779 ± 72 | 36 |
| 0.1 | 4658 ± 332 | 1581 ± 139 | 34 |
| 0.3 | 9352 ± 995 | 3877 ± 116 | 41 |
| 1 | 16490 ± 2070 | 5499 ± 486 | 33 |
| 3 | 14656 ± 501 | 5532 ± 1145 | 38 |
| Cyclic AMP assay buffer | 671 ± 36 | 608 ± 20 | |
| Experiment 2 | | | |
| hMAb TSHR1 (ng/mL) | | | |
| 0.1 | 1166 ± 68 | 849 ± 33 | 73 |
| 0.3 | 2407 ± 359 | 967 ± 70 | 40 |
| 1 | 6155 ± 2046 | 1227 ± 129 | 20 |
| 3 | 13626 ± 2714 | 1315 ± 128 | 10 |
| 10 | 14114 ± 3164 | 2830 ± 386 | 20 |
| TSH (ng/mL) | | | |
| 0.01 | 1373 ± 284 | 1254 ± 39 | 91 |
| 0.03 | 2761 ± 611 | 1445 ± 123 | 52 |
| 0.1 | nd | 2793 ± 528 | nd |
| 0.3 | 10839 ± 1399 | 5434 ± 543 | 50 |
| 1 | 18337 ± 2139 | 6879 ± 748 | 38 |
| 3 | 16581 ± 5023 | 6697 ± 367 | 40 |
| Cyclic AMP assay buffer | 747 ± 160 | 749 ± 148 | |

hMAb TSHR1 Fab was used in all experiments nd = not determined

TABLE 27d

Effect of double mutation of TSHR Asp232 to Arg and Arg255 to Asp on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1411 ± 110 | 1098 ± 86 | 78 |
| 0.3 | 5592[a] | 1036 ± 91 | 19 |
| 1 | 8555[a] | 2660 ± 164 | 31 |
| 3 | 16325[a] | 2976 ± 246 | 18 |
| 10 | 20490[a] | 196 ± 83 | 10 |
| TSH (ng/mL) | | | |
| 0.01 | 1456 ± 63 | 1018 ± 106 | 70 |
| 0.03 | 1755 ± 173 | 1079 ± 17 | 61 |
| 0.1 | 5811 ± 153 | 1087 ± 95 | 19 |
| 0.3 | 10213 ± 897 | 2613[a] | 26 |
| 1 | 20782 ± 3649 | 2703[a] | 13 |
| 3 | 25952 ± 435 | 2743[a] | 11 |
| Cyclic AMP assay buffer | 1233 ± 208 | 1095 ± 71 | |

TABLE 27d-continued

Effect of double mutation of TSHR Asp232 to Arg and Arg255 to Asp on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 2 | | | |
| hMAb TSHR1 (ng/mL) | | | |
| 0.1 | 1649 ± 194 | 968 ± 72 | 59 |
| 0.3 | 2786 ± 320 | 1051 ± 60 | 38 |
| 1 | 8364 ± 344 | 949 ± 305 | 11 |
| 3 | 13271 ± 1940 | 794 ± 316 | 6 |
| 10 | 17431 ± 3371 | 399 ± 83 | 2 |
| TSH (ng/mL) | | | |
| 0.01 | 1185 ± 49 | 1219 ± 246 | 103 |
| 0.03 | 1745 ± 269 | 1463 ± 98 | 84 |
| 0.1 | 2938 ± 462 | 1571 ± 173 | 53 |
| 0.3 | 8603 ± 1998 | 1274 ± 300 | 15 |
| 1 | 19137 ± 1060 | 1291 ± 243 | 7 |
| 3 | 19796 ± 947 | 832 ± 330 | 4 |
| Cyclic AMP assay buffer | 1032 ± 76 | 836 ± 179 | |

[a]mean of duplicate hMAb TSHR1 Fab was used in all experiments

TABLE 27e

Effect of double mutation of TSHR Asp232 to Ala and Trp258 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 1371 ± 89 | 387 ± 51 | 28 |
| 0.3 | 2655 ± 312 | 299 ± 173 | 11 |
| 1 | 9988 ± 2996 | 161[a] | 2 |
| 3 | 12979 ± 2336 | 178 ± 28 | 1 |
| 10 | 11756 ± 1444 | 161[a] | 1 |
| TSH (ng/mL) | | | |
| 0.01 | 904 ± 85 | 400 ± 81 | 44 |
| 0.03 | 1555 ± 196 | 391 ± 50 | 25 |
| 0.1 | 3714 ± 1022 | 203 ± 185 | 5 |
| 0.3 | 9529[a] | 238 ± 127 | 2 |
| 1 | 11451 ± 782 | 163 ± 32 | 1 |
| 3 | 11743 ± 761 | 158 ± 25 | 1 |
| Cyclic AMP assay buffer | 739 ± 94 | 293 ± 155 | |
| Experiment 2 | | | |
| hMAb TSHR1 (ng/mL) | | | |
| 0.1 | 1735 ± 359 | 880 ± 62 | 51 |
| 0.3 | 3378 ± 590 | 664 ± 153 | 20 |
| 1 | 8934 ± 3094 | 529 ± 132 | 6 |
| 3 | 8362 ± 1905 | 746 ± 144 | 9 |
| 10 | 18753 ± 1985 | 683 ± 84 | 4 |
| TSH (ng/mL) | | | |
| 0.01 | nd | 888 ± 52 | nd |
| 0.03 | 1726 ± 322 | 950 ± 68 | 55 |
| 0.1 | nd | 973 ± 211 | nd |
| 0.3 | 17281 ± 542 | 749 ± 24 | 4 |

TABLE 27e-continued

Effect of double mutation of TSHR Asp232 to Ala and Trp258 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| 1 | 14866 ± 2236 | 657 ± 134 | 4 |
| 3 | 22039 ± 4147 | 610 ± 59 | 3 |
| Cyclic AMP assay buffer | 755 ± 305 | 647 ± 203 | |

[a]mean of duplicate hMAb TSHR1 Fab was used in all experiments nd = not determined TABLE 27f Effect of triple mutation of TSHR Asp232 to Ala, Arg255 to Ala and Trp258 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 | | | |
| hMAb TSHR1 (ng/mL) | | | |
| 0.1 | 2232 ± 344 | 757 ± 111 | 34 |
| 0.3 | 4812 ± 202 | 825 ± 97 | 17 |
| 1 | 12703 ± 1110 | 610 ± 38 | 5 |
| 3 | 20706 ± 7441 | 545 ± 221 | 3 |
| 10 | 25117 ± 2140 | 721 ± 280 | 3 |
| TSH (ng/mL) | | | |
| 0.01 | 1850 ± 307 | 1282 ± 278 | 69 |
| 0.03 | 2715 ± 486 | 1177 ± 341 | 43 |
| 0.1 | 5609 ± 757 | 1327 ± 31 | 24 |
| 0.3 | 14284 ± 1250 | 771 ± 320 | 5 |
| 1 | 21333 ± 2573 | 1822 ± 280 | 9 |
| 3 | 26438 ± 4181 | 1156 ± 501 | 4 |
| Cyclic AMP assay buffer | 997 ± 249 | 752 ± 95 | |
| Experiment 2 | | | |
| hMAb TSHR1 (ng/mL) | | | |
| 0.1 | 1305 ± 30 | 389 ± 81 | 30 |
| 0.3 | 3818 ± 743 | 328 ± 33 | 9 |
| 1 | 8506 ± 1163 | 309 ± 56 | 4 |
| 3 | 18696 ± 553 | ud | nd |
| 10 | 27645 ± 1765 | ud | nd |
| TSH (ng/mL) | | | |
| 0.01 | 1234 ± 104 | 423 ± 138 | 4 |
| 0.03 | 1621 ± 145 | 439 ± 201 | 27 |
| 0.1 | 5228 ± 415 | 809 ± 257 | 15 |
| 0.3 | 15209 ± 2728 | ud | nd |
| 1 | 20651 ± 720 | 364 ± 110 | 2 |
| 3 | 25628 ± 256 | 422 ± 47 | 2 |
| Cyclic AMP assay buffer | 1346 ± 29 | 374 ± 126 | |

hMAb TSHR1 Fab was used in all experiments ud = undetectable nd = not determined TABLE 27g Effect of double mutation of TSHR Trp258 to Ala and Lys183 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 1718 ± 13 | 622 ± 49 | 36 |
| 0.3 | 5342[a] | 792 ± 100 | 15 |
| 1 | 9732 ± 1608 | 995 ± 223 | 10 |
| 3 | 16827 ± 1629 | 1335 ± 174 | 8 |
| 10 | 20111 ± 1948 | 3233 ± 1444 | 16 |
| TSH (ng/mL) | | | |
| 0.01 | 1436[a] | 1304 ± 105 | 91 |
| 0.03 | 1640 ± 168 | 2394 ± 891 | 146 |
| 0.1 | 4569 ± 866 | 5146 ± 407 | 113 |
| 0.3 | 12178 ± 887 | 10690 ± 1722 | 88 |
| 1 | 18346 ± 4068 | 13288 ± 2771 | 72 |
| 3 | 21378 ± 1576 | 19801 ± 2390 | 93 |
| Cyclic AMP assay buffer | 548 ± 62 | 625 ± 57 | 114 |

[a]mean of duplicate hMAb TSHR1 Fab was used in all experiments

TABLE 27h

Effect of double mutation of TSHR Trp258 to Ala and Tyr185 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| Experiment 1 hMAb TSHR1 (ng/mL) | | | |
| 0.1 | 2376 ± 212 | 1130 ± 235 | 48 |
| 0.3 | 1982 ± 366 | 1117 ± 168 | 56 |
| 1 | 5949 ± 82 | 2012 ± 289 | 34 |
| 3 | 11555 ± 2562 | 3347 ± 546 | 29 |
| 10 | 14591 ± 3475 | 5184 ± 558 | 35 |
| TSH (ng/mL) | | | |
| 0.01 | 793 ± 87 | 1096 ± 221 | 138 |
| 0.03 | 1184 ± 307 | 2202 ± 916 | 186 |
| 0.1 | 1761 ± 122 | nd | nd |
| 0.3 | 6254 ± 381 | nd | nd |

TABLE 27h-continued

Effect of double mutation of TSHR Trp258 to Ala and Tyr185 to Ala on stimulation of cyclic AMP in CHO cells containing TSHR by hMAb TSHR1 and TSH

| | Cyclic AMP produced (fmol/cell well) mean ± SD (n = 3) | | Mutated/ Wild |
|---|---|---|---|
| | Wild type TSHR | Mutated TSHR | type (%) |
| 1 | 10869 ± 1184 | 17880 ± 2456 | 165 |
| 3 | 14479 ± 246 | 20189 ± 2735 | 139 |
| Cyclic AMP assay buffer | 625 ± 72 | 668 ± 39 | |
| Experiment 2 hMAb TSHR1 (ng/mL) | | | |
| 0.1 | 1133 ± 113 | 890 ± 75 | 79 |
| 0.3 | 3122 ± 134 | 941 ± 31 | 30 |
| 1 | 8972 ± 700 | 1477 ± 82 | 16 |
| 3 | 14236 ± 940 | 2406 ± 337 | 14 |
| 10 | 16292 ± 1113 | 4418 ± 1000 | 27 |
| TSH (ng/mL) | | | |
| 0.01 | 814 ± 147 | 873 ± 43 | 107 |
| 0.03 | 885 ± 142 | 1409 ± 177 | 159 |
| 0.1 | 2754 ± 435 | 2339 ± 116 | 85 |
| 0.3 | 6713 ± 647 | 4650 ± 871 | 69 |
| 1 | 13019 ± 1190 | 13522 ± 1159 | 104 |
| 3 | 17402 ± 768 | 20202 ± 1233 | 116 |
| Cyclic AMP assay buffer | 550 ± 16 | 846 ± 65 | |

hMAb TSHR1 Fab was used in all experiments nd = not determined

TABLE 28

Summary of effects of mutation (relative to wild type) on stimulation of CHO cells containing mutated TSHR

| aa mutation | TSH stimulation | hMAb TSHR1 Fab stimulation |
|---|---|---|
| Glu157 to Ala and Asp203 to Ala | marked reduction | some reduction |
| Glu178 to Ala and Asp203 to Ala | no effect | no effect |
| Asp232 to Ala and Arg255 to Ala | marked reduction | marked reduction |
| Asp232 to Arg and Arg255 to Asp | marked reduction | marked reduction |
| Asp232 to Ala and Trp258 to Ala | marked reduction | marked reduction |
| Asp232 to Ala, Arg255 to Ala and Trp258 to Ala | marked reduction | marked reduction |
| Trp258 to Ala and Lys183 to Ala | no effect | marked reduction |
| Trp258 to Ala and Tyr185 to Ala | no effect | marked reduction |

TABLE 29

Scatchard analysis of TSH, hMAb TSHR1 Fab and 9D33 MAb binding to wild type (non-mutated) and mutated TSH receptor preparations

| Receptor preparation | Affinity for TSH | Affinity for hMAb TSHR1 Fab | Affinity for 9D33 MAb |
|---|---|---|---|
| Wild type | $6.0 \pm 0.9 \times 10^{9}$ L/mol | $3.4 \pm 1.0 \times 10^{10}$ L/mol | $1.8 \pm 0.7 \times 10^{10}$ L/mol |
| Asp232 to Ala and Arg255 to Ala | TSH binding undetectable | nt | 9D33 MAb binding undetectable |
| Asp232 to Arg and Arg255 to Asp | TSH binding undetectable | hMAb TSHR1 Fab binding undetectable | 9D33 MAb binding undetectable |
| Asp232 to Ala and Trp258 to Ala | TSH binding undetectable | hMAb TSHR1 Fab binding undetectable | 9D33 MAb binding undetectable |
| Asp232 to Ala, Arg255 to Ala and Trp258 to Ala | TSH binding undetectable | hMAb TSHR1 Fab binding undetectable | 9D33 MAb binding undetectable |

TABLE 29-continued

Scatchard analysis of TSH, hMAb TSHR1 Fab and 9D33 MAb binding to wild type (non-mutated) and mutated TSH receptor preparations

| Receptor preparation | Affinity for TSH | Affinity for hMAb TSHR1 Fab | Affinity for 9D33 MAb |
|---|---|---|---|
| Glu157 to Ala and Asp203 to Ala | TSH binding undetectable | $1.5 \times 10^{10}$ L/mol | $0.6 \times 10^{10}$ L/mol |
| Glu178 to Ala and Asp203 to Ala | TSH binding undetectable | $0.2 \times 10^{10}$ L/mol | $0.8 \times 10^{10}$ L/mol |
| Tyr185 to Ala and Lys183 to Ala | $13.9 \times 10^{9}$ L/mol | nt | $0.6 \times 10^{10}$ L/mol |
| Trp258 to Ala and Lys183 to Ala | TSH binding undetectable | hMAb TSHR1 Fab binding undetectable | 9D33 MAb binding undetectable |
| Trp258 to Ala and Tyr185 to Ala | TSH binding undetectable | $0.2 \times 10^{10}$ L/mol | $0.9 \times 10^{10}$ L/mol |
| Arg255 to Ala and Lys183 to Ala | TSH binding undetectable | hMAb TSHR1 Fab binding undetectable | 9D33 MAb binding undetectable |
| Arg255 to Ala and Tyr185 to Ala | TSH binding undetectable | $0.1 \times 10^{10}$ L/mol | $0.9 \times 10^{10}$ L/mol |
| Arg255 to Ala, Lys183 to Ala and Tyr185 to Ala | TSH binding undetectable | hMAb TSHR1 Fab binding undetectable | $0.3 \times 10^{10}$ L/mol |
| Trp258 to Ala, Lys183 to Ala and Tyr185 to Ala | TSH binding undetectable | hMAb TSHR1 Fab binding undetectable | 9D33 MAb binding undetectable |
| Arg255 to Ala, Trp258 to Ala and Tyr185 to Ala | TSH binding undetectable | $0.1 \times 10^{10}$ L/mol | $0.8 \times 10^{10}$ L/mol |
| Arg255 to Ala, Trp258 to Ala, Tyr185 to Ala and Lys183 to Ala | TSH binding undetectable | hMAb TSHR1 Fab binding undetectable | 9D33 MAb binding undetectable |

nt = not tested

The invention claimed is:

1. A mutated thyrotropin receptor (TSHR) preparation which includes a mutated TSHR consisting of a full length wild type human TSHR encoded by the nucleotide sequence of Swiss Prot: accession number P16473 with only one point mutation, wherein an amino acid Arg at a position corresponding to amino acid 255 of the full length wild type human TSHR encoded by the nucleotide sequence of Swiss Prot: accession number P16473 has been mutated to a different amino acid residue, whereby said mutated TSHR preparation differentially interacts with patient serum stimulating TSHR autoantibodies, patient serum blocking TSHR autoantibodies and TSH, in that (i) the stimulatory effect of patient serum stimulating TSHR autoantibodies interacting with the mutated TSHR preparation is substantially reduced or essentially abolished, when compared to the stimulatory effect of the patient serum stimulating TSHR autoantibodies interacting with a reference TSHR preparation which has an amino acid sequence corresponding to that of said mutated TSHR preparation with the exception that said mutation of Arg at a position corresponding to amino acid 255 of a full length wild type human TSHR is not present in said reference TSHR preparation, (ii) the stimulatory effect of TSH when interacting with the mutated TSHR preparation is essentially unaffected, when compared to the stimulatory effect of TSH interacting with said reference TSHR preparation, and (iii) the blocking effect of patient serum blocking TSHR autoantibodies interacting with the mutated TSHR preparation is essentially unaffected or increased, when compared to the blocking effect of the patient serum blocking TSHR autoantibodies interacting with said reference TSHR preparation, whereby said mutated TSHR preparation is effective in the differential screening and identification of patient serum stimulating TSHR autoantibodies, patient serum blocking TSHR autoantibodies and TSH in a sample of body fluid being screened.

2. A mutated TSHR preparation according to claim 1, wherein the Arg at the position corresponding to amino acid 255 of the full length wild type human TSHR is point mutated to a negatively charged amino acid residue.

3. A mutated TSHR preparation according to claim 2, wherein the Arg at the position corresponding to amino acid 255 of the full length wild type human TSHR is point mutated to Asp.

4. A mutated thyrotropin receptor (TSHR) preparation which includes a mutated TSHR consisting of a full length wild type human TSHR encoded by the nucleotide sequence of Swiss Prot: accession number P16473 with only one point mutation, wherein an amino acid Arg at the position corresponding to amino acid 255 of the full length wild type human TSHR encoded by the nucleotide sequence of Swiss Prot: accession number P16473 has been mutated to Asp in said mutated TSHR preparation.

5. A mutated TSHR preparation according to claim 1, which comprises a mutated fragment of a full length wild type human TSHR encoded by the nucleotide sequence of Swiss Prot: accession number P16473.

6. A kit comprising a mutated TSHR preparation of claim 1, together with detection means which enable monitoring of the differential interaction of the mutated TSHR preparation with stimulating TSHR autoantibodies, blocking TSHR autoantibodies and TSH, present in a sample of body fluid obtained from a subject suspected of suffering from, susceptible to, having or recovering from autoimmune disease associated with an immune reaction to the TSHR.

7. The kit according to claim 6, further comprising a therapeutically effective amount of at least one therapeutic agent effective in the treatment of autoimmune disease associated with an immune reaction to the TSHR.

8. A composition comprising a mutated TSHR preparation according to claim 1, together with a pharmaceutically acceptable carrier, diluent or excipient therefore.

9. A composition comprising a mutated TSHR preparation according to claim 4, together with a pharmaceutically acceptable carrier, diluent or excipient therefore.

* * * * *